(12) United States Patent
Kiesman et al.

(10) Patent No.: US 6,649,600 B1
(45) Date of Patent: Nov. 18, 2003

(54) ADENOSINE RECEPTOR ANTAGONISTS AND METHODS OF MAKING AND USING THE SAME

(75) Inventors: William F. Kiesman, Wayland, MA (US); Carol L. Ensinger, Chelmsford, MA (US); Russell C. Petter, Stow, MA (US); James E. Dowling, Scituate, MA (US); Gnanasambandam Kumaravel, Westford, MA (US); He Xi Chang, Belmont, MA (US); Ko Chung Lin, Lexington, MA (US)

(73) Assignee: Biogen, Inc., Cambridge, MA (US)

( * ) Notice: Subject to any disclaimer, the term of this patent is extended or adjusted under 35 U.S.C. 154(b) by 0 days.

(21) Appl. No.: 09/711,543

(22) Filed: Nov. 13, 2000

Related U.S. Application Data

(60) Provisional application No. 60/165,191, filed on Nov. 12, 1999.

(51) Int. Cl.[7] .................. C07D 519/00; C07D 473/06; A61P 11/06; A61P 3/10; A61P 13/12
(52) U.S. Cl. .............. 514/81; 514/263.22; 514/263.24; 514/263.34; 514/263.35; 514/263.36; 544/244; 544/267; 544/268; 544/270; 544/271; 544/272; 544/273
(58) Field of Search ............................... 544/244, 267, 544/268, 270, 271, 272, 273; 514/81, 263, 265, 263.22, 263.24, 263.34, 263.35, 263.36

(56) References Cited

U.S. PATENT DOCUMENTS

| | | |
|---|---|---|
| 5,270,316 A | 12/1993 | Suzuki et al. |
| 5,290,782 A | 3/1994 | Suzuki et al. |
| 5,525,607 A | 6/1996 | Suzuki et al. |
| 5,532,368 A | 7/1996 | Kufner-Muhl et al. |
| 5,641,784 A | 6/1997 | Kufner-Muhl et al. |

FOREIGN PATENT DOCUMENTS

| | | |
|---|---|---|
| DE | 3843117 A1 | 6/1990 |
| DE | 4019892 A1 | 1/1992 |
| DE | 19816857 A1 | 10/1999 |
| EP | 0415456 A2 | 3/1991 |
| EP | 0423805 A3 | 4/1991 |
| EP | 0501379 A2 | 9/1992 |
| EP | 0541120 A2 | 5/1993 |
| EP | 0556778 A2 | 8/1993 |
| EP | 0560354 A1 | 9/1993 |
| EP | 0619316 A1 | 10/1994 |
| WO | WO94/03456 | 2/1994 |
| WO | WO94/16702 | 8/1994 |
| WO | WO98/57644 | 12/1998 |
| WO | WO98/57645 | 12/1998 |
| WO | WO00/01388 | 1/2000 |

OTHER PUBLICATIONS

PDR, 1995 edition, p. 544.*
Mc_graw–Hill Dictionary of Chemistry, 1997, p. 297.*
The Merck Manual of Diagnosis and Therapy, entry for Ascites.*
J. Shimada et al. "8–Polycycloalkyl–1, 3–dipropylxanthines as Potent and Selective Antagonists for A1–Adenosine Receptors", J. Med. Chem., vol. 35, No. 5, 1992, pp. 924–930, XP002160035.
Patent Abstracts of Japan, vol. 017, No. 063, Feb. 8, 1993 & JP 04 270222 A, Sep. 25, 1992.
Patent Abstracts of Japan, vol. 017, No. 200, Apr. 20, 1993 & JP 04 346986 A, Dec. 2, 1992.
Suzuki et al., "Adenosine $A_1$ Antagognists. 2. † Structure–Activity Relationships on Diuretic Activities and Protective Effects against Acute Renal Failure"; J. Med. Chem. 1992, 35, 3066–30 75.

* cited by examiner

*Primary Examiner*—Mark L. Berch
(74) *Attorney, Agent, or Firm*—Fish & Neave

(57) ABSTRACT

The invention is based on the discovery that compounds of Formula I are unexpectedly highly potent and selective inhibitors of the adenosine $A_1$ receptor. Adenosine $A_1$ antagonists can be usefull in the prevention and/or treatment of numerous diseases, including cardiac and circulatory disorders, degenerative disorders of the central nervous system, respiratory disorders, and many diseases for which diuretic treatment is suitable.

In one embodiment, the invention features a compound of formula I:

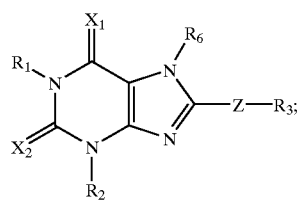

(I)

wherein:

$R_3$ is an optionally substituted bicyclic, tricylic, or pentacyclic group selected from:

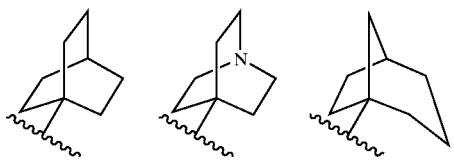

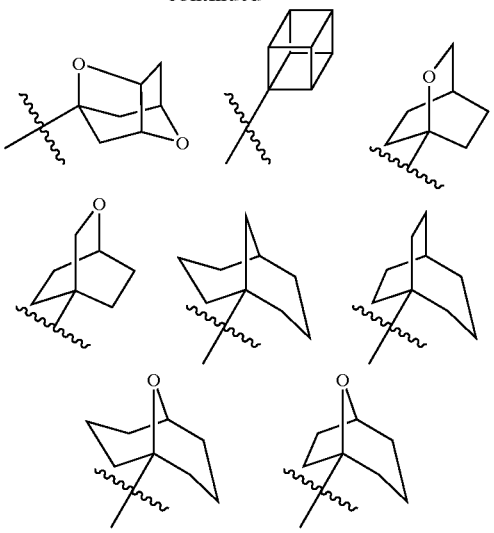

and wherein $R_1$, $R_2$, $R_6$, $X_1$, $X_2$, and Z are as described in the specification.

38 Claims, 19 Drawing Sheets

ADENOSINE RECEPTOR ANTAGONISTS AND METHODS OF MAKING AND USING THE SAME

CROSS-REFERENCE TO RELATED APPLICATIONS

This application claims priority from U.S. Provisional Application Serial No. 60/165,191, filed on Nov. 12, 1999.

BACKGROUND OF THE INVENTION

The invention relates to antagonists of the adenosine receptors and methods of making and using the same in the treatment of diseases.

Adenosine is an intracellular and extracellular messenger generated by all cells in the body. It is also generated extracellularly by enzymatic conversion. Adenosine binds to and activates seven transmembrane G-protein coupled receptors, eliciting a variety of physiological responses. Adenosine itself, substances that mimic the actions of adenosine (agonists), and substances that antagonize its actions have important clinical applications. Adenosine receptors are divided into four known subtypes (i.e., $A_1$, $A_{2a}$, $A_{2b}$, and $A_3$). These subtypes elicit unique and sometimes opposing effects. Activation of the adenosine $A_1$ receptor, for example, elicits an increase in renal vascular resistance while activation of the adenosine $A_{2a}$ receptor elicits a decrease in renal vascular resistance.

In most organ systems, periods of metabolic stress result in significant increases in the concentration of adenosine in the tissue. The heart, for instance, produces and releases adenosine to mediate adaptive responses to stress, such as reductions in heart rate and coronary vasodilatation. Likewise, adenosine concentrations in kidneys increase in response to hypoxia, metabolic stress and many nephrotoxic substances. The kidneys also produce adenosine constitutively. The kidneys adjust the amount of constitutively produced adenosine in order to regulate glomerular filtration and electrolyte reabsorption. Regarding control of glomerular filtration, activation of $A_1$ receptors leads to constriction of afferent arterioles while activation of $A_{2a}$ receptors leads to dilatation of efferent arterioles. Activation of $A_{2a}$ receptors may also exert vasodilatory effects on the afferent arteriole. Overall, the effect of activation of these glomerular adenosine receptors is to reduce glomerular filtration rate. In addition, $A_1$ adenosine receptors are located in the proximal tubule and distal tubular sites. Activation of these receptors stimulates sodium reabsorption from the tubular lumen. Accordingly, blocking the effects of adenosine on these receptors will produce a rise in glomerular filtration rate and an increase in sodium excretion.

SUMMARY OF THE INVENTION

The invention is based on the discovery that compounds of Formula I are unexpectedly highly potent and selective inhibitors of particular subtypes of adenosine receptors. Adenosine antagonists can be useful in the prevention and/or treatment of numerous diseases, including cardiac and circulatory disorders, degenerative disorders of the central nervous system, respiratory disorders, and many diseases for which diuretic treatment is suitable.

In one embodiment, the invention features a compound of formula I:

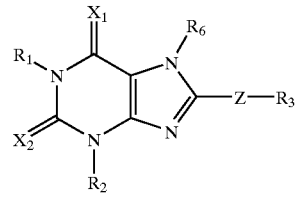

(I)

In formula I, $R_1$ and $R_2$ can, independently, be:
a) hydrogen;
b) alkyl, alkenyl of not less than 3 carbons, or alkynyl of not less than 3 carbons (e.g., where the alkyl, alkenyl, or alkynyl can be unsubstituted or can be functionalized with one or more substituents selected from hydroxy, alkoxy, amino, alkylamino, dialkylamino, heterocyclyl, acylamino, alkylsulfonylamino, and heterocyclylcarbonylamino; or
c) aryl or substituted aryl;

$R_3$ is selected from the group consisting of:
(a) a bicyclic, tricyclic or pentacyclic group selected from:

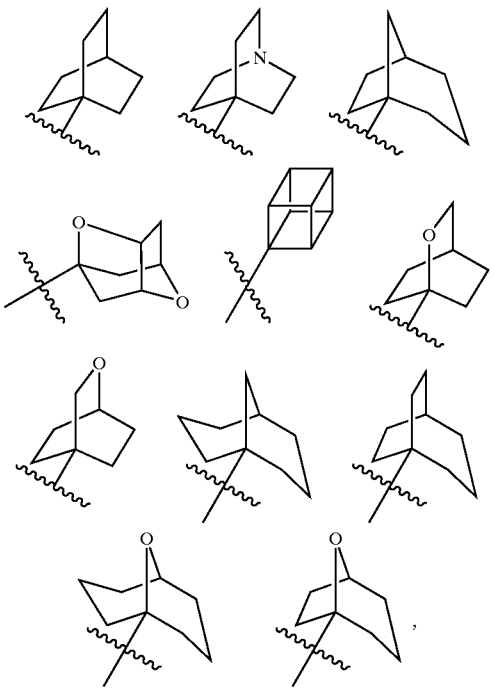

where the bicyclic or tricyclic group can be unsubstituted or can be functionalized with one or more substitents selected from:
(a) alkyl, alkenyl, and alkynyl; where each alkyl, alkenyl, or alkynyl group can be unsubstituted or can be functionalized with one or more substituents selected from the group consisting of (amino)($R_5$) acylhydrazinylcarbonyl, (amino)($R_5$) acyloxycarboxy, (hydroxy)(carboalkoxy) alkylcarbamoyl, acyloxy, aldehydo, alkenylsulfonylamino, alkoxy, alkoxycarbonyl, alkylaminoalkylamino, alkylphosphono, alkylsulfonylamino, carbamoyl, $R_5$, $R_5$-alkoxy, $R_5$-alkylamino, cyano, cyanoalkylcarbamoyl, cycloalkylamino, dialkylamino, dialkylaminoalkylamino, dialkylphosphono, haloalkylsulfonylamino, heterocyclylalkylamino, heterocyclylcarbamoyl, hydroxy, hydroxyalkylsulfonylamino, oximino, phosphono, substituted aralkylamino, substituted arylcarboxyalkoxycarbonyl, substituted heteroarylsulfonylamino, substituted heterocyclyl, thiocarbamoyl, and trifluoromethyl; or (b) (alkoxycarbonyl)aralkylcarbamoyl, aldehydo, alkenoxy, alkenylsulfonylamino, alkoxy, alkoxycarbonyl, alkylcarbamoyl, alkoxycarbonylamino, alkylsulfonylamino, alkylsulfonyloxy, amino, aminoalkylaralkylcarbamoyl, aminoalkylcarbamoyl, aminoalkylheterocyclylalkylcarbamoyl, aminocycloalkylalkylcycloalkylcarbamoyl, aminocycloalkylcarbamoyl, aralkoxycarbonylamino, arylheterocyclyl, aryloxy, arylsulfonylamino, arylsulfonyloxy, carbamoyl, carbonyl, —$R_5$, $R_5$-alkoxy, $R_5$-alkyl(alkyl)amino, $R_5$-alkylalkylcarbamoyl, $R_5$-alkylamino, $R_5$-alkylcarbamoyl, $R_5$-alkylsulfonyl, $R_5$-alkylsulfonylamino, $R_5$-alkylthio, $R_5$-heterocyclylcarbonyl, cyano, cycloalkylamino, dialkylaminoalkylcarbamoyl, halogen, heterocyclyl, heterocyclylalkylamino, hydroxy, oximino, phosphate, substituted aralkylamino, substituted heterocyclyl, substituted heterocyclylsulfonylamino, sulfoxyacylamino, or thiocarbamoyl; and (b) the tricyclic group:

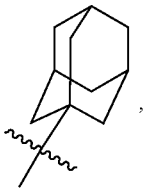

where the tricyclic group is functionalized with one or more substitents selected from the group consisting of:
(a) alkyl, alkenyl, and alkynyl; wherein each alkyl, alkenyl, or alkynyl group is either unsubstituted or functionalized with one or more substituents selected from the group consisting of (amino)($R_5$) acylhydrazinylcarbonyl, (amino)($R_5$) acyloxycarboxy, (hydroxy)(carboalkoxy) alkylcarbamoyl, acyloxy, aldehydo, alkenylsulfonylamino, alkoxy, alkoxycarbonyl, alkylaminoalkylamino, alkylphosphono, alkylsulfonylamino, carbamoyl, $R_5$, $R_5$-alkoxy, $R_5$-alkylamino, cyano, cyanoalkylcarbamoyl, cycloalkylamino, dialkylamino, dialkylaminoalkyiamino, dialkylphosphono, haloalkylsulfonylamino, heterocyclylalkylamino, heterocyclylcarbamoyl, hydroxy, hydroxyalkylsulfonylamino, oximino, phosphono, substituted aralkylamino, substituted arylcarboxyalkoxycarbonyl, substituted heteroarylsulfonylamino, substituted heterocyclyl, thiocarbamoyl, and trifluoromethyl; and (b) (alkoxycarbonyl)aralkylcarbamoyl, aldehydo, alkenoxy, alkenylsulfonylamino, alkoxy, alkoxycarbonyl, alkylcarbamoyl, alkoxycarbonylamino, alkylsulfonylamino, alkylsulfonyloxy, amino, aminoalkylaralkylcarbamoyl, aminoalkylcarbamoyl, aminoalkylheterocyclylalkylcarbamoyl, aminocycloalkylalkylcycloalkylcarbamoyl, aminocycloalkylcarbamoyl, aralkoxycarbonylamino, arylheterocyclyl, aryloxy, arylsulfonylamino, arylsulfonyloxy, carbamoyl, carbonyl, —$R_5$, $R_5$-alkoxy, $R_5$-alkyl(alkyl)amino, $R_5$-alkylalkylcarbamoyl, $R_5$-alkylamino, $R_5$-alkylcarbamoyl, $R_5$-alkylsulfonyl, $R_5$-alkylsulfonylamino, $R_5$-alkylthio, $R_5$-heterocyclylcarbonyl, cyano, cycloalkylamino, dialkylaminoalkylcarbamoyl, halogen, heterocyclyl, heterocyclylalkylamino, oximino, phosphate, substituted aralkylamino, substituted heterocyclyl, substituted heterocyclylsulfonylamino, sulfoxyacylamino, and thiocarbamoyl;

$R_4$ can be hydrogen, $C_{1-4}$-alkyl, $C_{1-4}$-alkyl-$CO_2H$, or phenyl; where the $C_{1-4}$-alkyl, $C_{1-4}$-alkyl-$CO_2H$, and phenyl groups can be unsubstituted or can be functionalized with one, two, three, or more substituents such as halogen, —OH, —OMe, —$NH_2$, —$NO_2$, and benzyl, or benzyl functionalized with one, two, three, or more substituents such as halogen, —OH, —OMe, —$NH_2$, and —$NO_2$;

$R_5$ can be —$CH_2COOH$, —$C(CF_3)_2OH$, —$CONHNHSO_2CF_3$, —$CONHOR_4$, —$CONHSO_2R_4$, —$CONHSO_2NHR_4$, —$C(OH)R_4PO_3H_2$, —$NHCOCF_3$, —$NHCONHSO_2R_4$, —$NHPO_3H_2$, —$NHSO_2R_4$, —$NHSO_2NHCOR_4$, —$OPO_3H_2$, —$OSO_3H$, —$PO(OH)R_4$, —$PO_3H_2$, —$SO_3H$, —$SO_2NHR_4$, —$SO_3NHCOR_4$, —$SO_3NHCONHCO_2R_4$, or any of the following:

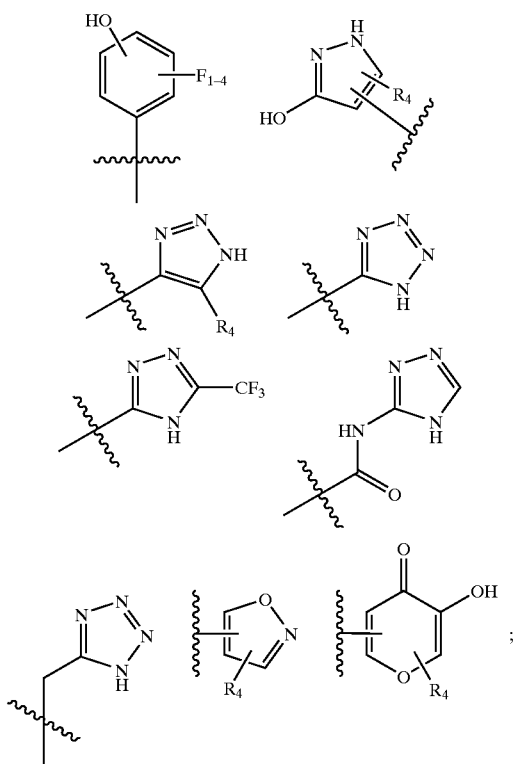

$X_1$ and $X_2$ are chosen from oxygen (O) and sulfur(S).

Z can be a single bond, —O—, —$(CH_2)_{1-3}$—, —$O(CH_2)_{1-2}$—, —$CH_2OCH_2$—, —$(CH_2)_{1-2}O$—, —CH=$CHCH_2$—, —CH=CH—, or —$CH_2CH$=CH—; and $R_6$ can be hydrogen, alkyl, acyl, alkylsufonyl, aralkyl, substituted aralkyl, substituted alkyl, or heterocyclyl.

$R_6$ is preferably hydrogen. However, when $R_6$ is methyl or another non-hydrogen substituent, the compounds can be highly selective for inhibition of adenosine $A_{2a}$ receptors.

In certain embodiments, $R_1$ and $R_2$ can be the same or different alkyl groups (e.g., one or both can be n-propyl).

$R_3$ can be aralkyl substituted with —OH, —OMe, or -halogen; -methyl; or 3-hydroxypropyl, and Z can be a single bond.

In some embodiments, $R_3$ can be:

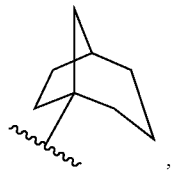

and can be unsubstituted or can be functionalized with one or more (i.e., 1, 2, 3, or more) substituents such as hydroxy, $R_5$-, or $R_5$-alkenyl. Thus, the compound can be, for example, 5-(2,6-Dioxo-1,3-dipropyl-2,3,6,7-tetrahydro-1H-purin-8-yl)-bicyclo[3.2.1]octane-1-carboxylic acid; 8-(4-Hydroxy-bicyclo[3.2.1]oct-1-yl)-1,3-dipropyl-3,7-dihydro-purine-2,6-dione; or 5-(2,6-Dioxo-1,3-dipropyl-2,3,6,7-tetrahydro-1H-purin-8-yl)-bicyclo[3.2.1]octane-2-carboxylic acid. In other embodiments, $R_3$ can be:

and can be unsubstituted or can be functionalized with one or more substituents such as hydroxy, $R_5$-alkyl, —$R_5$, $R_5$-alkenyl, alkoxycarbonyl, alkoxycarbonylalkyl, alkoxycarbonylalkenyl, hydroxyalkyl, aldehydo, alkoxyalkyl, $R_5$-alkoxy, phosphate, $R_5$-alkylcarbamoyl, and $R_5$-alkyl(alkyl)carbamoyl. Thus, the compound can be, for example, 8-(4-Hydroxy-bicyclo[2.2.2]oct-1-yl)-1,3-dipropyl-3,7-dihydro-purine-2,6-dione; 4-(2,6-Dioxo-1,3-dipropyl-2,3,6,7-tetrahydro-1H-purin-8-yl)-bicyclo[2.2.2]octane-1-carboxylic acid; 4-(2,6-Dioxo-1,3-dipropyl-2,3,6,7-tetrahydro-1H-purin-8-yl)-bicyclo[2.2.2]octane-1-carbaldehyde; 4-(2,6-Dioxo-1,3-dipropyl-2,3,6,7-tetrahydro-1H-purin-8-yl)-bicyclo[2.2.2]octane-1-carboxylic acid methyl ester; 3-[4-(2,6-Dioxo-1,3-dipropyl-2,3,6,7-tetrahydro-1H-purin-8-yl)-bicyclo[2.2.2]oct-1-yl]-acrylic acid methyl ester; 3-[4-(2,6-Dioxo-1,3-dipropyl-2,3,6,7-tetrahydro-1H-purin-8-yl)-bicyclo[2.2.2]oct-1-yl]-propionic acid methyl ester; 3-[4-(2,6-Dioxo-1,3-dipropyl-2,3,6,7-tetrahydro-1H-purin-8-yl)-bicyclo[2.2.2]oct-1-yl]-acrylic acid; 3-[4-(2,6-Dioxo-1,3-dipropyl-2,3,6,7-tetrahydro-1H-purin-8-yl)-bicyclo[2.2.2]oct-1-yl]-propionic acid; 4-[4-(2,6-Dioxo-3-dipropyl-2,3,6,7-tetrahydro-1H-purin-8-yl)-bicyclo[2.2.2]oct-1-yl]-butyric acid; Phosphoric acid mono-[4-(2,6-dioxo-1,3-dipropyl-2,3,6,7-tetrahydro-1H-purin-8-yl)-bicyclo[2.2.2]oct-1-yl]ester; {[4-(2,6-Dioxo-1,3-dipropyl-2,3,6,7-tetrahydro-1H-purin-8-yl)-bicyclo[2.2.2]octane-1-carbonyl]-methyl-amino}-acetic acid; {[4-(2,6-Dioxo-1,3-dipropyl-2,3,6,7-tetrahydro-1H-purin-8-yl)-bicyclo[2.2.2]octane-1-carbonyl]-amino}-acetic acid; 3-[4-(2,6-Dioxo-1,3-dipropyl-2,3,6,7-tetrahydro-1H-purin-8-yl)-bicyclo[2.2.2]oct-1-yloxy]-propionic acid; 3-[4-(2,6-Dioxo-1,3-dipropyl-2,3,6,7-tetrahydro-1H-purin-8-yl)-bicyclo[2.2.2]oct-1-yloxy]-propionic acid methyl ester; 3-[4-(2,6-Dioxo-1,3-dipropyl-2,3,6,7-tetrahydro-1H-purin-8-yl)-bicyclo[2.2.2]oct-1-yloxy]-propionic acid t-butyl ester; or 3-[4-(2,6-Dioxo-1,3-dipropyl-2,3,6,7-tetrahydro-1H-purin-8-yl)-bicyclo[2.2.2]oct-1-yl]-2-methyl-propionic acid.

In another embodiment, $R_3$ can be:

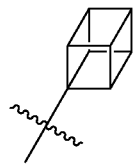

and can be unsubstituted or can be functionalized with one or more substituents such as $R_5$-alkyl, —$R_5$, $R_5$-alkenyl, alkoxycarbonyl, alkoxycarbonylalkenyl, hydroxyalkyl, aldehydo, and hydroxy. Thus, the compound can be, for example, 6-(2,6-Dioxo-1,3-dipropyl-2,3,6,7-tetrahydro-1H-purin-8-yl)-cubane-3-carboxylic acid; 8-(6-Hydroxymethyl-cuban-3-yl)-1,3-dipropyl-3,7-dihydro-purine-2,6-dione; or 3-[6-(2,6-Dioxo-1,3-dipropyl-2,3,6,7-tetrahydro-1H-purin-8-yl)-cuban-3-yl]-acrylic acid.

In yet another embodiment, $R_3$ can be:

and can be unsubstituted or can be functionalized with one or more substituents such as $R_5$-alkyl, —$R_5$, $R_5$-alkenyl, $R_5$-alkoxy, alkoxycarbonyl, alkoxycarbonylalkenyl, hydroxyalkyl, aldehydo, and hydroxy. Thus, for example, the compound can be [5-(2,6-Dioxo-1,3-dipropyl-2,3,6,7-tetrahydro-1H-purin-8-yl)-bicyclo[3.2.2]non-1-yloxy]-acetic acid; 8-(5-Hydroxy-bicyclo[3.2.2]non-1-yl)-1,3-dipropyl-3,7-dihydro-purine-2,6-dione; or 5-(2,6-Dioxo-1,3-dipropyl-2,3,6,7-tetrahydro-1H-purin-8-yl)-bicyclo[3.2.2]nonane-1-carboxylic acid.

In still another embodiment, $R_3$ can be:

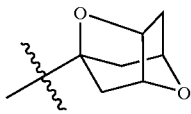

and can be unsubstituted or can be functionalized with one or more substituents such as hydroxy, $R_5$-alkoxy, $R_5$-alkenyl, alkoxycarbonyl, and carbonyl. Thus, for example, the compound can be 8-(4-Hydroxy-7-methyl-2,6-dioxa-bicyclo[3.3.1]non-1-yl)-1,3-dipropyl-3,7-dihydro-purine-2,6-dione; or [1-(2,6-Dioxo-1,3-dipropyl-2,3,6,7-tetrahydro-1H-purin-8-yl)-7-methyl-2,6-dioxa-bicyclo[3.3.1]non-4-yloxy]-acetic acid.

The compound can be, for example, in a form of an achiral compound, a racemate, an optically active compound, a pure diastereomer, a mixture of diastereomers, or a pharmacologically acceptable addition salt.

The compounds of this invention can also be modified by appending appropriate functionalities to enhance selective biological properties. Such modifications are known in the art and include those that increase biological penetration into a given biological system (e.g., blood, lymphatic system, central nervous system), increase oral availability, increase solubility to allow administration by injection, alter metabolism, and/or alter rate of excretion. Examples of these modifications include, but are not limited to, esterification with polyethylene glycols, derivatization with pivolates or fatty acid substituents, conversion to carbamates, hydroxylation of aromatic rings, and heteroatom-substitution in aromatic rings.

The invention also features a medicament composition including any of the above compounds, alone or in a combination, together with a suitable excipient. The invention also features a method of treating a subject suffering from a condition characterized by an elevated adenosine concentration and/or increased sensitivity to adenosine and/or elevated adenosine receptor number or coupling efficiency. The method includes the step of administering to the subject an amount of any of the above compounds to be effective as an adenosine receptor antagonist. The condition can be, for example, a cardiac and circulatory disorder, a degenerative disorder of the central nervous system, a respiratory disorder, a disease for which diuretic treatment is indicated, hypertension, Parkinson's disease, depression, traumatic brain damage, post-stroke neurological deficit, respiratory depression, neonatal brain trauma, dyslexia, hyperactivity, cystic fibrosis, cirrhotic ascites, neonatal apnea, renal failure, diabetes, asthma, an edematous condition, congestive heart failure, or renal dysfunction (e.g., dysfunction associated with diuretic use in congestive heart failure, or renal toxicity due to treatment with chemotherapeutic agents).

The invention also features a method of making 8-substituted xanthines. The method includes the steps of obtaining a N7,C8-dihydroxanthine (e.g., compound 10 in FIG. 1), protecting the N7 position of the xanthine (e.g., as a THP or BOM ether); deprotonating the C8 position with strong base (such as lithium diisopropylamide or n-butyl lithium) to generate an anion; trapping the anion with a carboxyl, carbonyl, aldehyde, or ketone compound; and deprotecting the protected N7 position to obtain an 8-substituted xanthine.

As used herein, an "alkyl" group is a saturated aliphatic hydrocarbon group. An alkyl group can be straight or branched, and can have, for example, from 1 to 6 carbon atoms in a chain. Examples of straight chain alkyl groups include, but are not limited to, ethyl and butyl. Examples of branched alkyl groups include, but are not limited to, isopropyl and t-butyl.

An "alkenyl" group is an aliphatic carbon group that has at least one double bond. An alkenyl group can be straight or branched, and can have, for example, from 3 to 6 carbon atoms in a chain and 1 or 2 double bonds. Examples of alkenyl groups include, but are not limited to, allyl and isoprenyl.

An "alkynyl" group is an aliphatic carbon group that has at least one triple bond. An alkynyl group can be straight or branched, and can have, for example, from 3 to 6 carbon atoms in a chain and 1 to 2 triple bonds. Examples of alkynyl groups include, but are not limited to, propargyl and butynyl.

An "aryl" group is a phenyl or naphthyl group, or a derivative thereof. A "substituted aryl" group is an aryl group that is substituted with one or more substituents such as alkyl, alkoxy, amino, nitro, carboxy, carboalkoxy, cyano, alkylamino, dialkylamino, halo, hydroxy, hydroxyalkyl, mercaptyl, alkylmercaptyl, trihaloalkyl, carboxyalkyl, sulfoxy, or carbamoyl.

An "aralkyl" group is an alkyl group that is substituted with an aryl group. An example of an aralkyl group is benzyl.

A "cycloalkyl" group is an aliphatic ring of, for example, 3 to 8 carbon atoms. Examples of cycloalkyl groups include cyclopropyl and cyclohexyl.

An "acyl" group is a straight or branched alkyl-C(=O)— group or a formyl group. Examples of acyl groups include alkanoyl groups (e.g., having from 1 to 6 carbon atoms in the alkyl group). Acetyl and pivaloyl are examples of acyl groups. Acyl groups may be substituted or unsubstituted.

A "carbamoyl" group is a group having the structure $H_2N-CO_2-$. "Alkylcarbamoyl" and "dialkylcarbamoyl" refer to carbamoyl groups in which the nitrogen has one or two alkyl groups attached in place of the hydrogens, respectively. By analogy, "arylcarbamoyl" and "arylalkylcarbamoyl" groups include an aryl group in place of one of the hydrogens and, in the latter case, an alkyl group in place of the second hydrogen.

A "carboxyl" group is a —COOH group.

An "alkoxy" group is an alkyl-O— group in which "alkyl" is as previously described.

An "alkoxyalkyl" group is an alkyl group as previously described, with a hydrogen replaced by an alkoxy group, as previously described.

A "halogen" or "halo" group is fluorine, chlorine, bromine or iodine.

A "heterocyclyl" group is a 5 to about 10 membered ring structure, in which one or more of the atoms in the ring is an element other than carbon, e.g., N, O, S. A heterocyclyl group can be aromatic or non-aromatic, i.e., can be saturated, or can be partially or fully unsaturated. Examples of heterocyclyl groups include pyridyl, imidazolyl, furanyl, thienyl, thiazolyl, tetrahydrofuranyl, tetrahydropyranyl, morpholinyl, thiomorpholinyl, indolyl, indolinyl, isoindolinyl, piperidinyl, pyrimidinyl, piperazinyl, isoxazolyl, isoxazolidinyl, tetrazolyl, and benzimidazolyl.

A "substituted heterocyclyl" group is a heterocyclyl group wherein one or more hydrogens are replaced by substituents such as alkoxy, alkylamino, dialkylamino, carbalkoxy, carbamoyl, cyano, halo, trihalomethyl, hydroxy, carbonyl, thiocarbonyl, hydroxyalkyl or nitro.

A "hydroxyalkyl" means an alkyl group substituted by a hydroxy group.

A "sulfamoyl" group has the structure $-S(O)_2NH_2$. "Alkylsulfamoyl" and "dialkylsulfamoyl" refer to sulfamoyl groups in which the nitrogen has one or two alkyl groups attached in place of the hydrogens, respectively. By analogy, "arylsulfamoyl" and "arylalkylsulfamoyl" groups include an aryl group in place of one of the hydrogens and, in the latter case, an alkyl group in place of the second hydrogen.

An "antagonist" is a molecule that binds to a receptor without activating the receptor. It competes with the endogenous ligand for this binding site and, thus, reduces the ability of the endogenous ligand to stimulate the receptor.

In the context of the present invention, a "selective antagonist" is an antagonist that binds to a specific subtype of adenosine receptor with higher affinity than to other subtypes. The antagonists of the invention can, for example, have high affinity for $A_1$ receptors or for $A_{2a}$ receptors and are selective, having (a) nanomolar binding affinity for one of these two subtypes and (b) at least 10 times, more preferably 50 times, and most preferably at least 100 times, greater affinity for one subtype than for the other.

The invention provides numerous advantages. The compounds are easily manufactured from readily available starting materials, in a relatively small number of steps. The compounds have a number of variable regions, allowing for systematic optimization. As specific antagonists, the compounds have broad medicinal utility. Since the compounds are highly potent and specific antagonists, they can (1) be used in low doses to minimize the likelihood of side effects and (2) be incorporated into numerous dosage forms including, but not limited to, pills, tablets, capsules, aerosols, suppositories, liquid formulations for ingestion or injection, dietary supplements, or topical preparations. In addition to medical applications, the antagonist compound can be used in the treatment of livestock and pet animals.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting. Other features and advantages of the invention will be apparent from the following detailed description, and from the claims.

DESCRIPTION OF THE PREFERRED EMBODIMENTS

Figure 1A:
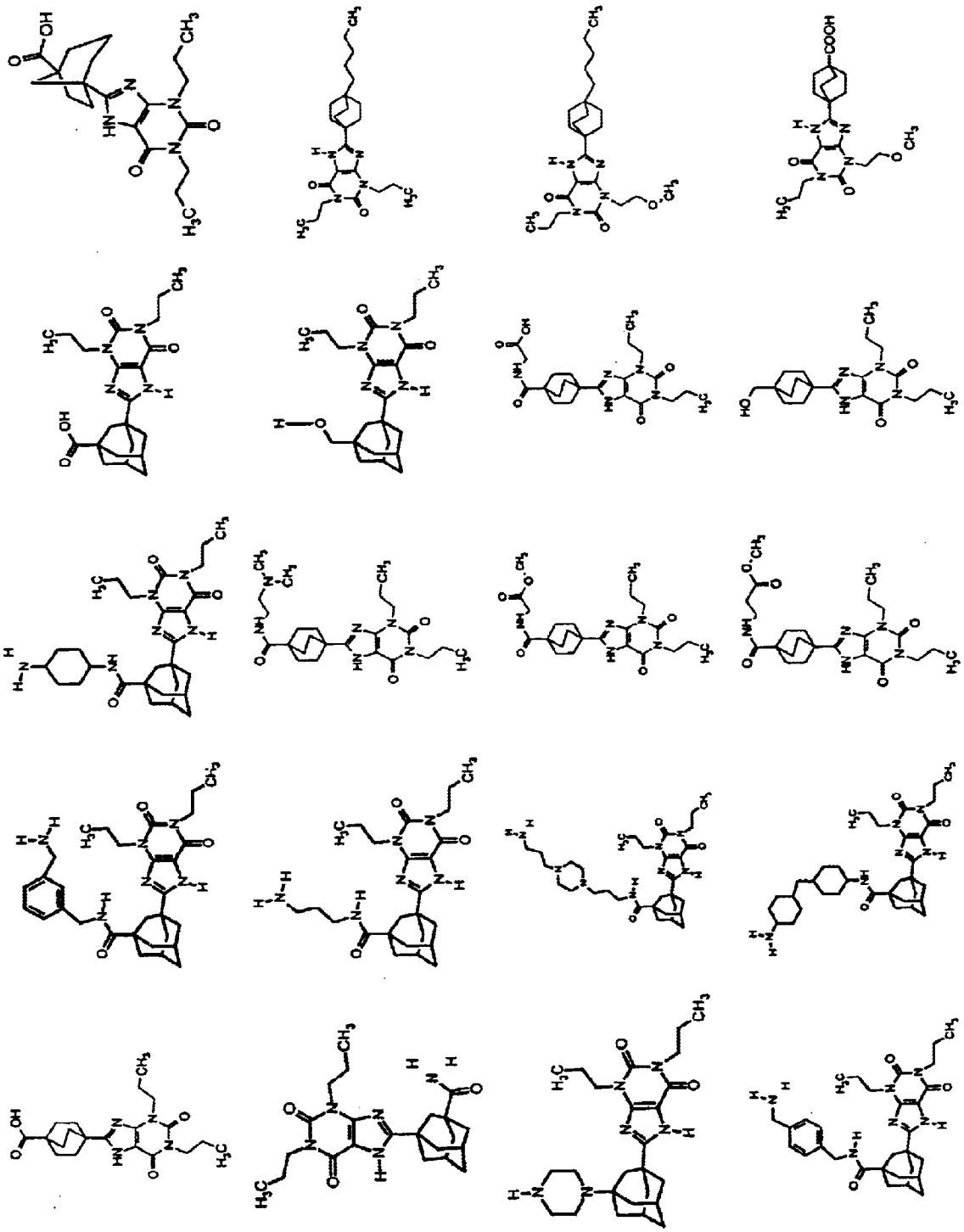
FIG. 1 is a series of illustrations of compounds of the invention.
Figure 1B:
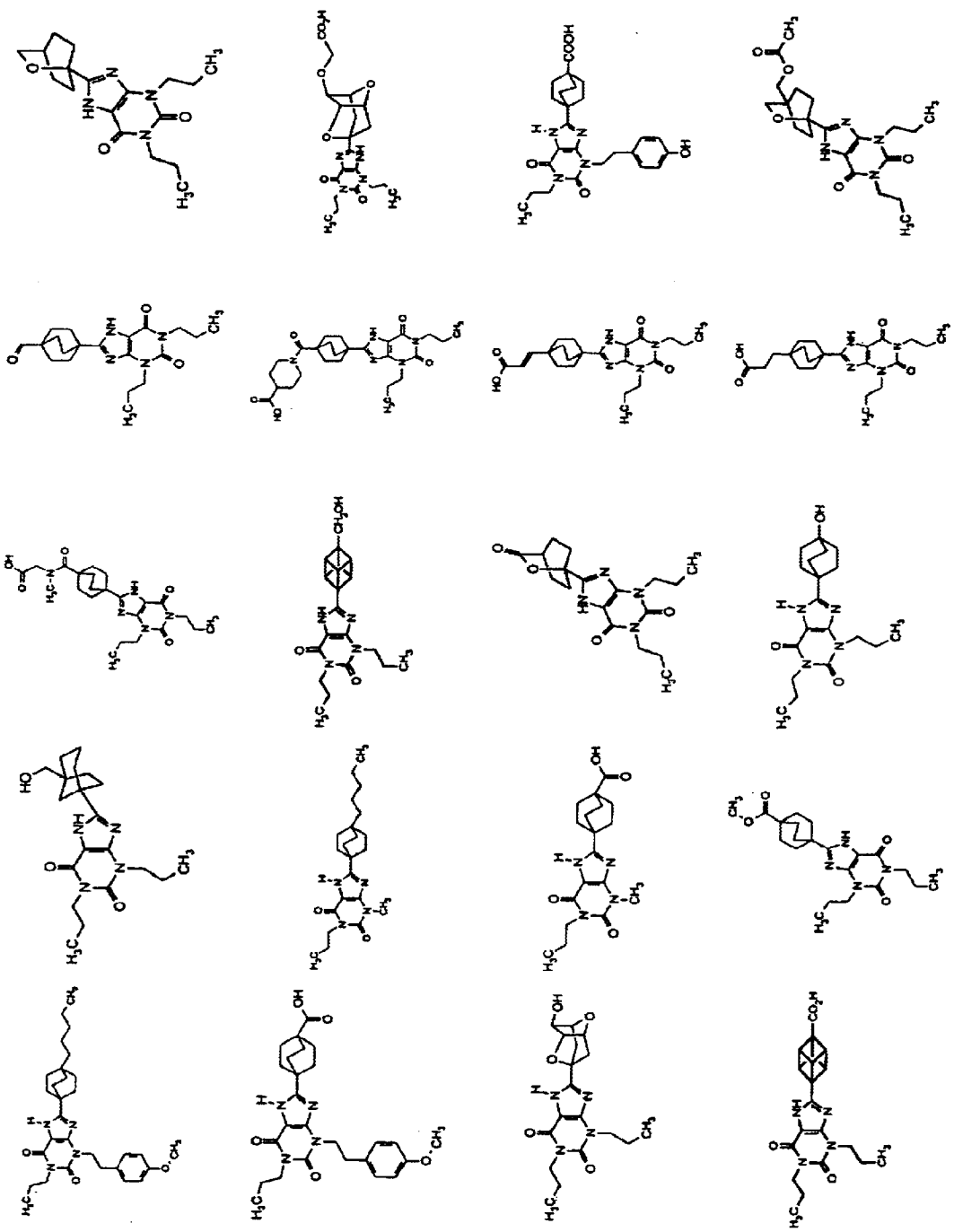
Figure 1C:
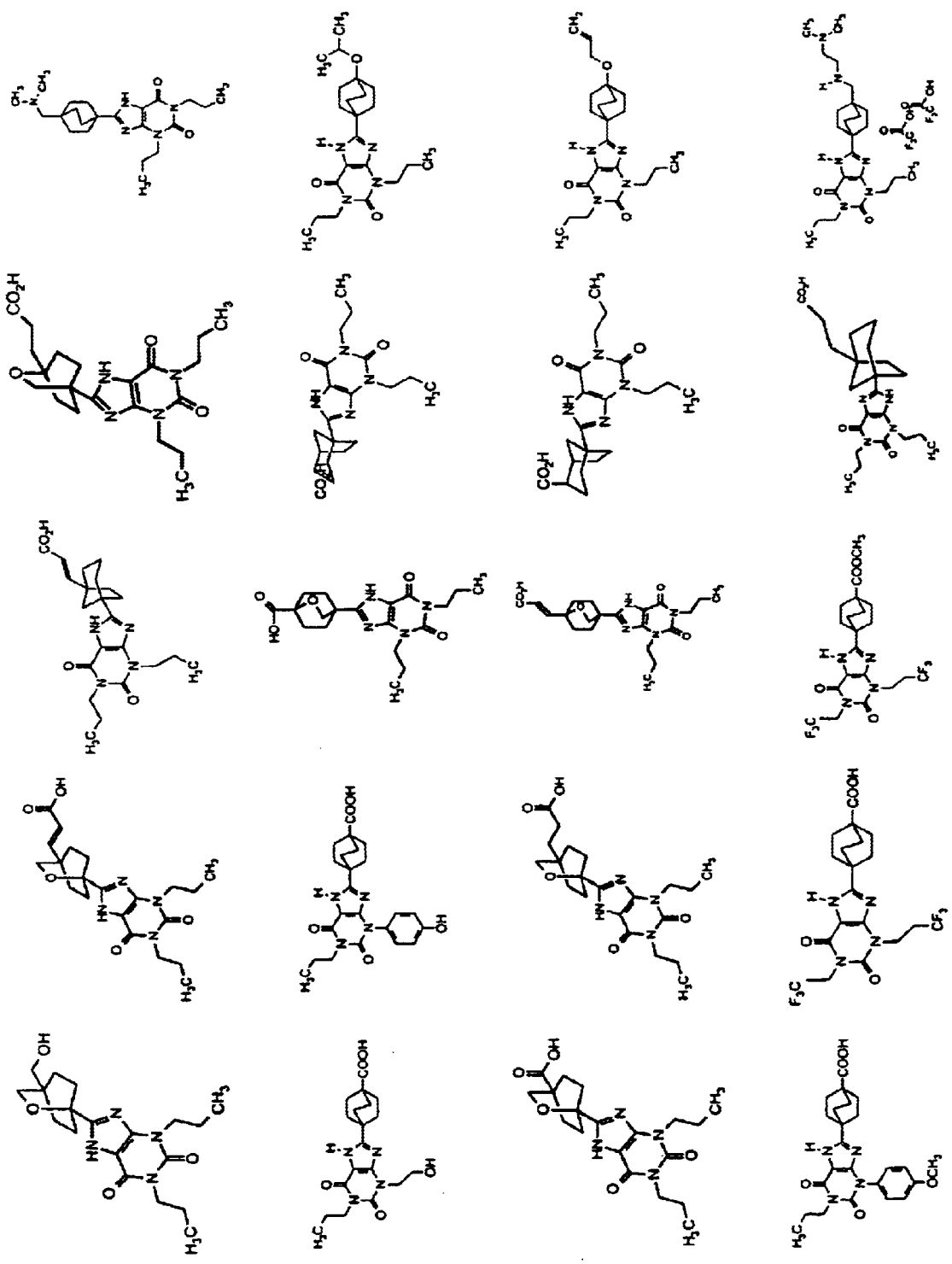
Figure 1D:
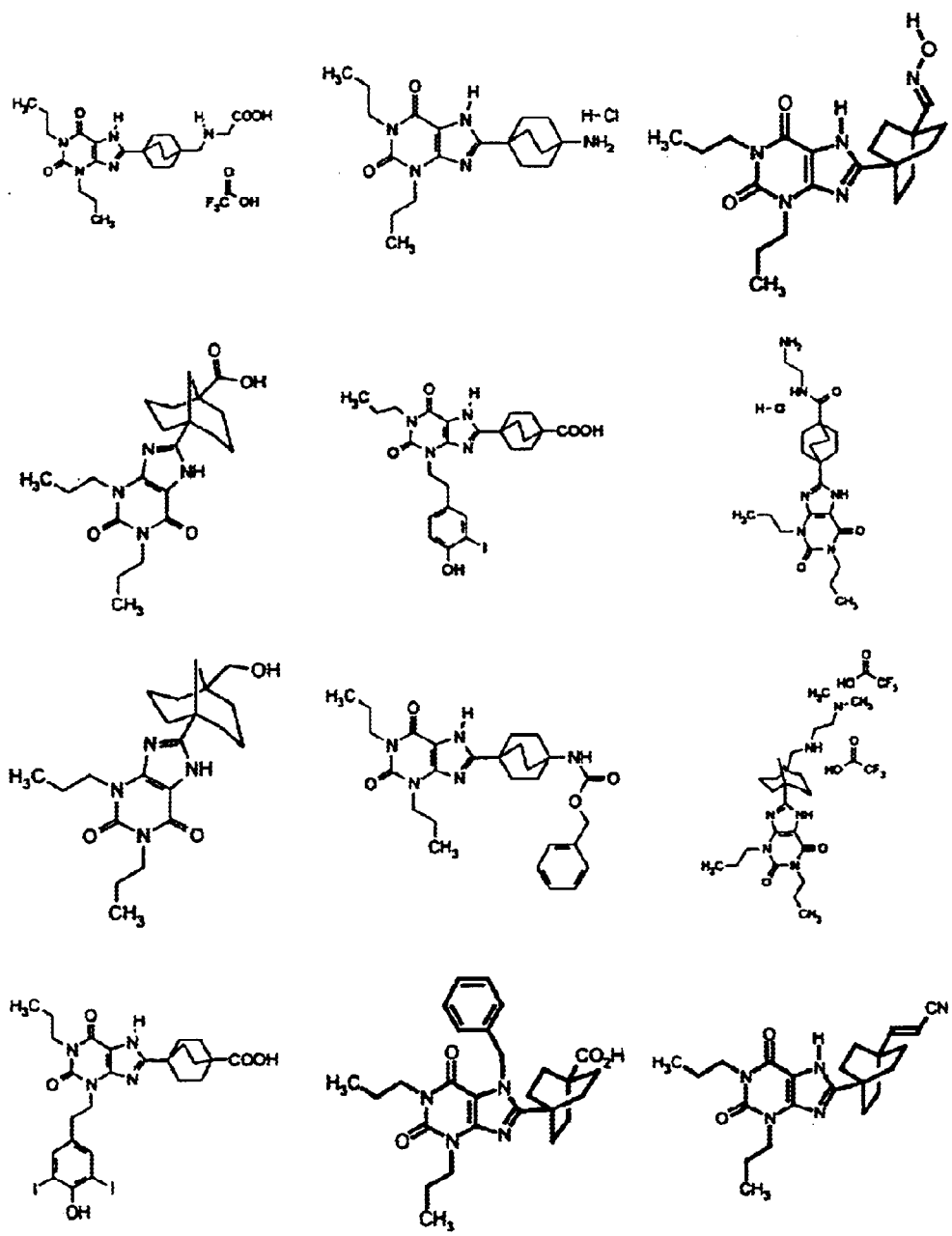
Figure 1E:
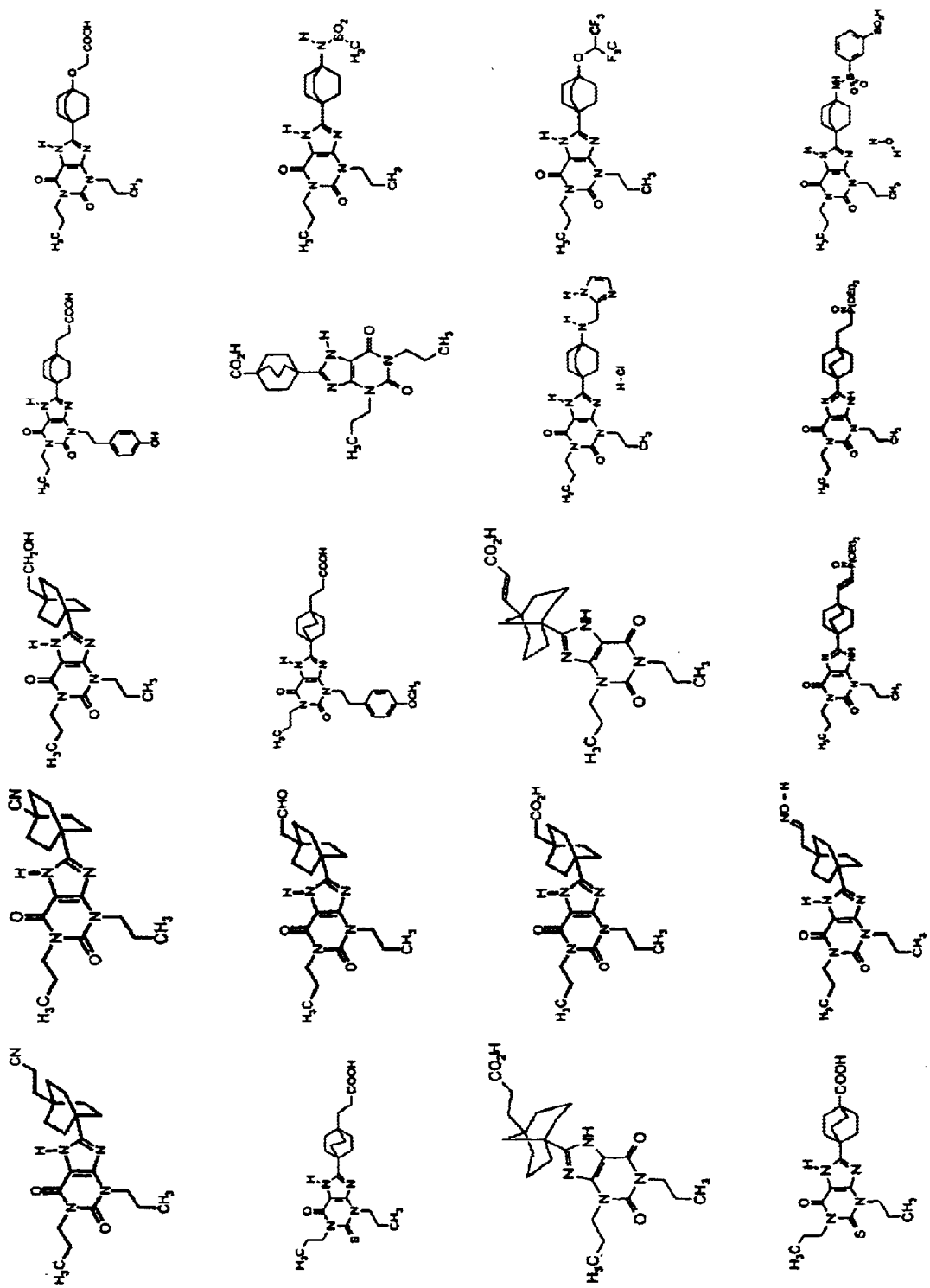
Figure 1F:
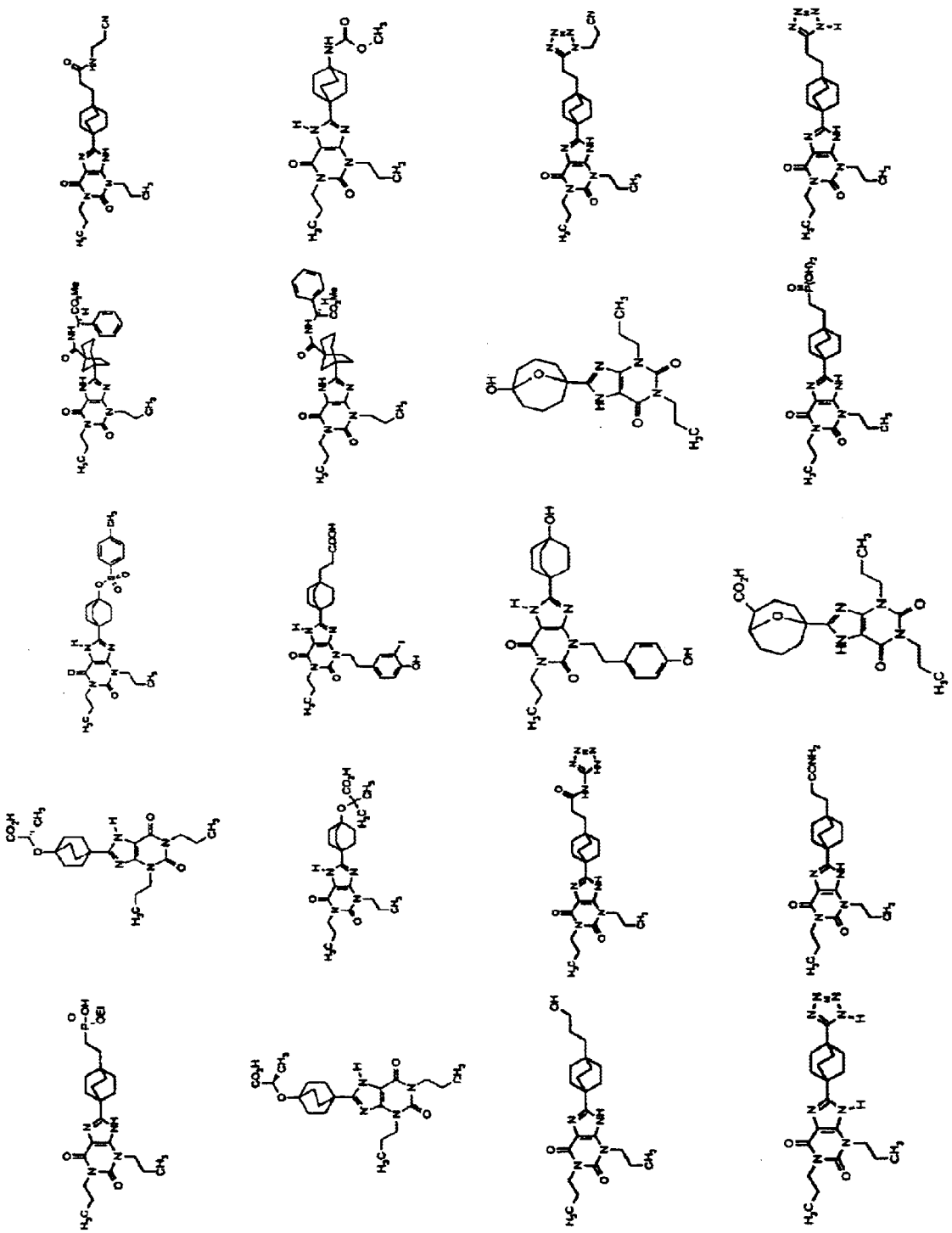
Figure 1G:
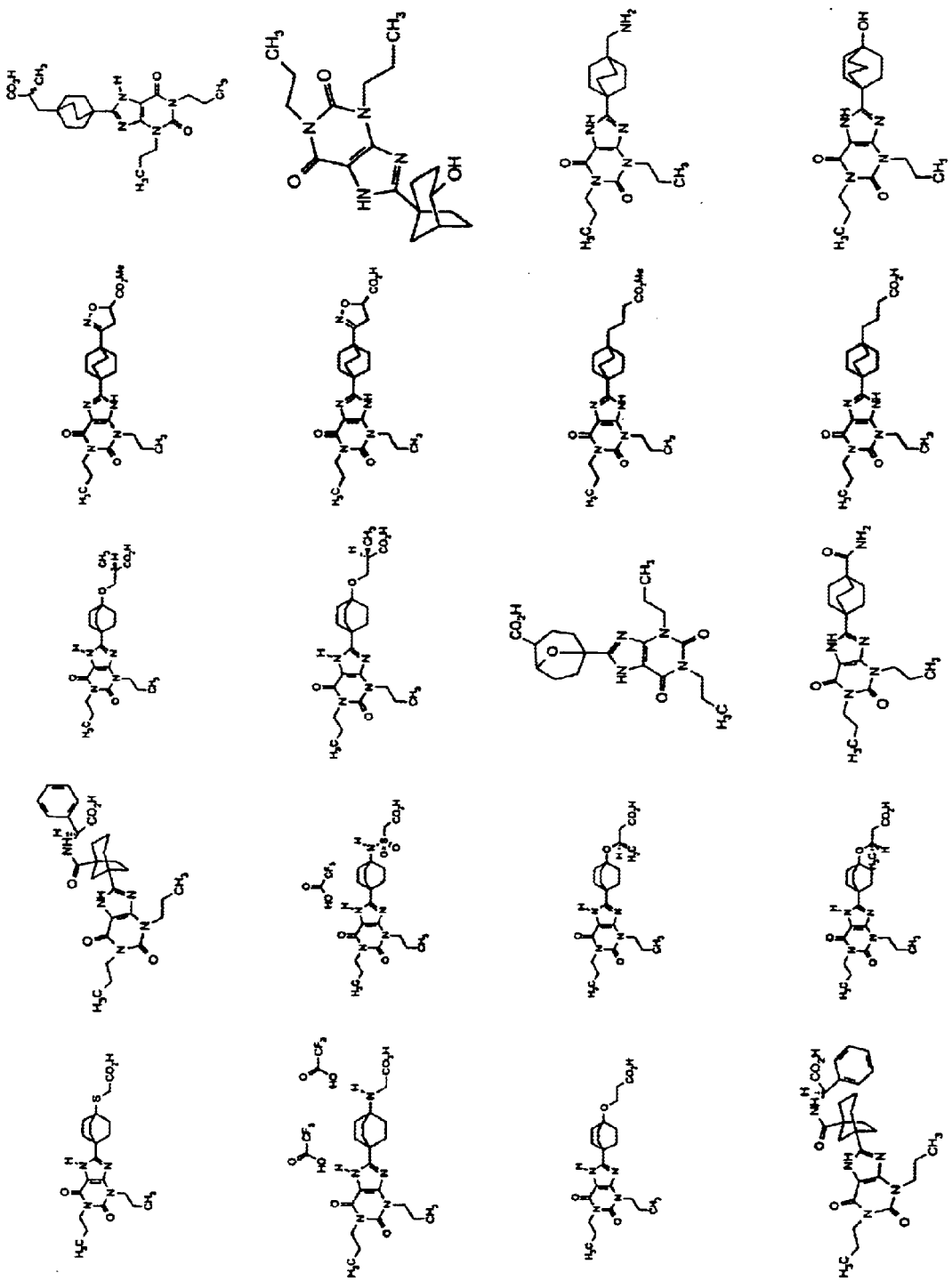
Figure 1H:
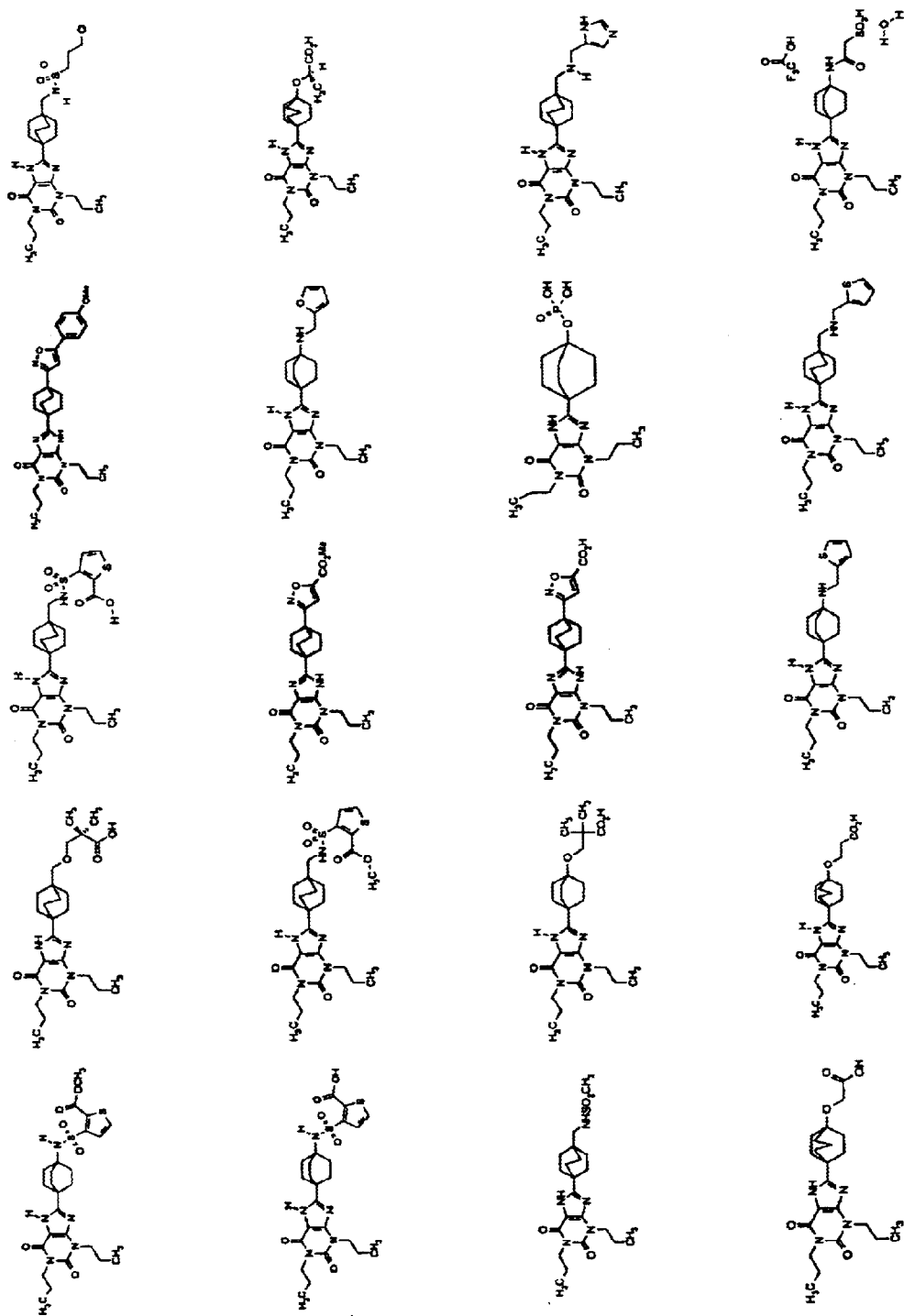
Figure 1I:
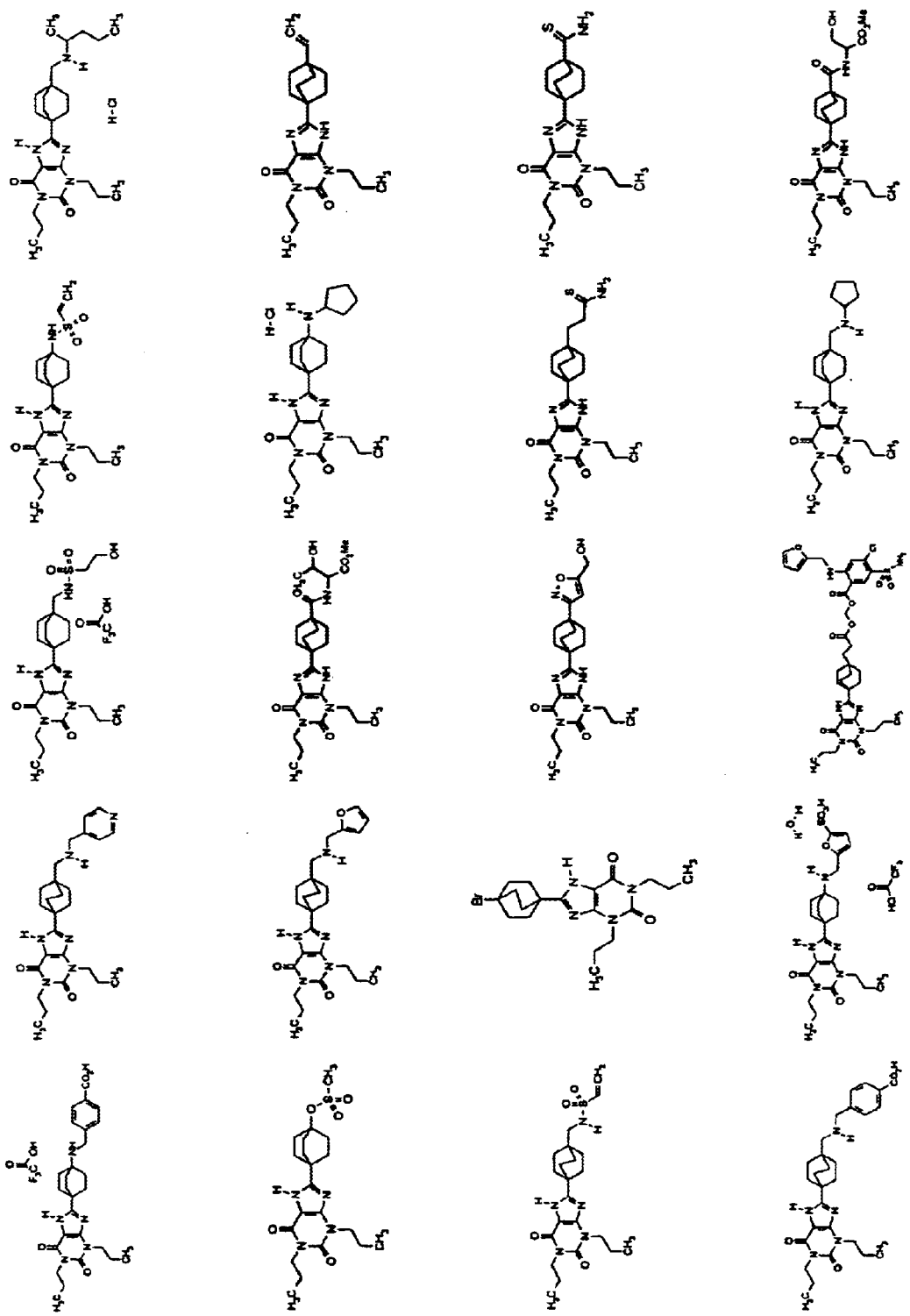
Figure 1J:
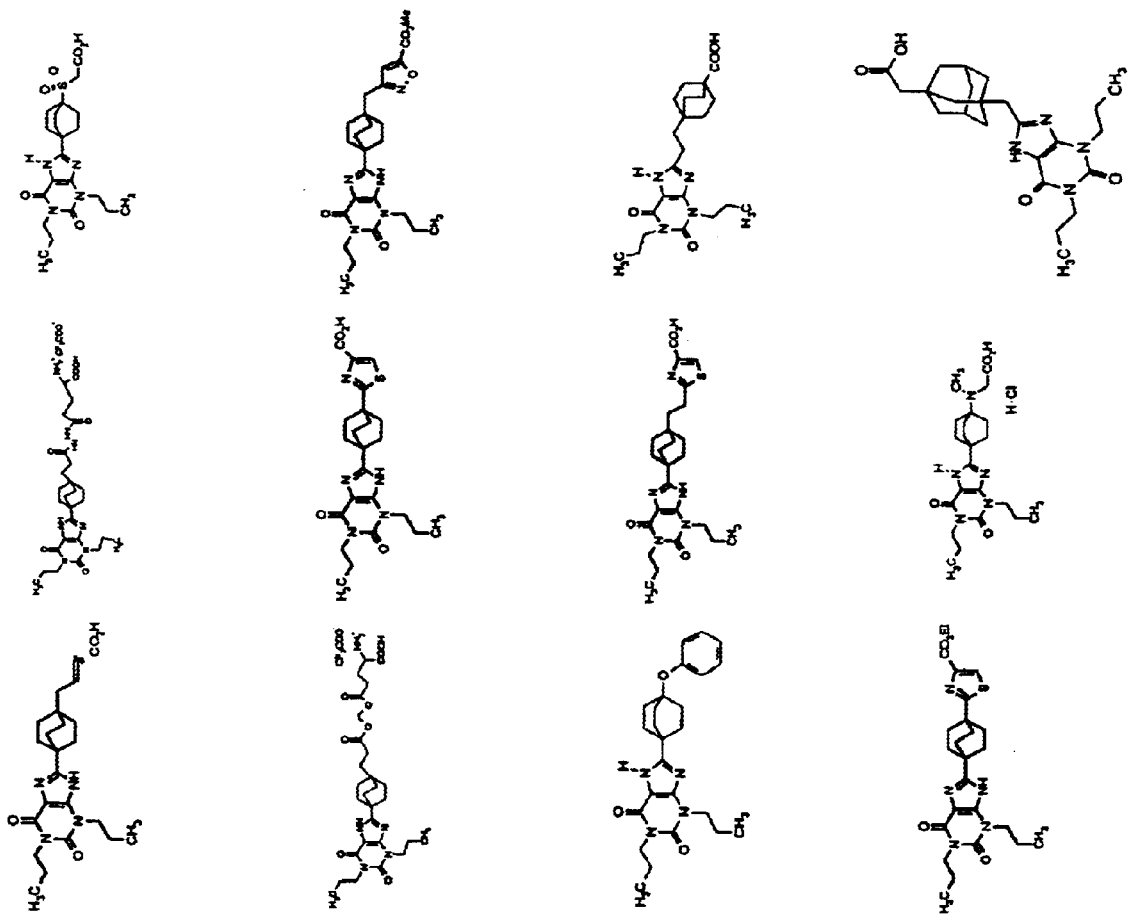

In general, the invention features highly potent and selective antagonists of the adenosine $A_1$ receptor. Selective antagonists of the adenosine $A_{2a}$ receptor are also disclosed.

Synthesis of the Adenosine Antagonist Compounds

The compounds of the invention may be prepared by a number of known methods. Two general methods are described herein. Each of them employs a common starting material, 1,3-disubstituted-5,6-diaminouracil (compound (VI)), as shown in the two schemes below. 1,3-Disubstituted-5,6-diaminouracils can be prepared by treating the corresponding symmetrically or unsymmetrically substituted urea with cyanoacetic acid, followed by nitrosation and reduction (see, e.g., *J. Org. Chem.* 16, 1879, 1951; *Can J. Chem.* 46, 3413, 1968, incorporated herein by reference). Unsymmetrically substituted xanthines can be accessed via the method of Mueller (*J. Med. Chem.* 36, 3341, 1993, incorporated herein by reference). In this method, 6-aminouracil is monoalkylated specifically at N3 of the uracil under Vorbruggen conditions. Alternatively, unsubstituted N1 or N3 position can be functionalized (e.g., alkylation) in the last stage of synthesis.

In the first general method, a 1,3-disubstituted-5,6-diaminouracil (compound (VI)) can first undergo a ring closure reaction to produce a xanthine intermediate that is unsubstituted at the 8-position. This intermediate, in turn, can couple with a precursor compound of the Z—$R_3$ moiety to produce the desired 8-substituted xanthines. Referring to scheme 1 below, the starting material 1,3-disubstituted-5,6-diaminouracil (i.e., compound (VI)) first reacts with $HC(OEt)_3$ to undergo a ring closure reaction to produce a xanthine intermediate that is unsubstituted at the 8-position (i.e., compound (A)). This intermediate, after being protected by an amino protecting group (e.g., with THP or BOM at the N7 position), further undergoes a coupling reaction, in the presence of a strong base (e.g., n-butyl-lithium (nBuLi) or lithium di-isopropyl-amide (LDA)), with a precursor compound of the Z—$R_3$ moiety (e.g., an aldehyde or a ketone) to produce an alcohol (i.e., compound (C)). The hydroxyl group of the alcohol can then be reacted to convert the alcohol to an amine, a mercaptan, an ether, a lactone (e.g., compound (E)), or other functionalized compound, by methods well known to those of ordinary skill in the art. The N7 protection can then be removed to obtain a deprotected product (i.e., compound (F)), which can be further functionalized to yield compounds of this invention. See, e.g., Examples 1–6, 51, and 52.

Scheme 1

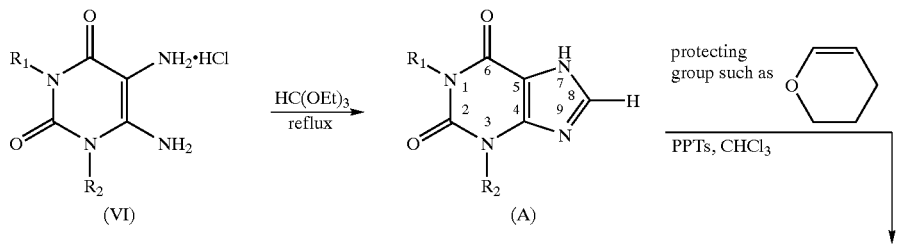

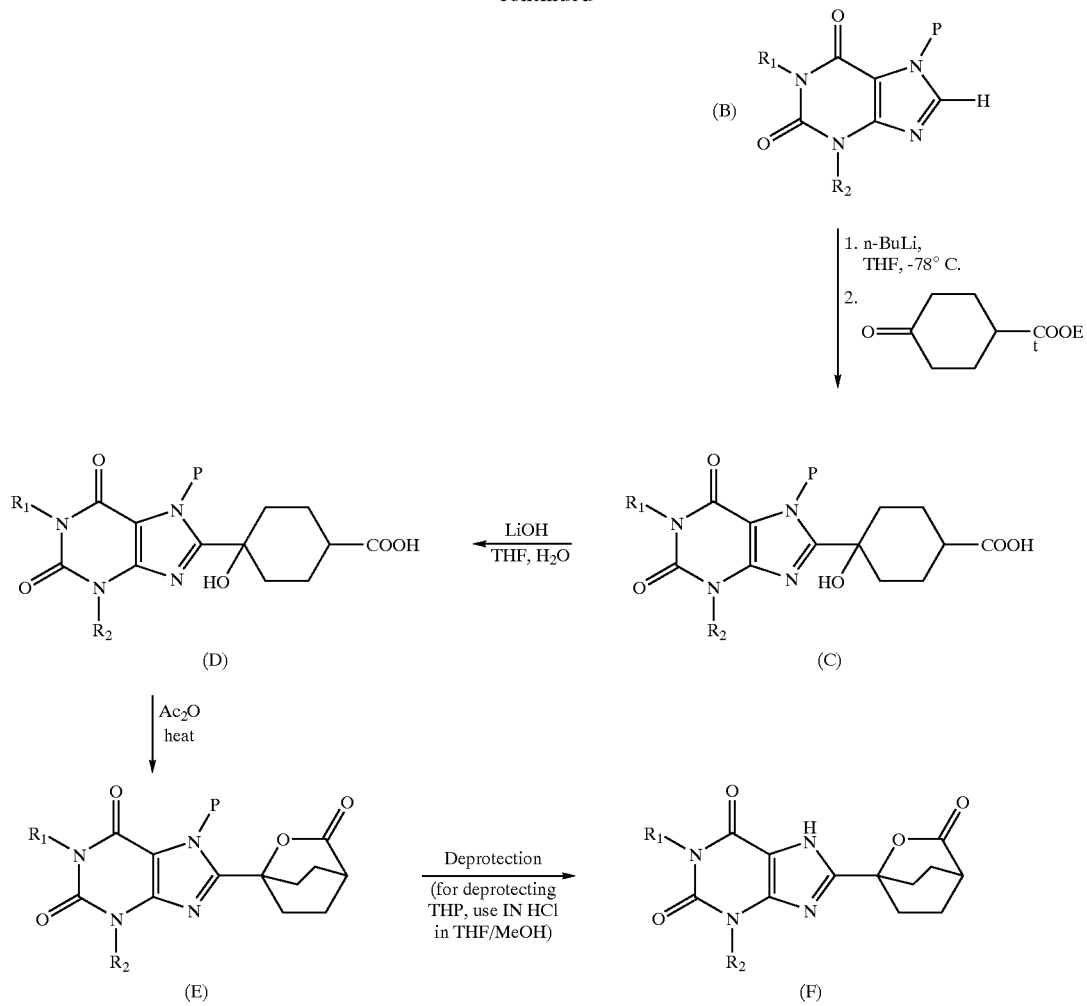

In the second general method, compounds of the invention can be prepared by reacting the starting material, a 1,3-disubstituted-5,6-diaminouracil, with a precursor compound of the Z—R₃ moiety (e.g., aldehydes or carboxylic acids or carboxylic acid chlorides) to form a 6-amide substituted uracil intermediate, which in turn, can undergo a ring closure reaction to yield to a desired xanthine compound. Referring to scheme 2 below, the starting material 1,3-disubstituted-5,6-diaminouracil (i.e., compound (VI)) first couples with a di-carboxyl/ester-substituted precursor compound of the Z—R₃ moiety, HOOC—Z—R₃—COOR$_a$ (i.e., compound (G); R$_a$ represents H, C$_{1-5}$ alkyl, or benzyl, the phenyl ring being optionally substituted with 1–3 substituents selected from the group consisting of halo, hydroxyl, or C$_{1-3}$ alkoxy) to yield a 6-amide substituted uracil intermediate (i.e., compound (H)) by reactions which are well known to one of ordinary skill in the art (e.g., by employing coupling reagents such as benzotriazol-1-yloxytris(dimethylamino)-phosphonium hexafluorophosphate (BOP), O-benzo-triazol-1-yl-N,N,N',N'-tetramethyluronium hexafluorophosphate (HBTU), or O-(7-azabenzotriazol-1-yl)-N,N,N',N'-tetramethyluronium hexafluorophosphate (HATU)). Examples of compound (G) include bicyclo[3.2.1]octane-1,5-dicarboxylic acid monomethyl ester and bicyclo[2.2.2]octane-1,4-dicarboxylic acid monoethyl ester. See, e.g., Examples 8 and 13. The uracil intermediate can then undergo a ring closure reaction in a basic condition (e.g., by employing KOH and isopropyl alcohol) to yield a xanthine compound (i.e., compound (J)), which can undergo further functionalization to produce various compounds of the invention.

Scheme 2

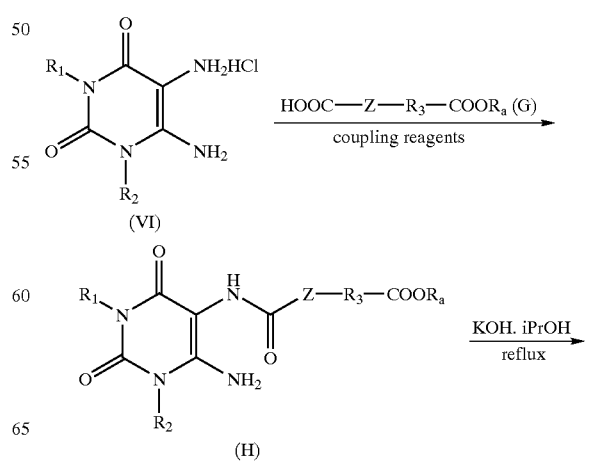

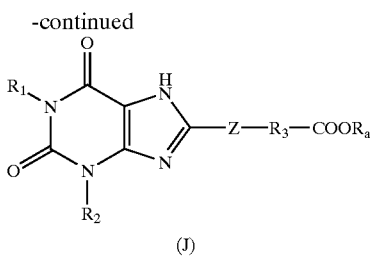

(J)

The desired aldehydes, ketones, carboxylic acids and carboxylic acid chlorides are commercially available (e.g., from Aldrich Chemical Co., Inc., Milwaukee, Wis.) or can be readily prepared from commercially available materials by well-known synthetic methods. Such synthetic methods include, but are not limited to, oxidation, reduction, hydrolysis, alkylation and Wittig homologation reactions. For references regarding the preparation of bicycloalkane carboxylic acids of the invention (e.g., compound (III), which is an example of compound (G)), see, e.g., *Aust. J. Chem.* 38, 1705, 1985; *Aust J. Chem.* 39, 2061, 1986; *J. Am. Chem. Soc.* 75, 637, 1953; *J. Am. Chem. Soc.* 86, 5183, 1964; *J. Am. Chem. Soc.* 102, 6862, 1980; *J. Org. Chem.* 46, 4795, 1981; and *J. Org. Chem.* 60, 6873, 1995.

Figure 2A:
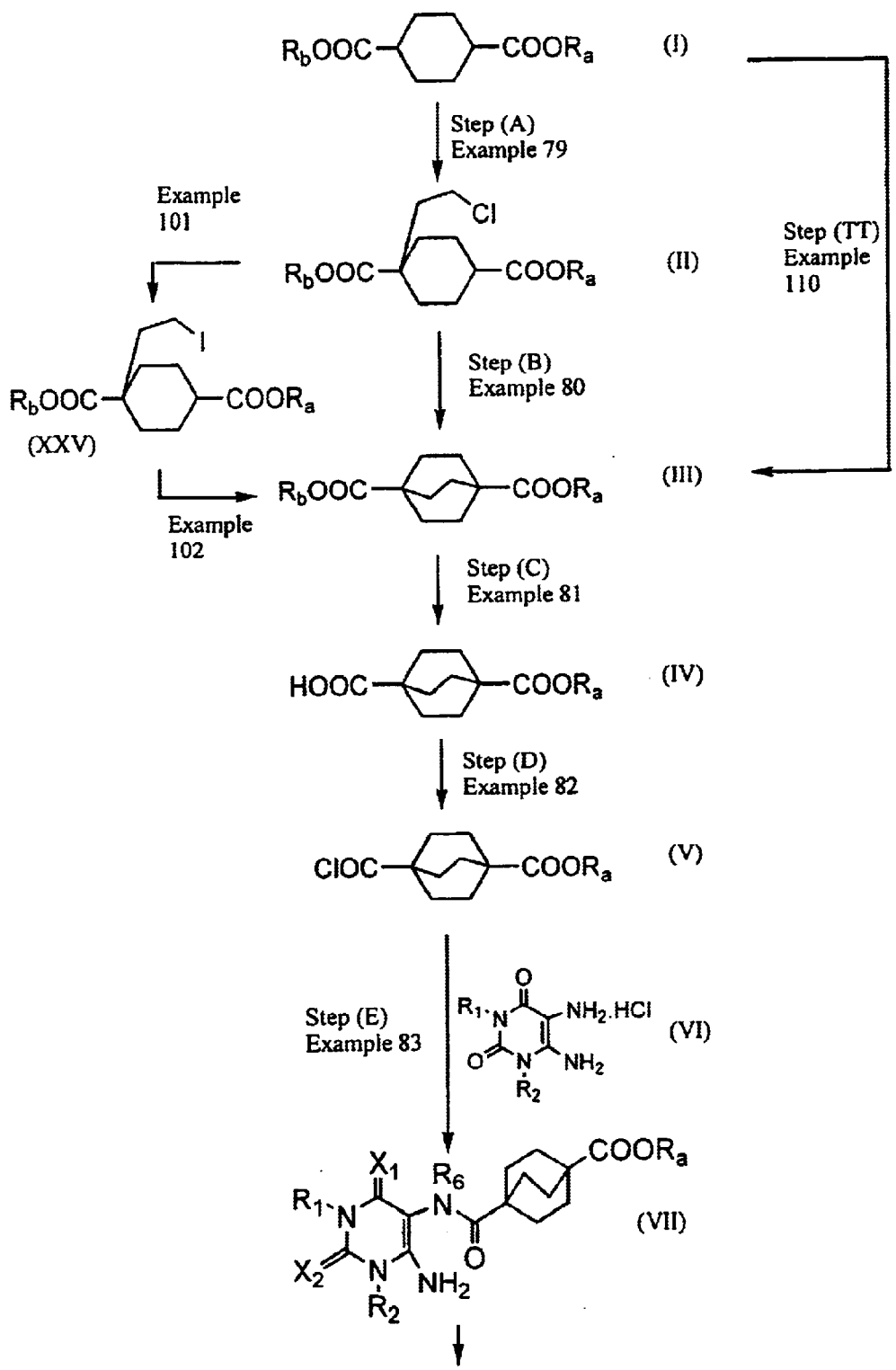
FIG. 2 is a schematic representation of the synthesis of compounds of the invention.
Figure 2B:
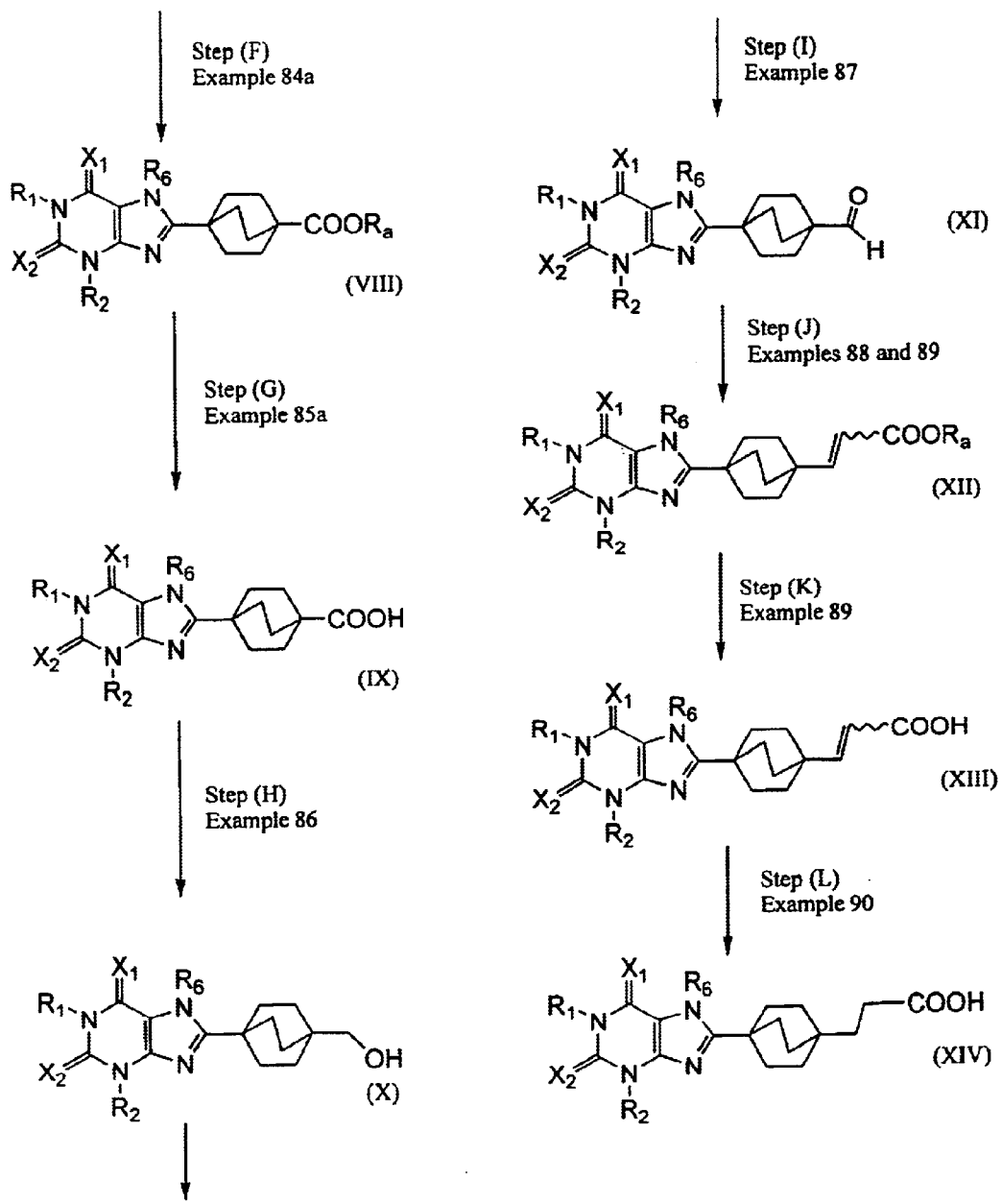

In one instance, when compound (G) is bicyclo[2.2.2]octane-1,4-dicarboxylic acid or its corresponding esters (wherein Z is a single bond and $R_3$ is bicyclo[2.2.2]octyl), there are a number of different methods for their preparation. Referring to FIG. 2, the starting material (i.e., compound (I)) is a 1-$COOR_a$-4-$COOR_b$-cyclohexane, wherein each of $R_a$ and $R_b$, independently, represents H, $C_{1-5}$ alkyl, or benzyl, the phenyl ring being optionally substituted with 1–3 substituents selected from the group consisting of halo, hydroxyl, or $C_{1-3}$ alkoxy. Preferably, $R_a$ and $R_b$ are identical and represent methyl or ethyl. Three different synthetic routes are illustrated in FIG. 2 for the tranformation of compound (I) to compound (III) (an example of compound (G)). Route (1) (i.e., steps (A) and (B)) involves transforming compound (I) to its corresponding chloroethyl-containing compound (II), which in turn, undergoes a ring closure reaction to form the corresponding 1,4-bicyclo[2.2.2]octane acid/ester (III). See Examples 79 and 80. Route (2) also involves compound (II), which is transformed to compound (III) via another intermediate, compound (XXV), the iodoethyl-containing derivative of compound (I). See Examples 101 and 102. Route (3) (i.e., step (TT)) involves the transformation of compound (I) to the 1,4-bicyclo[2.2.2]octane acid/ester (III) without isolating the intermediates, i.e., compound (II). See Example 110.

To prepare compound (II), the starting material compound (I) is treated with about 1 to about 1.5 equivalents of a strong base. Strong bases that can be employed in this reaction include lithium diisopropylamide (LDA) and lithium isopropylcyclohexylamide, with LDA being the preferred base. Typical solvents for this reaction include tetrahydrofuran (THF), dimethoxyethane, dioxane, and t-butyl methyl ether, with THF being the preferred solvent. This reaction should be performed in a temperature range of about −100° C. to about −60° C. The reaction mixture is then treated with about 1 to about 1.5 equivalents of bromochloroethane in the presence of at least four equivalents of a reagent such as 1,1,3,3-tetramethylurea (TMU), 1,3-dimethyl-3,4,5,6-tetrahydro-2(1H)-pyrimidinone (DMPU), 15-crown-5, and 12-crown-4, with TMU being preferred. This reaction can be conducted in solvents such as THF, dimethoxyethane, dioxane, or t-butyl methyl ether (with THF being the preferred solvent) and at temperature ranging from about −80° C. to about 0° C. Ring closure reaction can be performed by first treating compound (II) with about four equivalents of hexylmethylphosphoramide (HMPA), which is then followed by treatment with a strong base such as n-butyllithium and diisopropylamine (DIEA).

Turning to route (2), the chloroethyl-containing intermediate (II) can be treated with iodide to form the desired iodoethyl-containing intermediate (XXV). Examples of iodide that can be employed in this reaction include sodium iodide, potassium iodide, lithium iodide, or tetrabutylammonium iodide, with NaI being the preferred iodide. Ring closure reaction is then conducted in the presence of a suitable strong base such as LDA or lithium isopropylcyclohexylamide (with LDA being the preferred base) and reagents such as TMU or DMPU. Typical solvents for use in this reaction include THF, dimethoxyethane, dioxane, or t-butyl methyl ether (with THF being preferred). This reaction should be conducted at a temperature ranging from about −80° C. to about 25° C.

Referring to route (3) in which the starting material compound (I) is converted directly to compound (III), compound (I) is first treated with about 1 to about 1.5 equivalents of a strong base such as LDA or lithium isopropylcyclohexylamide (with LDA being the preferred base) in a suitable solvent such as THF, dimethoxyethane, dioxane, t-butyl methyl ether (with THF being the preferred solvent). The temperature of the reaction should range from about −100° C. to about −60° C. The resulting reaction mixture is then treated with less than one equivalent of bromochloroethane in the presence of at least four equivalents of HMPA at a temperature ranging from about −80° C. to about 25° C. The resulting reaction mixture is further contacted with about 1 to about 1.5 equivalents of a strong base such as LDA or lithium isopropylcyclohexylamide (with LDA being the preferred base) and at least four equivalents of HMPA in a suitable solvent such as THF, dimethoxyethane, dioxane, or t-butyl methyl ether (with THF being the preferred solvent). This reaction should be conducted at a temperature ranging from about −100° C. to about −60° C. Note that no isolation of intermediates are needed in route (3).

There are many methods to further functionalize compound (J), which contains a carboxylic acid or ester attached to the $R_3$ moiety. For example, compound (J) can be converted to the corresponding acrylic acid derivative. One way is to first hydrolyze the ester group of compound (J) (provided that $R_a$ is not H) to give the corresponding carboxylic acid, reduce the carboxylic acid to the corresponding alcohol, oxidize the alcohol to the corresponding aldehyde, and then perform a Wadsworth-Homer-Emmons or Witting reaction to form the corresponding acrylic acid derivative. See, e.g., Examples 5, 6, 15, 16, and 17. Compound (J) can also be transformed directly to its corresponding alcohol (see, e.g., Example 4). A different variation is to transform compound (J) directly to its corresponding aldehyde. A further variation, is to transform an ester-containing compound (J) to its corresponding carboxylic acid, and then directly to the aldehyde. Alternatively, one can functionalize the precursor compound of the Z—$R_3$ moiety before coupling to the or 1,3-disubstituted-8-unsubstituted xanthine in scheme 1 or the 1,3-disubstituted-5,6-diaminouracil in scheme 2. Further, compounds of this invention can be prepared on solid support (e.g., Wang resin). See Example 36.

Figure 3:
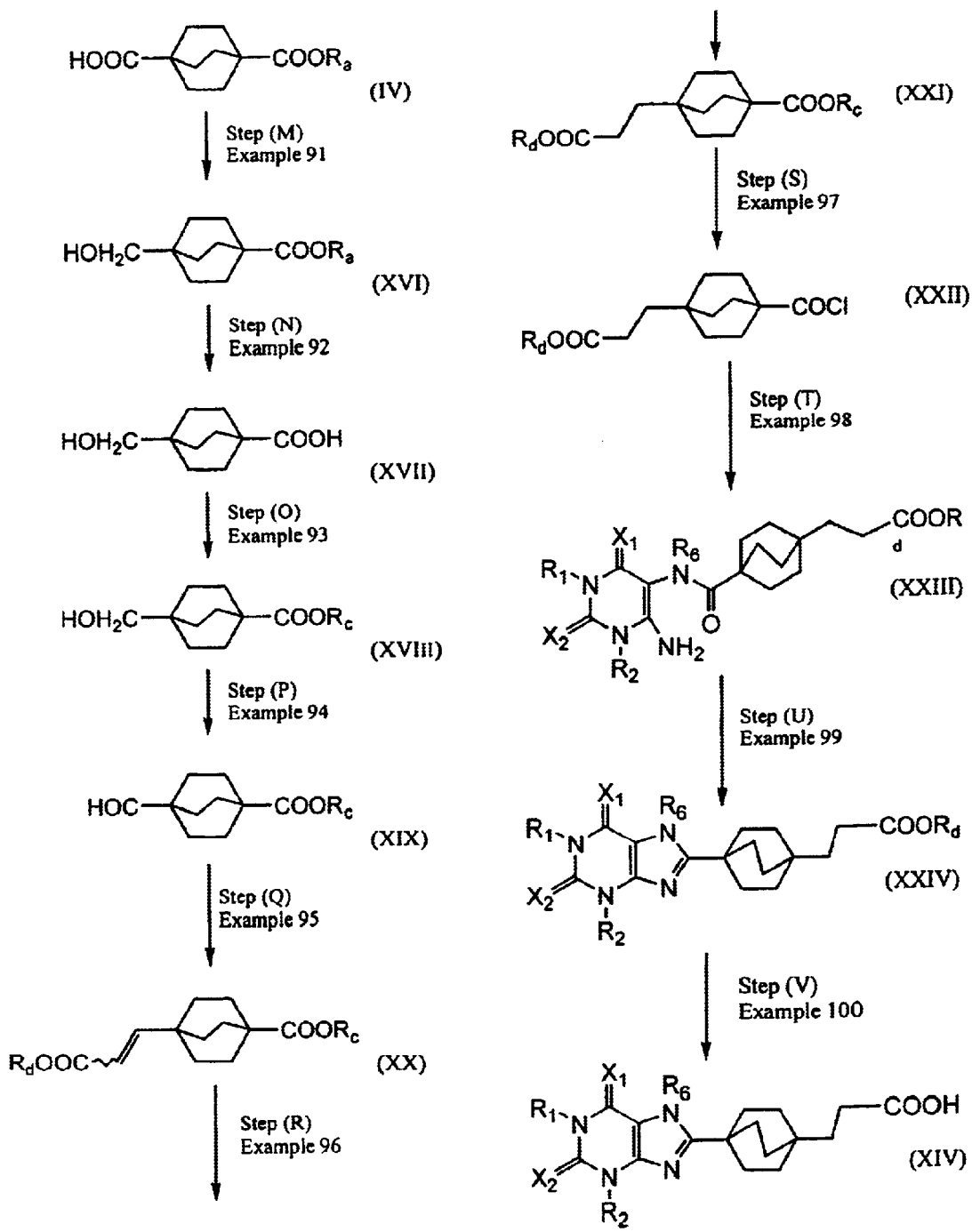
FIG. 3 is a schematic representation of an alternative route of the synthesis of compounds of the invention.

FIG. 3 discloses an alternative process to prepare compound (XIV) starting with compound (IV). The process illustrated in FIG. 2 employs similar chemistry as illustrated in FIG. 2 but first prepares the propionic acid side chain on the bicyclo[2.2.2]octyl moiety and then adds on the 1,3-disubstituted uracil moiety followed by cyclization to give the desired compound (XIV). With regard to compound (XX), $R_3$ and $R_4$ must be chemically different in their reactivity (e.g., methyl and benzyl).

Figure 4A:
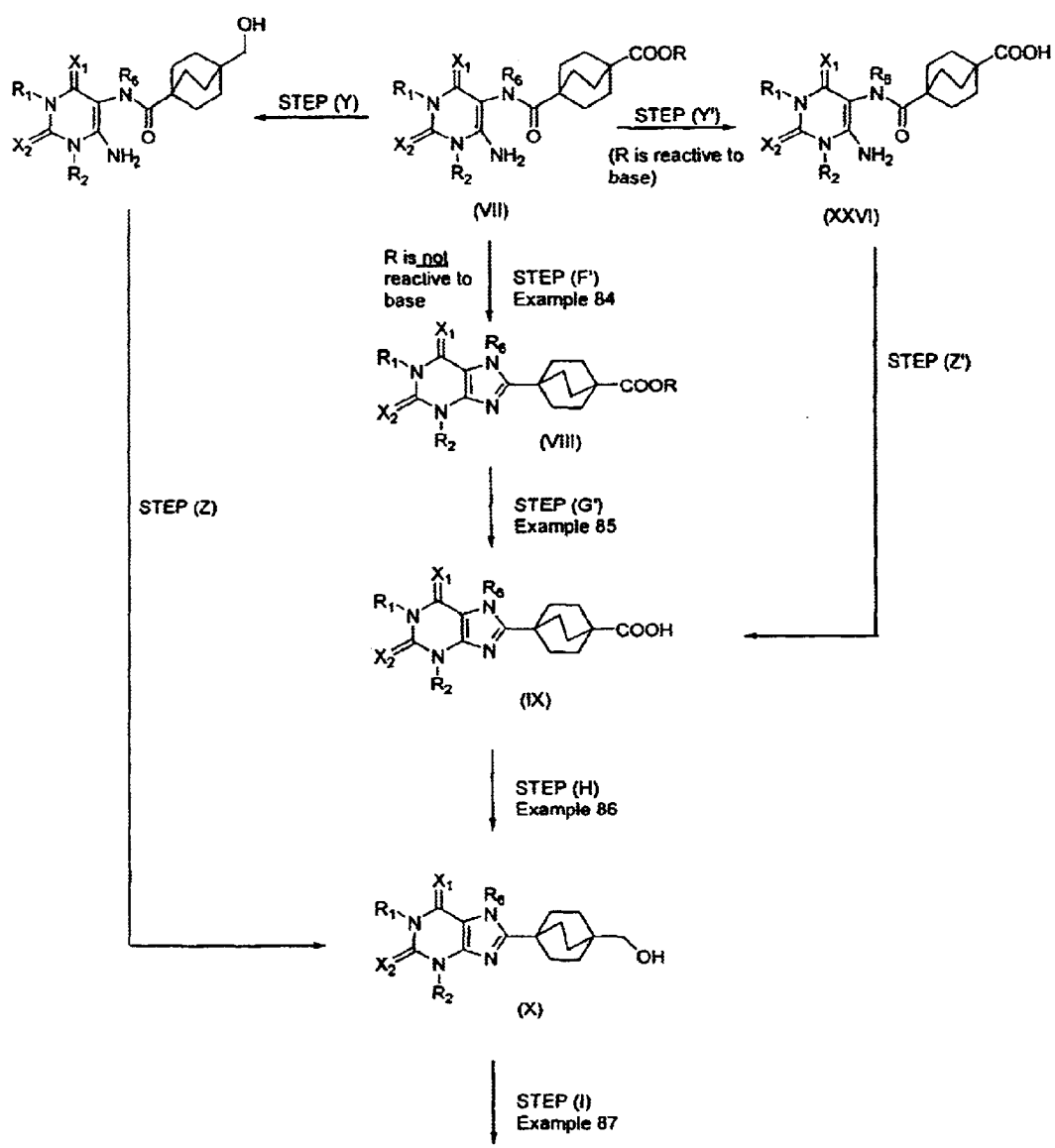
FIG. 4 is a schematic representation of the transformation of compound (VII) to the corresponding olefin (XII) via an alcohol (X).
Figure 4B:
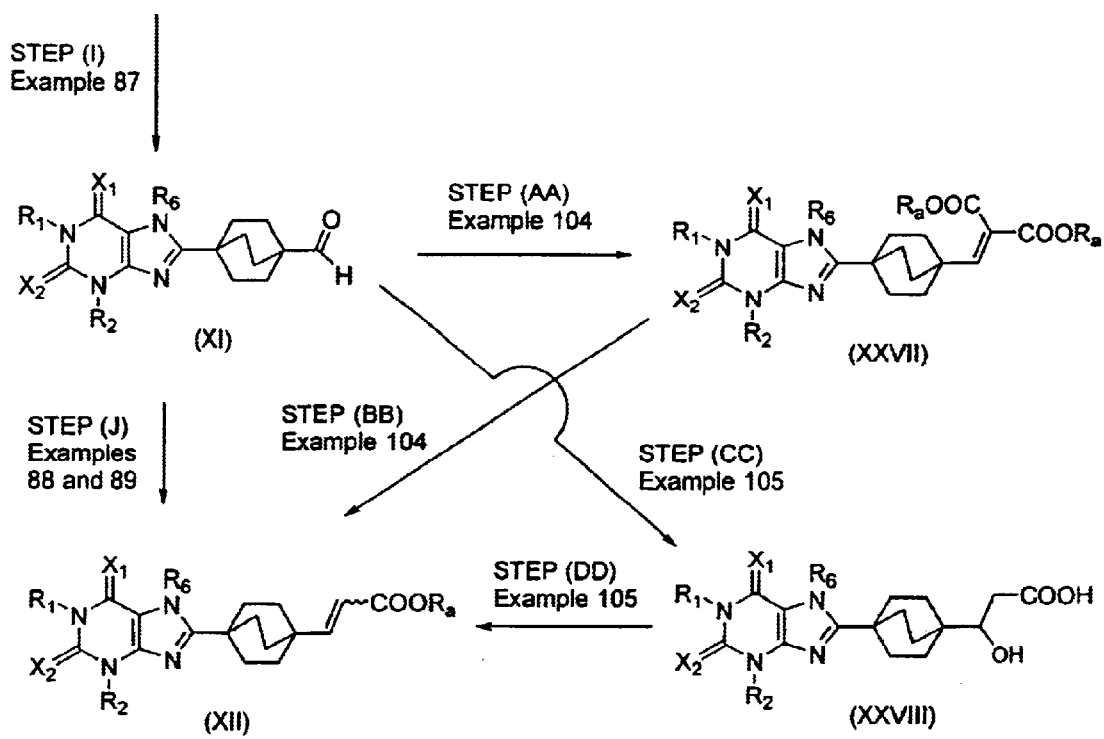

FIG. 4 discloses an alternative processes for the transformation of compound (VII) to the corresponding alcohol (X) and the subsequent transformation of the alcohol (X) to the olefin (XII). Steps (F') thru (H) are ring closure followed by soponification of the ester (VIII) to the acid (IX) followed by reduction to the alcohol (X), see Examples 84, 85, and 86. Alternatively, compound (VII) can undergo reduction (step (Y), see Example 103) and cyclization reactions to produce compound (X) (step (Z), see, e.g., Example 84a). A further alternative way involves soponification and cyclization of compound (VII) to produce compound (IX) (steps (Y') and (Z')). These reactions are well known to those skilled in the art. See, e.g., Examples 85a and 84a. Steps (I) thru (DD) disclose alterntive processes for the transformation of the alcohol (X) to the corresponding olefin (XII). Specifically, steps (J), (AA) and (CC) (see Examples 89, 104, and 105) are alternative ways of transforming the one carbon aldehyde of compound (XI) to the acrylic acid/ester-containing moiety by means known to those skilled in the art.

Figure 5:
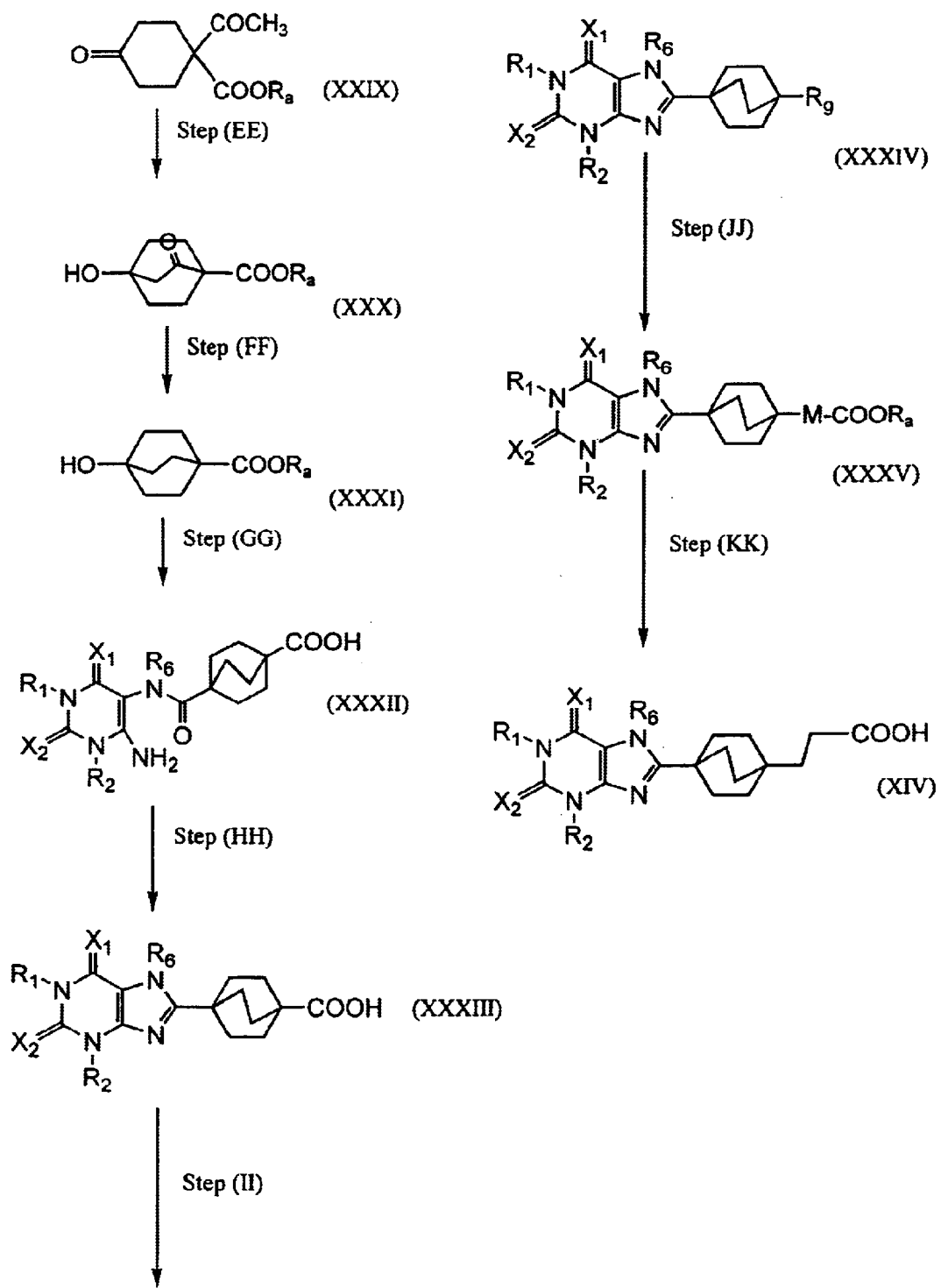
FIG. 5 is a schematic representation of yet another route of the synthesis of compounds of the invention.

Referring to FIG. 5, compounds (XXIX) and (XXX) have been previously described in the literature (Grob, C. A., Rich, R. *Helv. Chim. Acta.* 1979, 62, 2802; Ahmed, S. A., Hickmott, P. W. *J. Chem. Soc. Perkin Trans. I,* 1979, 2180) (i.e., Steps (EE) and (FF)). Compound (XXX) can be converted to compound (XXXI) by well-known methods. For example, compound (XXX) may be reduced directly by means of a Wolff-Kishner or Clemmenson reduction. Alternatively, the ketone functionality of compound (XXX) may first be converted to a dithioketal derivative, such as for example, a 1,3-dithiane, 1,3-dithiolane or 1,3-dialkylthioketal. This intermediate, would, in turn, be desulfurized by Raney-Ni. Functional group manipulations of this sort are common and are known to one of average skill in the art. The following two steps, i.e., steps (GG) and (HH), represent examples of coupling a 1,3-disubstituted-5, 6-diaminouracil with a carboxylic acid followed by base-mediated ring closure. In Step (II), the tertiary hydroxyl is converted to its corresponding bromide, iodide or trifluoromethanesulfonate by exposure to $PBr_3$, TMSBr, TMSI, KI and $H_3PO_4$, or trifluoromethanesulfonic anhydride in the presence of a non-nucleophilic base. Compound (XXXV) would then be formed by treatment of (XXXIV) with a catalyst derived from a palladium salt ($Pd(OAc)_2$, $PdCl_2$, $Pd(O_2CCF_3)$, etc.) and a phosphine ligand ($PPh_3$, $P(o-tolyl)_2$, etc.) followed by treatment with an olefin (such as methyl acrylate, methylpropiolate, etc.). Hydrogenation of compound (XXXV) followed by conversion of the ester to the corresponding acid would provide compound (XIV). Alternatively, the ester could first be converted to the acid and the hydrogenation then performed to also generate (XIV).

Figure 6:
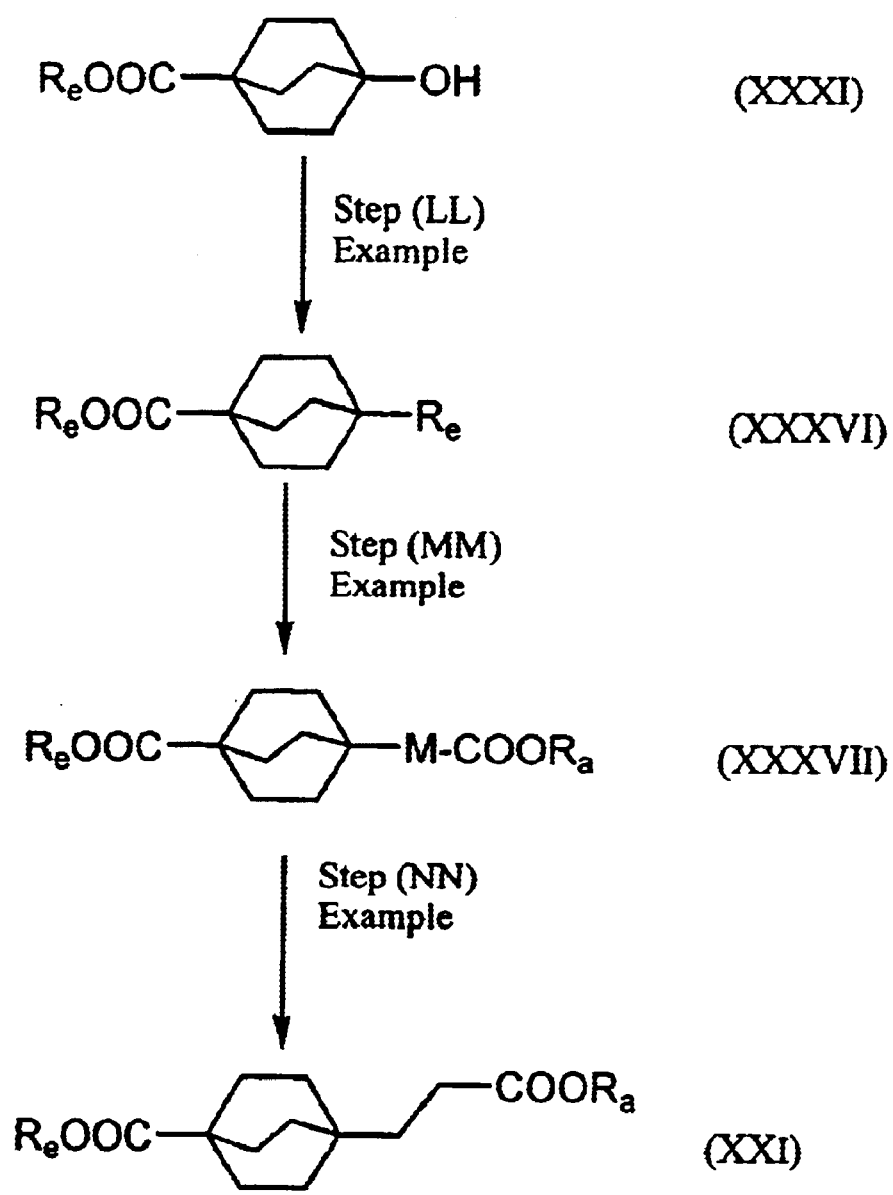
FIG. 6 is a schematic representation of the synthesis of compound (XXI), which is the starting material used in the reaction shown in FIG. 3.

FIG. 6 discloses a process to prepare acid (compound (XXI)) which is the starting material for FIG. 3. In step (LL), treatment of compound (XXXI) with trifluoromethane-sulfonic anhydride in the presence of a base such as pyridine affords XXXVI ($R_g$=OTf). The next step, i.e., step (MM), involves treating compound (XXXVI) ($R_g$=OTf) with a catalyst derived from a palladium salt ($Pd(OAc)_2$, $PdCl_2$, $Pd(O_2CCF_3)_2$, etc.) and a phosphine ligand ($PPh_3$, $P(o-tolyl)_3$, etc.), which is then followed by exposure to an olefin (methyl acrylate, methyl propiolate, etc.) to afford compound (XXXVII) (wherein M=—C≡C— or —CH=CH—). In step (NN), compound (XXXVII) undergoes hydrogenation with palladium on carbon under an atmosphere of hydrogen to yield compound (XXI).

Figure 7:
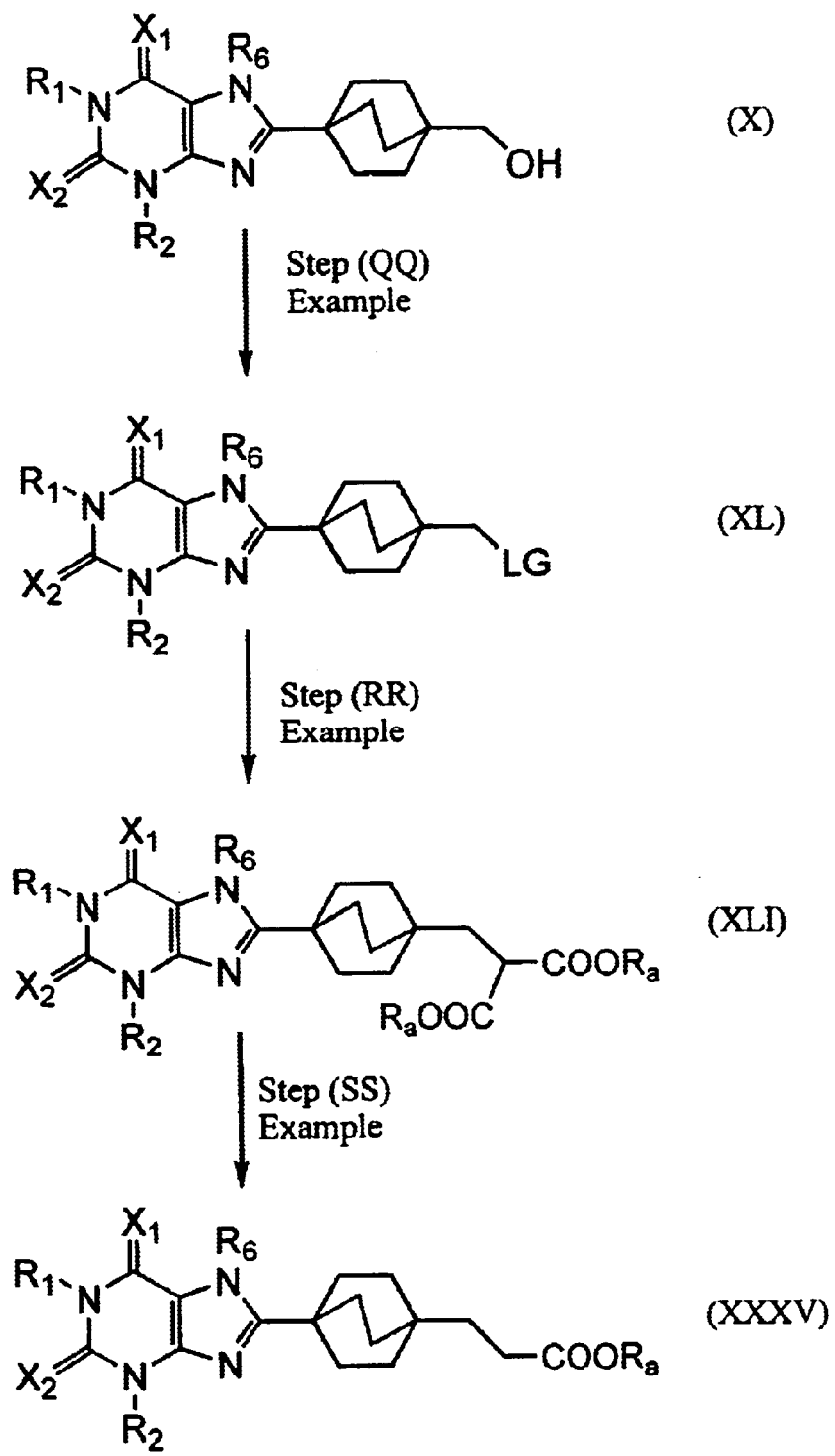
FIG. 7 is a schematic representation of an alternative route of the synthesis of compound (XXI).

Turning to FIG. 7, compound (X) can be converted to compound (XL) containing a leaving group (LG) such as, e.g., halo (Cl, Br, or I), mesylate, nosylate, tosylate. and trifluoromethanesulfonate. The leaving group (LG) can then be displaced by a malonic ester, such as, e.g., dimethyl malonate, in the presence of a base, such as, e.g., methoxide. The leaving group (LG) might also be displaced by Meldrum's acid, in the presence of a base such as methoxide. Conversion of the esters or the cyclic anhydride, in the case of Meldrum's acid, to the corresponding acids followed by decarboxylation provides compound (XXXV).

Figure 8:
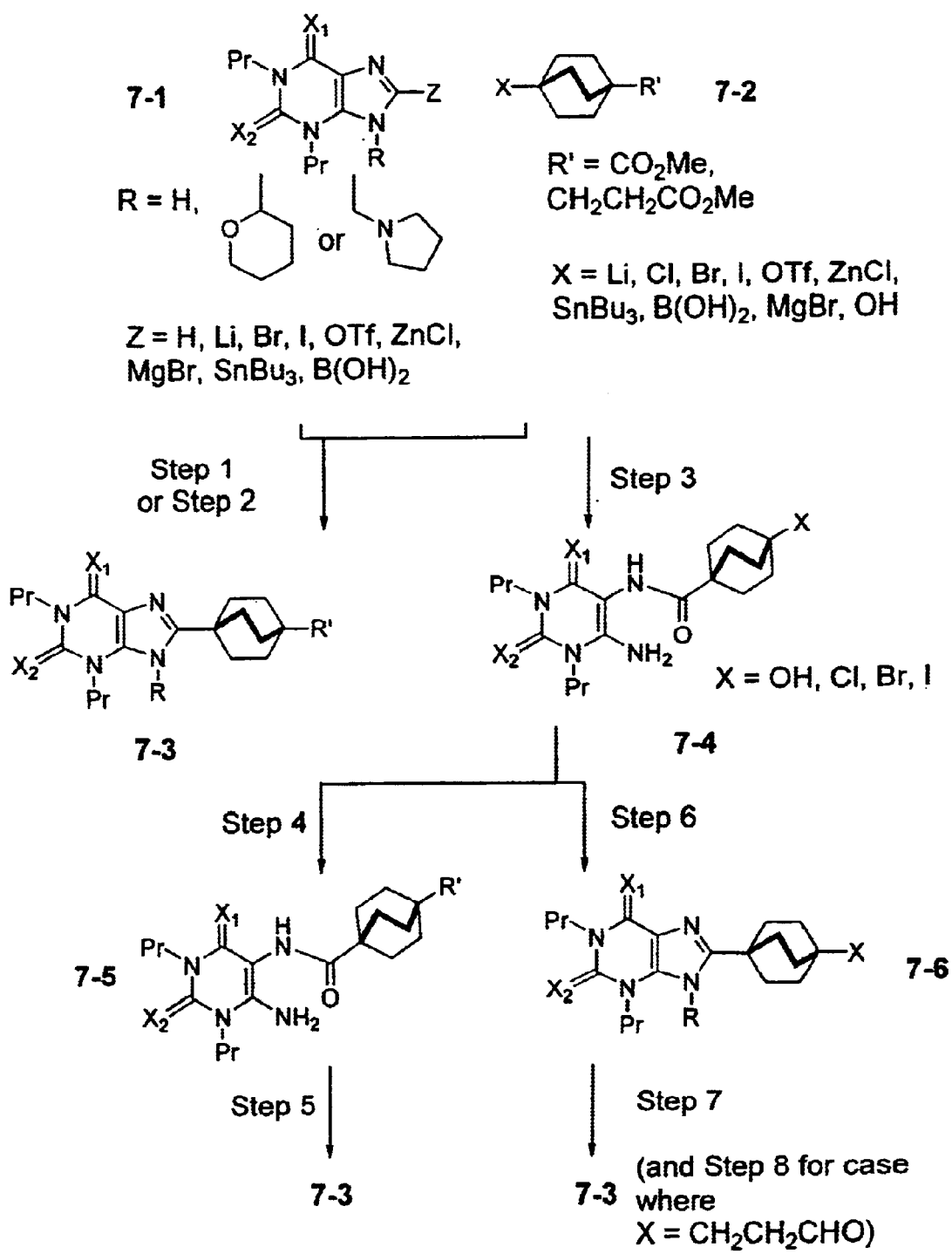
FIG. 8 is a schematic representation of the synthesis of various compounds of the invention.

FIG. 8 discloses an overview of the synthetic methods that can be employed to produce various compounds of the invention. In step 1, treatment of compound 7-1 (Z=Br, I or OTf, and R=H, tetrahydropyran-2-yl- or 1-pyrollidinylmethyl) with a catalyst derived from a palladium salt ($Pd(OAc)_2$, $PdCl_2$, $Pd(O_2CCF_3)_2$, etc.) and a phosphine ligand ($PPh_3$, $P(o-tolyl)_3$, etc.) is followed by exposure to compound 7-2 (X=Li, ZnCl, MgBr, $SnBu_3$, $B(OH)_2$ and R'=$CO_2H$, $CO_2Me$, $CO_2Et$, $CCCO_2Me$, $CCCO_2Et$, CH=$CHCO_2Me$, CH=$CHCO_2Et$, $CH_2CH_2CO_2Me$, $CH_2CH_2CO_2Et$) to afford compound 7-3 (R=H, tetrahydropyran-2-yl- or 1-pyrollidinylmethyl and R'=$CO_2H$, $CO_2Me$, $CO_2Et$, C≡$CCO_2Me$, C≡$CCO_2Et$, CH=$CHCO_2Me$, CH=$CHCO_2Et$, $CH_2CH_2CO_2Me$, $CH_2CH_2CO_2Et$). When R=tetrahydropyran-2-yl- or 1-pyrollidinylmethyl treatment with acid (TFA, PPTS, HCl etc.) provides compound 7-3 where R=H. In step 2, treatment of compound 7-2 (Z=Br, I, or OTf, and R'=$CO_2H$, $CO_2Me$, $CO_2Et$, C≡$CCO_2Me$, C≡$CCO_2Et$, CH=$CHCO_2Me$, CH=$CHCO_2Et$, $CH_2CH_2CO_2Me$, $CH_2CH_2CO_2Et$) with a catalyst derived from a palladium salt ($Pd(OAc)_2$, $PdCl_2$, $Pd(O_2CCF_3)_2$, etc.) and a phosphine ligand ($PPh_3$, $P(O-tolyl)_3$, etc.) is followed by exposure to compound 7-1 (X=Li, ZnCl, MgBr, $SnBu_3$, $B(OH)_2$ and R=tetrahydropyran-2-yl- or 1-pyrollidinylmethyl) to afford compound 7-3 (R=tetrahydropyran-2-yl- or 1-pyrollidinylmethyl and R'=$CO_2H$, $CO_2Me$, $CO_2Et$, C≡$CCO_2Me$, C≡$CCO_2Et$, CH=$CHCO_2Me$, CH=$CHCO_2Et$, $CH_2CH_2CO_2Me$, $CH_2CH_2CO_2Et$). When R=tetrahydropyran-2-yl- or 1-pyrollidinylmethyl treatment with acid (TFA, PPTS, HCl etc.) provides compound 7-3 where R=H. Step 3 discloses a HATU-mediated coupling reaction of diamino uracil moiety with bicyclo[2.2.2]octane acid (which has been described above). In step 4, treatment of compound 7-4 (X=Cl, Br, I) with a catalyst derived from a palladium salt ($Pd(OAc)_2$, $PdCl_2$, $Pd(O_2CCF_3)_2$, etc.) and a phosphine ligand ($PPh_3$, $P(o-tolyl)_3$, etc.) is followed by exposure to an olefin (methyl acrylate, methyl propiolate, allyl alcohol, etc.) to afford compound 7-5 (R'=C≡$CCO_2Me$, C≡$CCO_2Et$, CH=$CHCO_2Me$, CH=$CHCO_2Et$, $CH_2CH_2CHO$, etc). Step 5 discloses a base-promoted cyclization of uracil 7-5 to a xanthine of type 7-3 (which has been described above). Similarly, the base-promoted cyclization of uracil 7-4 to a xanthine of type 7-6 in step 6 has been described above. In step 7, treatment of compound 7-6 (X=Cl, Br, I, OTf) with a catalyst derived from a palladium salt ($Pd(OAc)_2$, $PdCl_2$, $Pd(O_2CCF_3)_2$, etc.) and a phosphine ligand ($PPh_3$, $P(o-tolyl)_3$, etc.) is followed by exposure to an olefin (methyl acrylate, methyl propiolate, allyl alcohol, etc.) to afford compound 7-3 (R=H, R'=C≡$CCO_2Me$, C≡$CCO_2Et$, CH=$CHCO_2Me$, CH=$CHCO_2Et$, $CH_2CH_2CHO$, etc). Step 8 discloses oxidation of the terminal aldehyde group in compound 7-3 (R=H, R'=CH$_2$CH$_2$CHO) which is accomplished by standard means (a. NaClO$_2$, NaH$_2$PO$_4$, 2-methyl-2-butene; b. NaIO4; etc.)

DEFINITIONS

All temperatures are in degrees Celsius (° C.).

TLC refers to thin-layer chromatography.

HPLC refers to high pressure liquid chromatography.

HMPA refers to hexylmethylphosphoramide.

THF refers to tetrahydrofuran.

THP refers to tetrahydropyranyl.

DMSO refers to dimethylsudfoxide.

DMF refers to dimethylformamide.

DDQ refers to 2,3-dichloro-5,6-dicyano-1,4-benzoquinone.

DBU refers to 1,8-diazabicyclo[5.4.0]undec-7-ene.

DBN refers to 1,5-diazabicyclo[4.3.0]non-5-ene.

DMAC refers to dimethylacetamide.

LDA refers to lithium diisopropylamide.

p-TSA refers to p-toluenesulfonic acid monohydrate.

NBS refers to N-bromosuccinimide.

NCS refers to N-chlorosuccinimide.

TEA refers to triethylamine.

BOC refers to t-butyl carbamate or tert-butoxycarbonyl.

Hunig's base refers to diisopropylethylamine, [(CH$_3$)$_2$CH]$_2$—N—CH$_2$CH$_3$.

DMAP refers to dimethylaminopyridine, (CH$_3$)$_2$N-pyridin-1-yl.

TFA refers to trifluoracetic acid, CF$_3$—COOH.

CDI refers to 1,1'-carbonyldiimidazole.

DIBAL refers to diusobutyl aluminum hydride.

THAM refers to tris(hydroxymethyl)aminomethane.

TMS refers to trimethylsilyl.

15-crown-5 refers to 1,4,7,10,13-pentaoxacyclopentadecane.

12-crown 4 refers to 1,4,7,10-tetraoxacyclododecane.

DMPU refers to 1,3-dimethyl-3,4,5,6-tetrahydro-2(1H)-pyrimidinone.

TMU refers to 1,1,3,3-tetramethylurea.

Saline refers to an aqueous saturated sodium chloride solution.

Chromatography (column and flash chromatography) refers to purification/separation of compounds expressed as (support, eluent). It is understood that the appropriate fractions are pooled and concentrated to give the desired compound(s).

IR refers to infrared spectroscopy.

FTIR refers to Fourier transform infrared spectroscopy.

ATR refers to attenuated total reflectance.

UV refers to ultraviolet spectroscopy.

NMR refers to nuclear (proton) magnetic resonance spectroscopy, chemical shifts are reported in ppm (d) downfield from tetramethylsilane.

psi refers to pounds per square inch of pressure.

$[a]_D^{25}$ refers to the angle of rotation of plane polarized light (specific optical rotation) at 25° with the sodium D line (589A).

MS refers to mass spectrometry expressed as m/e, m/z or mass/charge unit. [M+H]$^+$ refers to the positive ion of a parent plus a hydrogen atom. EI refers to electron impact. CI refers to chemical ionization. FAB refers to fast atom bombardment.

The phrase "pharmaceutically acceptable" refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

Pharmaceutically acceptable anion salts include salts of the following acids methanesulifonic, hydrochloric, hydrobromic, sulfuric, phosphoric, nitric, benzoic, citric, tartaric, fumaric, maleic, CH$_3$—(CH$_2$)$_n$—COOH where n is 0 thru 4, HOOC—(CH$_2$)$_n$—COOH where n is as defined above.

When solvent pairs are used, the ratios of solvents used are volume/volume (v/v).

When the solubility of a solid in a solvent is used the ratio of the solid to the solvent is weight/volume (wt/v).

R$_a$ is H, C$_{1-5}$ alkyl, benzyl where the phenyl ring is optionally substituted with one to three halo, hydroxyl, or C$_{1-3}$ alkoxy.

R$_b$ is H, C$_{1-5}$ alkyl, benzyl where the phenyl ring is optionally substituted with one to three halo, hydroxyl, or C$_{1-3}$ alkoxy. When R$_a$ and R$_b$ are both present in the same molecule, they can be the same or different.

R$_c$ is H, C$_{1-5}$ alkyl, benzyl where the phenyl ring is optionally substituted with one to three halo, hydroxyl, or C$_{1-3}$ alkoxy. When R$_a$ and R$_c$ are both present in the same molecule, they can be the same or different.

R$_d$ is H, C$_{1-5}$, benzyl where the phenyl ring is optionally substituted with one to three halo, hydroxyl, or C$_{1-3}$ alkoxy. When R$_c$ and R$_d$ are in the same molecule such as compound (XX) they must be different. When R$_a$ and R$_d$ are both present in the same molecule, they must be different.

R$_e$ is —H, C$_1$–C$_5$ alkyl, benzyl where the ring is optionally substituted with one to three halo, hydroxyl, or C$_{1-3}$ alkoxy. When R$_1$ and R$_5$ are both present in the same molecule, they must be different.

R$_f$ is —(CH$_2$)$_n$—CO—OR' and —CH=CH—CO—OR' where n is 0, 1, or 2 and R' is H or C$_{1-3}$ alkyl.

R$_g$ is halo or triflate.

M is —CH$_2$—CH$_2$— or —CH=CH—.

Tf refers to trifluoromethylsullfonyl, —SO$_2$—CF$_3$.

LG refers to "Leaving Group" and is —O—SO$_2$-phenyl-NO$_2$, —O—SO$_2$—CH$_3$, —O—SO$_2$-phenyl-CH$_3$, or —O—SO$_2$—CF$_3$.

Uses for the Adenosine Antagonist Compounds

Activation of adenosine receptors elicits many physiological responses, including reductions in renal blood flow, reductions in glomerular filtration rate, and increases in sodium reabsorption in kidney. Activation of adenosine receptors reduces heart rate, reduces conduction velocity, and reduces contractility. These, and the other effects of activation of adenosine receptors in other organs, are normal regulatory processes. However, these effects become pathological in many disease states. Thus, adenosine antagonists have extensive application in both prevention and treatment of disease. Diseases that can be prevented and/or treated with adenosine receptor antagonists include any conditions (a) marked by the presence of an abnormal level of adenosine and/or (b) requiring for treatment the inhibition or stimulation of adenosine production and/or release. Such conditions include, but are not limited to, congestive heart failure, cardio-pulmonary resuscitation, hemorrhagic shock, and other cardiac and circulatory disorders; degenerative disorders of the central nervous system; respiratory disorders (e.g., bronchial asthma, allergic lung diseases); and many diseases for which diuretic treatment is indicated (e.g., acute and chronic renal failure, renal insufficiency, hypertension). Degenerative illnesses such as Parkinson's disease, depression, traumatic brain damage, post-stroke neurological deficit, neonatal brain trauma, dyslexia, hyperactivity, and cystic fibrosis have all been linked to adenosine receptor activity. Other conditions in which treatment with adenosine receptor antagonists can have therapeutic utility include cirrhotic ascites, neonatal apnea, renal failure associated with traditional diuretic therapy, diabetes, and asthma.

Additionally, applicants have discovered that the administration of highly selective and potent adenosine $A_1$ receptor antagonists, for example, can elicit a diuretic response when administered alone and can potentiate the diuretic response to traditional diuretics. In addition, administration of adenosine receptor antagonists with traditional diuretics attenuate the reduction of glomerular filtration rate induced by traditional diuretics. The claimed methods are applicable, for example, in edematous conditions, such as congestive heart failure and ascites.

Administration of the Adenosine Antagonist Compounds

The compounds can be administered to an animal (e.g., a mammal such as a human, non-human primate, horse, dog, cow, pig, sheep, goat, cat, mouse, rat, guinea pig, rabbit, hamster, gerbil, ferret, lizard, reptile, or bird). The compounds can be administered in any manner suitable for the administration of pharmaceutical compounds, including, but not limited to, pills, tablets, capsules, aerosols, suppositories, liquid formulations for ingestion or injection or for use as eye or ear drops, dietary supplements, and topical preparations. The compounds can be administered orally, intranasally, transdermally, intradermally, vaginally, intraaurally, intraocularly, buccally, rectally, transmucosally, or via inhalation, implantation (e.g., surgically), or intravenous administration.

Optionally, the compounds can be administered in conjunction with a non-adenosine modifying pharmaceutical composition (e.g., in combination with a non-adenosine modifying diuretic as described, for example, in co-pending application PCT/US99/08879 filed Apr. 23, 1999, incorporated herein by reference in its entirety).

The invention will be further described in the following examples, which do not limit the scope of the invention described in the claims.

EXAMPLES

Example 1

8-(3-Oxo-2-oxa-bicyclo[2.2.2]oct-1-yl)-1,3-dipropyl-3,7-dihydro-purine-2,6-dione 1,3-Dipropyl-7-(tetrahydropyran-2-yl)-3,7-dihydro-purine-2,6-dione (3.0 g, 9.37 mmol) was dissolved in 100 ml of anhydrous THF and cooled to −78° C. nBuLi (2.5 M in hexanes, 4.70 ml) was added, followed by 4-oxo-cyclohexanecarboxylic acid ethyl ester (9.37 mmol, 1.5 ml) and the reaction mixture was slowly warmed to RT and stirred at RT overnight. The next day, the reaction was quenched with sat'd. aq. $NH_4Cl$. The reaction was diluted with water and extracted with EtOAc. The organic layer was dried and concentrated under reduced pressure. Purification by chromatography (2:1 hex/EtOAc) afforded 1.30 g of the desired alcohol derivative.

This product (290 mg, 0.592 mmol) was dissolved in 3 ml of THF and an aq. solution of LiOH (2M, 0.60 ml) was added. The reaction mixture was stirred at RT for 18 h. It was then quenched with 10% aq. citric acid and extracted with EtOAc. The organic layer was dried ($Na_2SO_4$) and concentrated.

The resulting acid was dissolved in of acetic anhydride (3 ml) and refluxed for 1 h. It was then cooled to RT and concentrated. The resulting residue was dissolved in EtOAc and washed with sat'd. aq. $NaHCO_3$, brine, dried ($Na_2SO_4$), and concentrated. Purification by chromatography (2:1 EtOAc/hex) afforded the title compound. MS ($ES^+$) 361.

Example 2

8-(2-Oxa-bicyclo[2.2.2]oct-1-yl)-1,3-dipropyl-3,7-dihydro-purine-2,6-dione

4-[2,6-dioxo-1,3-dipropyl-7-(tetrahydropyran-2-yl)-2,3,6,7-tetrahydro-1H-purin-8-yl]-4-hydroxy-cyclohexanecarboxylic acid ethyl ester (Example 1) (270 mg, 0.551 mmol) was dissolved in 4 ml of anhydrous THF, and $LiBH_4$ (2.0 M solution in THF, 0.55 ml) was added. The reaction mixture was stirred at RT overnight. The next day, the reaction was quenched with 10% aq. citric acid and extracted with EtOAc. The organic layer was concentrated under reduced pressure and the resulting crude product was purified by chromatography (1:1 hex/EtOAc).

The pure diol (90 mg, 0.201 mmol) was dissolved in $CH_2Cl_2$ (5 ml) and $Et_3N$ (1.2 eq) was added. This was then followed by addition of MsCl (1.1 eq). The reaction was stirred at RT for 1 h and then quenched with sat'd. aq. $NH_4Cl$ and extracted with $CH_2Cl_2$. The organic layer was dried ($Na_2SO_4$) and concentrated.

The resulting residue was dissolved in THF (2 ml) and 1 N HCl (1 ml). The reaction mixture was stirred at RT for 12 h and diluted with $H_2O$ and extracted with EtOAc. The organic layer was dried ($Na_2SO_4$) and concentrated under reduced pressure. Purification by HPLC using aq. $CH_3CN$ afforded the title compound. MS($ES^+$) 347.

Example 3

Acetic acid 1-(2,6-dioxo-1,3-dipropyl-2,3,6,7-tetrahydro-1H-purin-8-yl)-2-oxa-bicyclo[2.2.2]oct-4-ylmethyl ester 4-Oxo-cyclohexanecarboxylic acid ethyl ester was converted to the corresponding ketal derivative according to an established procedure (Greene, *Protective Groups in Organic Synthesis*, Third Edition). This ketal derivative (1.0 g, 4.67 mmol) was dissolved in anhydrous THF (15 ml). In a separate flask, 2,2,6,6-tetramethylpiperidine (1.2 ml, 1.5 eq) was dissolved in of THF (30 ml) and cooled to −78° C. and nBuLi (2.80 ml, 2.5 M solution in hexanes, 1.5 eq) was added. After 15 min, the ketal solution was added and the reaction mixture was stirred at −78° C. for 1 h. Methyl chloroformate (0.72 ml, 2 eq) was added and the reaction mixture was warmed to RT. The reaction was quenched with sat'd. aq. $NH_4Cl$ and extracted with EtOAc. The organic layer was dried ($Na_2SO_4$) and concentrated under reduced pressure. Purification by chromatography (2:1 hex/EtOAc) afforded the diester intermediate.

This diester (8.0 g, 29.4 mmol) was dissolved in dry $Et_2O$ (500 ml) and cooled to 0° C. $LiAlH_4$ (2.2 g, 2 eq) was added in small portions over a period of 15 min. The reaction mixture was stirred at 0° C. for 15 min and then warmed to RT and stirred for 1 h. It was then cooled to 0° C. and carefully quenched with of 5% aq. NaOH (10 ml). The mixture was filtered and the filtrate was concentrated to afford 3.30 g of diol intermediate.

This diol (1.60 g, 7.9 mmol) was dissolved in pyridine (10 ml) and TsCl (3.3 g, 2.2 eq) was added. The reaction mixture was stirred at RT for 18 h. It was then diluted with EtOAc and washed with 10% aq. citric acid. The organic layer was dried ($Na_2SO_4$) and concentrated to afford the ditosylate derivative.

This material was dissolved in THF (60 ml) and of 1 N HCl (30 ml). The reaction mixture was stirred under reflux for 1 h. The reaction mixture was cooled to RT and extracted with EtOAc. The organic layer was dried ($Na_2SO_4$) and concentrated under reduced pressure. Purification by chromatography (1:1 hex/EtOAc) afforded 2.0 g of the ditosylate derivative of 4,4-bis-hydroxymethyl-cyclohexanone.

1,3-Dipropyl-7-(tetrahydro-pyran-2-yl)-3,7-dihydro-purine-2,6-dione (5.30 g, 16.5 mmol) was dissolved in anhydrous THF (250 ml) and cooled to −78° C. nBuLi (2.5 M in hexanes, 6.60 ml, 1 eq) was added, followed by the ditosylate derivative of 4,4-bis-hydroxymethyl-cyclohexanone (7.7 g, 1 eq) and the reaction mixture was slowly warmed to RT and stirred at RT overnight. The next day, the reaction was quenched with sat'd. aq. $NH_4Cl$. The reaction was diluted with water and extracted with EtOAc. The organic layer was dried and concentrated under reduced pressure. Purification by chromatography (2:1 hex/EtOAc) afforded 10.4 g of the ditoylate xanthine derivative.

This intermediate (9.0 g) was dissolved in dry THF (200 ml) and powdered NaOH (9.0 g) was added. The reaction mixture was stirred under reflux for 24 h. It was then cooled to RT and diluted with $H_2O$ and extracted with EtOAc. The organic layer was dried ($Na_2SO_4$) and concentrated under reduced pressure. Purification by chromatography (2:1 hex/EtOAc) afforded 5.6 g of the monotosylate derivative.

This monotosylate derivative (4.0 g, 6.5 mmol) was dissolved in DMSO(70 ml). NaOAc (9 g) was added and the reaction mixture was stirred at 70–80° C. for 2 days. The reaction mixture was cooled to RT and diluted with $H_2O$ and extracted with EtOAc. The organic layer was dried ($Na_2SO_4$) and concentrated. Purification by chromatography (2:1 hex/EtOAc) afforded 800 mg of the title compound. MS (ES$^+$) 419.

Example 4

8-(4-Hydroxymethyl-2-oxa-bicyclo[2.2.2]oct-1-yl)-1,3-dipropyl-3,7-dihydro-purine-2,6-dione Acetic acid 1-(2,6-dioxo-1,3-dipropyl-2,3,6,7-tetrahydro-1H-purin-8-yl)-2-oxa-bicyclo[2.2.2]oct-4-ylmethyl ester was prepared as described in Example 3. This acetate derivative (120 mg, 0.287 mmol) was dissolved in MeOH (5 ml). $K_2CO_3$ (200 mg, 5 eq) was added as a solution in 5 ml of $H_2O$. The reaction mixture was stirred at RT. for 2 h. The reaction mixture was diluted with $H_2O$ and extracted with EtOAc. The organic layer was dried ($Na_2SO_4$) and concentrated under reduced pressure. The resulting residue was purified by preparative HPLC using aq $CH_3CN$ to afford the title compound. MS(ES$^+$) 377.

Example 5

1-(2,6-Dioxo-1,3-dipropyl-2,3,6,7-tetrahydro-1H-purin-8-yl)-2-oxabicyclo-[2.2.2]octane-4-carboxylic acid Acetic acid 1-(2,6-dioxo-1,3-dipropyl-2,3,6,7-tetrahydro-1H-purin-8-yl)-2-oxa-bicyclo[2.2.2]oct-4-yl methyl ester was prepared as described in Example 3. This acetate derivative (400 mg) was dissolved in 3 ml of $CH_2Cl_2$ and 3 ml of dihydropyran. PPTS (10 mg) was added and the reaction mixture was stirred at RT for 18 h. The reaction mixture was diluted with $CH_2Cl_2$ and washed with $NaHCO_3$, 5% aq. citric acid and brine. The organic layer was dried ($Na_2SO_4$) and concentrated under reduced pressure.

The resulting residue was dissolved in 10 ml of MeOH and $K_2CO_3$ (450 mg) was added as a solution in 10 ml of $H_2O$. The resulting reaction mixture was stirred at RT. for 18 h. It was then diluted with $H_2O$ and extracted with EtOAc. The organic layer was dried ($Na_2SO_4$) and concentrated to afford the alcohol derivative, 8-(4-hydroxymethyl-2-oxa-bicyclo[2.2.2]oct-1-yl)-1,3-dipropyl-7-(tetrahydro-pyran-2-yl)-3,7-dihydro-purine-2,6-dione.

This material (320 mg, 0.7 mmol) was dissolved in 8 ml of DMF. PDC (1.0 g, 4 eq) was added and the reaction mixture was stirred at RT for 18 h. The reaction mixture was diluted with 3 ml of 10% aq citric acid and 20 ml of $H_2O$ and quickly extracted with EtOAc. The organic layer was dried ($Na_2SO_4$) and concentrated under reduced pressure. The residue was dissolved in 10 ml of $H_2O$ and 20 ml of $CH_3CN$ along with 1 ml of TFA. The reaction mixture was stirred at RT for 18 h. The reaction mixture was concentrated. The resulting residue was purified by preparative HPLC using aq. $CH_3CN$ to afford the title compound. MS (ES$^+$) 391.

Example 6

3-[1-(2,6-Dioxo-1,3-dipropyl-2,3,6,7-tetrahydro-1H-purin-8-yl)-2-oxa-bicyclo-[2.2.2]oct-4-yl]-acrylic acid 8-(4-Hydroxymethyl-2-oxa-bicyclo[2.2.2]oct-1-yl)-1,3-dipropyl-7-(tetrahydro-pyran-2-yl)-3,7-dihydro-purine-2,6-dione was synthesized according to the procedure outlined in EXAMPLE 4. This alcohol derivative (140 mg, 0.3 mmol) was dissolved in 5 ml of $CH_2Cl_2$ along with the Dess-Martin reagent (Lancaster, 155 mg, 1.2 eq). The reaction mixture was stirred at RT for 1 h. The reaction mixture was diluted with aq sodium sulfite (1 M) and extracted with $CH_2Cl_2$. The organic layer was dried ($Na_2SO_4$) and concentrated under reduced pressure to afford the a t dehyde intermediate.

This material was immediately dissolved in 4 ml of anhydrous THF. In a separate flask, trimethylphosphonoacetate (60 μL, 1.2 eq) was dissolved in 3ml of anhydrous THF and cooled to 0° C. and KHDMS (0.5 M in PhMe, 730 μL) was added. This mixture was stirred at 0° C. for 10 min and then added to the solution of the aldehyde. The reaction mixture was stirred at RT for 3 h and then quenched with sat'd. aq. $NH_4Cl$ and extracted with EtOAc. The organic layer was dried ($Na_2SO_4$) and concentrated.

The resulting residue was dissolved in 4 ml of THF and 4 ml of H120 Containing LiOH (4 eq) and stirred at RT for 18 h. The reaction mixture was dilute, with aq. citric acid and extracted with EtOAc. The organic layer was dried ($Na_2SO_4$) and concentrated. Purification by preparative HPLC using aq. $CH_3CN$ afforded the titled compound. MS (ES$^+$) 417.

Example 7

3-[1-(2,6-Dioxo-1,3-dipropyl-2,3,6,7-tetrahydro-1H-purin-8-yl)-2-oxa-bicyclo-[2.2.2]oct-4-yl]-propionic acid 3-[-(2,6-Dioxo-1,3-dipropyl-2,3,6,7-tetrahydro-1H-purin-8-yl)-2-oxa-bicyclo[2.2.2]oct-4-yl]-acrylic acid was dissolved in 50 ml of MeOH. 10% Pd on C (10 mg) was added and the reaction mixture was hydrogenated at RT under 55 psi of $H_2$ for 30 min. The reaction mixture was filtered through a pad of Celite and the filtrate was concentrated under reduced pressure to afford the title compound. MS (ES$^+$) 419.

Example 8

5-(2,6-Dioxo-1,3-dipropyl-2,3,6,7-tetrahydro-1H-purin-8-yl)-bicyclo[3.2.1]octane-1-carboxylic acid To a solution of bicyclo[3.2.1]octane-1,5-dicarboxylic acid monomethyl ester (Della, E. W.; Tsanaktsidis, J. *Aust. J. Chem.* 1985, 38, 1705; Della, E. W.; Tsanaktsidis, J. *Aust. J. Chem.* 1986, 39, 2061); (5.94 mmol, 1.26 g), HATU (5.94 mmol, 2.26 g), and 5,6-diamino-1,3-dipropyl-1H-pyrimidine-2,4-dione hydrochloride (Daly, J. W. et al., *J. Med.Chem.*, 1985, 28 (4), 487) (5.94 mmol, 1.56 g) in DMF (25 ml) was added iPr$_2$NEt (17.82 mmol, 3.1 ml). The reaction was stirred overnight at RT. It was concentrated at the pump to remove DMF. The residue was dissolved in EtOAc and washed with 1N HCl, 5% NaHCO$_3$, and brine, and dried (MgSO$_4$). Filtration and evaporation followed by flash column chromatography, eluting with 3:1 EtOAc/hexanes provided product (0.7 g, 28%) as an oil. MS (ES$^+$) 443.1 (M+Na, 100%), 421.4 (M+H, 10%).

A solution of 5-(6-amino-2,4-dioxo-1,3-dipropyl-1,2,3,4-tetrahydro-pyrimidin-5-ylcarbamoyl)-bicyclo[3.2.1]octane-1-carboxylic acid ethyl ester (0.238 mmol, 0.10 g) in 20% NaOH (2.0 ml) and MeOH (10.0 ml) was stirred and refluxed 5 h. The reaction was cooled to room temperature and then concentrated to remove MeOH. The aqueous was acidified (pH 2–3) with conc. HCl and then extracted with EtOAc. The combined EtOAc extracts were washed with $H_2O$ and brine, and dried (MgSO$_4$). Filtration and evaporation followed by reverse phase HPLC provided product (0.039 g, 42%) as a solid. MS (ES$^+$) 389.12 (M+H, 100%)

Example 9

8-(4-Hydroxy-2,6-dioxa-tricyclo[3.3.1.0$^{3,7}$]non-1-yl)-1,3-dipropyl-3,7-dihydro-purine-2,6-dione A solution of LDA was prepared at −78° C. by addition of n-BuLi (1.8 M in hexanes, 1.7 ml) to a solution of iPr$_2$NH (3.61 mmol, 0.506 ml) in THF (25 ml). After addition, the LDA was aged at −78° C. for 45 min. To this was added slowly at −78° C. a solution of 1,3-dipropyl-7-(tetrahydropyran-2-yl)-3,7-dihydropurine-2,6-dione (Example 52) (2.78 mmol, 0.89 g) in THF (35 ml). After stirring another 1 h at −78° C., a solution of 8-oxa-bicyclo[3.2.1]oct-6-en-3-one (Mann, J. et al., *J. Chem. Soc. Perkin Trans I* 1992, 787) (2.78 mmol, 0.345 g) in THF (5 ml) was added. The reaction was stirred overnight with warming to room temperature. It was quenched by addition of saturated NH$_4$Cl and extracted with EtOAc. The combined organic extracts were washed with saturated NH$_4$Cl, H$_2$O and brine, and dried (MgSO$_4$). Filtration and evaporation followed by flash column chromatography, eluting with an EtOAc/CH$_2$Cl$_2$ gradient, provided the coupled product (0.55 g, 45%). MS (ESP+, 60V): 445.07 (M+H, 35%), 361.06 (48%), 343.05 (100%).

To a solution of 8-(3-hydroxy-8-oxa-bicyclo[3.2.1]oct-6-en-3-yl)-1,3-dipropyl-7-(tetrahydropyran-2-yl)-3,7-dihydropurine-2,6-dione (prepared as described above) (0.225 mmol, 0.10 g) in iPrOH (2 ml) and H$_2$O (1 ml) was added MMPP (80%, 0.45 mmol, 0.223 g) in one portion. After 5d at room temperature, the reaction was quenched by addition of sat'd. aq. Na$_2$S$_2$O$_3$ and concentrated to remove iPrOH. The aqueous residue was partitioned between EtOAc and sat'd. NaHCO$_3$. The organic extracts were washed with H$_2$O and brine, and dried (MgSO$_4$). Filtration and evaporation provided product (0.093 g, 90%) as a foam. $^{13}$C NMR (75 MHz, CDCl$_3$): 11.50, 11.63, 21.55, 21.61, 21.72, 23.00, 25.01, 32.17, 37.96, 40.42, 43.52, 45.19, 54.46, 54.62, 70.46, 70.79, 71.51, 71.64, 86.09, 107.18, 147.34, 151.21, 155.19, 157.82.

To a solution of 8-(4-hydroxy-2,6-dioxa-tricyclo[3.3.1.0$^{3,7}$]non-1-yl)-1,3-dipropyl-7-(tetrahydro-pyran-2-yl)-3,7-dihydro-purine-2,6-dione (0.065 mmol, 0.030 g) in 1:1 THF/MeOH (6 ml) was added 1N HCl (3 drops). The reaction was stirred at room temperature 4 h and then concentrated to dryness. The residue was purified by reverse phase HPLC, providing product (0.0094 g, 38%). $^1$H NMR (400 MHz, d6-DMSO): 0.80–0.89 (m, 6H), 1.48–1.56 (m, 2H), 1.60–1.70 (m, 2H), 1.9–2.09 (m, 2H), 2.2–2.25 (m, 1H), 3.78–3.82 (m, 2H), 3.89–3.91 (m, 2H), 3.99 (s, 1H), 4.21 (br s, 1H), 4.51 (br s, 1H), 4.80 (m, 1H).

Example 10

8-(5-Hydroxymethyl-bicyclo[3.2.1]oct-1-yl)-1,3-dipropyl-3,7-dihydro-purine-2,6-dione To a solution of 5-(6-amino-2,4-dioxo-1,3-dipropyl-1,2,3,4-tetrahydro-pyrimidin-5-ylcarbamoyl)-bicyclo[3.2.1]octane-1-carboxylic acid methyl ester (prepared as described for Example 8) (0.714 mmol, 0.30 g) was added LiBH$_4$ (2M in THF, 0.54 ml). After stirring overnight at room temperature and then at reflux 90 min. The reaction was quenched at room temperature by addition of 1N HCl, diluted with H$_2$O and extracted with EtOAc. The combined organics were washed with saturated NaHCO$_3$, H$_2$O, and brine, and dried (MgSO$_4$). Filtration and evaporation provided product (0.20 g, 71%) as an oil. MS (ES) 415.15 (M+Na, 100%), 393.5 (M+H, 48%)

A solution of 5-hydroxymethyl-bicyclo[3.2.1]octane-1-carboxylic acid (6-amino-2,4-dioxo-1,3-dipropyl-1,2,3,4-tetrahydro-pyrimidin-5-yl)-amide (0.51 mmol, 0.20 g) in 20% NaOH (2.0 ml) and MeOH (10.0 ml) was stirred and refluxed overnight. The reaction was cooled to room temperature and then concentrated to remove MeOH. The aqueous was acidified (pH 2–3) with conc. HCl and then extracted with EtOAc. The combined EtOAc extracts were washed with saturated NaHCO$_3$, H$_2$O and brine, and dried (MgSO$_4$). Filtration and evaporation followed by flash chromatography eluting with 3:2 EtOAc/CH$_2$Cl$_2$ provided title compound (0.077 g, 40%) as an oil. $^{13}$C NMR (100 MHz, CDCl$_3$): 11.53 (q), 11.74 (q), 20.26 (t), 21.71 (t), 31.62 (t), 34.15 (t), 37.29 (t), 43.49 (s), 45.54 (t), 45.67 (t), 46.14 (t), 46.90 (t), 70.51 (t), 71.11 (s), 107.03 (s), 149.25 (s), 151.54 (s), 155.88 (s), 162.58 (s).

Example 11

[1-(2,6-Dioxo-1,3-dipropyl-2,3,6,7-tetrahydro-1H-purin-8-yl]-2,6-dioxa-tricyclo-[3.3.1.0$^{3,7}$]non-4-yloxyl-acetic acid To a solution of 8-(4-hydroxy-2,6-dioxa-tricyclo[3.3.1.0$^{3,7}$]non-1-yl)-1,3-dipropyl-7-(tetrahydro-pyran-2-yl)-3,7-dihydro-purine-2,6-dione (Example 9) (0.065 mmol, 0.030 g) in THF (2 ml) was added NaH (60% dispersion, 0.068 mmol, 0.0027 g) in one portion. The reaction was stirred at room temperature 1 h, and then t-butyl bromoacetate (0.068 mmol. 10 µL) was added. After 3d, the reaction was quenched with satuiaied NH₄Cl and extracted with EtOAc (3×). The combined organics were washed with brine and dried (MgSO₄). Filtration and evaporation yielded product (0.059 g) contaminated with t-butyl bromoacetate. MS (ES⁺) 575.15 (M+H).

A solution of {1-[2,6-dioxo-1,3-dipropyl-7-(tetrahydropyran-2-yl)-2,3,6,7-tetrahydro-1H-purin-8-yl]-2,6-dioxa-tricyclo[3.3.1.0$^{3,7}$]non-4-yloxy}-acetic acid tert-butyl ester (0.10 mmol, 0.059 g) in CH₂Cl₂ (1 ml) was treated with TFA (1 ml) and stirred at room temperature overnight. The reaction was concentrated to dryness and the residue purified by reverse phase HPLC to provide product (0.0036 g, 8%). MS (ES⁺) 435.13 (M+H).

Example 12

3-[5-(2,6-Dioxo-1,3-dipropyl-2,3,6,7-tetrahydro-1H-purin-8-yl)-bicyclo-[3.2.1]oct-1-yl]-acrylic acid To a solution of 5-(2,6-dioxo-1,3-dipropyl-2,3,6,7-tetrahydro-1H-purin-8-yl)-bicyclo[3.2.1]octane-1-carboxylic acid (Example 8) (1.29 mmol, 0.50 g), HATU (1.29 mmol, 0.49 g), and N,O-dimethylhydroxylamine hydrochloride (1.29 mmol, 0.126 g) in DMF (12 ml) was added iPr₂NEt (3.86 mmol, 0.67 ml). The reaction was stirred overnight at RT. It was concentrated at the pump to remove DMF. The residue was dissolved in EtOAc and washed with 1N HCl, sat'd. NaHCO₃, and brine, and dried (MgSO₄). Filtration and evaporation provided product (0.791 g) contaminated with DMF. MS (ES⁺) 432.13 (M+H)

To a solution of 5-(2,6-Dioxo-1,3-dipropyl-2,3,6,7-tetrahydro-1H-purin-8-yl)-bicyclo[3.2.1]octane-1-carboxylic acid methoxy-methyl-amide (0.232 mmol, 0.100 g) in THF (3 ml) at −78° C. was added a solution of LiAlH₄ (1M in THF, 0.52 ml). After addition, reaction was stirred at −78° C. 30 min, then at 0° C. 30 min. The reaction was quenched carefully by the sequential addition of H₂O (20 µL), 20% NaOH (20 µL) and H₂O (40 µL). The suspension was stirred briskly overnight, then filtered through Celite, rinsing the flask and cake generously with THF. Evaporation followed by flash chromatography, eluting with 5% THF/CH₂Cl₂ provided product (0.048 g, 56%) as an oil. MS (ES⁺): 373.17 (M+H).

To a solution of trimethyl phosphonoacetate (0.310 mmol, 0.056 g) in THF (4 ml) at 0° C. was added a solution of KHMDS (0.5 M in PhMe, 0.6 ml). After stirring 45 min, a solution of 5-(2,6-Dioxo-1,3-dipropyl-2,3,6,7-tetrahydro-1H-purin-8-yl)-bicyclo-[3.2.1]octane-1-carbaldehyde (0.129 mmol, 0.048 g) in THF (2 ml) was added slowly. After stirring overnight at room temperature, the reaction was quenched with saturated NH₄Cl and extracted with EtOAc. The combined organics were washed with saturated NaHCO₃, brine, and dried (MgSO₄). Filtration and evaporation yielded product (0.119 g) contaminated with excess trimethyl phosphonoacetate. MS (ES⁺) 429.16 (M+H)

A solution of 3-[5-(2,6-dioxo-1,3-dipropyl-2,3,6,7-tetrahydro-1H-purin-8-yl)-bicyclo-[3.2.1]oct-1-yl]-acrylic acid methyl ester (0.129 mmol, 0.055 g) in THF (4 ml) was treated at room temperature with 1N LiOH (1.1 ml). The reaction was heated overnight at reflux. The reaction was cooled to room temperature, diluted with H₂O, acidified with conc. HCl (pH 2–3) and extracted with EtOAc. The combined organics were washed with brine and dried (MgSO₄). Filtration and evaporation followed by reverse phase HPLC provided pure product (0.010 g, 19%). MS (ES⁺) 397.24 (M+H−OH, 100%); MS (ES⁻) 413.01 (M−H, 100%)

Example 13

4-(2,6-Dioxo-1,3-dipropyl-2,3,6,7-tetrahydro-1H-purin-8-yl)-bicyclo[2.2.2]octane-1-carboxylic acid To a stirred mixture of 2.00 g (8.84 mmol) of bicyclo[2.2.2]octane-1,4-dicarboxylic acid monoethyl ester, 2.60 g (9.89 mmol) of 5,6-diamino-1,3-dipropyl-1H-pyrimidine-2,4-dione hydrochloride, 5.32 ml (38.1 mmol) of NEt₃, and 30 ml anhydrous acetonitrile was added 3.76 g (9.89 mmol) of HATU. The reaction solution was stirred at rt for 1 h. The reaction mixture was concentrated in vacuo and combined with 40-ml EtOAc and 40 ml of 10% citric acid. The aqueous layer was separated and washed twice with 40-ml portions of EtOAc. The combined organic fractions were washed with 20-ml portions of sat'd NaHCO₃ and brine and conc'd in vacuo. The resultant solid was combined, in a 200-ml round-bottom flask equipped with a condenser, with a mixture of 35 ml of i-PrOH and 35 ml of 1 N KOH (35 mmol) and heated to reflux. After heating for 1 hour, the reaction solution was conc'd in vacuo, taken up in 40 ml of water, and washed twice with 30-ml portions of CH₂Cl₂. The aqueous layer was acidified with conc'd HCl and the resultant precipitate collected by suction filtration to give 3.00 g (87% yield) of an off-white solid. (MH⁺=389.25)

The following compounds were made in an analogous manner.

Example 13a: 8-(4-Hydroxy-bicyclo[2.2.2]oct-1-yl)-1,3-dipropyl-3,7-dihydro-purine-2,6-dione, (MH⁺=361.15)
Example 13b: 8-(4-Pentyl-bicyclo[2.2.2]oct-1-yl)-1,3-dipropyl-3,7-dihydro-purine-2,6-dione, (MH⁺=415.19)
Example 13c: 5-(2,6-Dioxo-1,3-dipropyl-2,3,6,7-tetrahydro-1H-purin-8-yl)-bicyclo[3.2.2]nonane-1-carboxylic acid, (MH⁺=403.30)
Example 13d: [4-(2,6-Dioxo-1,3-dipropyl-2,3,6,7-tetrahydro-1H-purin-8-yl)-bicyclo[2.2.2]oct-1-yl]-carbamic acid methyl ester, (MH⁺=418.15)
Example 13e: 8-(4-Bromo-bicyclo[2.2.2]oct-1-yl)-1,3-dipropyl-3,7-dihydro-purine-2,6-dione, (MNa⁺=425.22)
Example 13f: 8-(1-Aza-bicyclo[2.2.2]oct-4-yl)-1,3-dipropyl-3,7-dihydro-purine-2,6-dione, (MH⁺=346.31)

N-3 alkylations of the precursor monopropyl uracils were performed by literature procedures (Müller, C. E.; Geis, U.; Hipp, J.; Schobert, U.; Frobenius, W.; Pawlowski, M.; Suzuki, F.; Sandoval-Ramirez, J. *J. Med. Chem.* 1997, 40, 4396–4405.) on BOC protected 5,6-diamino-1-propyl uracil with subsequent BOC removal from 4N HCl in dioxane. The above coupling-cyclization protocol was then employed to make xanthine derivatives.

Example 13g: 3-(2-Methoxy-ethyl)-8-(4-pentyl-bicyclo[2.2.2]oct-1-yl)-1-propyl-3,7-dihydro-purine-2,6-dione. (MH⁺=431.64)
Example 13h: 4-[3-(2-Methoxy-ethyl)-2,6-dioxo-1-propyl-2,3,6,7-tetrahydro-1H-purin-8-yl]-bicyclo[2.2.2]octane-1-carboxylic acid, (MH⁺=405.63)
Example 13i: 3-[2-(4-Methoxy-phenyl)-ethyl]-8-(4-pentyl-bicyclo[2.2.2]oct-1-yl)-1-propyl-3,7-dihydro-purine-2,6-dione, (MH⁺=507.30)
Example 13j: 4-{3-[2-(4-Methoxy-phenyl)-ethyl]-2,6-dioxo-1-propyl-2,3,6,7-tetrahydro-1H-purin-8-yl}-bicyclo[2.2.2]octane-1-carboxylic acid, (MH⁺=481.2)
Example 13k: 3-Methyl-8-(4-pentyl-bicyclo[2.2.2]oct-1-yl)-1-propyl-3,7-dihydro-purine-2,6-dione, (MH⁺=387.21)
Example 13l: 4-[3-(4-Methoxy-phenyl)-2,6-dioxo-1-propyl-2,3,6,7-tetrahydro-1H-purin-8-yl]-bicyclo[2.2.2]octane-1-carboxylic acid, (MH⁺=453.4)

Example 13m: 4-[2,6-Dioxo-1,3-bis-(3,3,3-trifluoro-propyl)-2,3,6,7-tetrahydro-1H-purin-8-yl]-bicyclo[2.2.2]octane-1-carboxylic acid, ($MH^+$=496.98)

Example 13n: 4-[2,6-Dioxo-1,3-bis-(3,3,3-trifluoro-propyl)-2,3,6,7-tetrahydro-1H-purin-8-yl]-bicyclo[2.2.2]octane-1-carboxylic acid methyl ester, ($MH^+$=511.3)

Example 13o: 3-[4-(6-Oxo-1,3-dipropyl-2-thioxo-2,3,6,7-tetrahydro-1H-purin-8-yl)-bicyclo[2.2.2]oct-1-yl]-propionic acid, ($MH^+$=432.98) from 5,6-diamino-1,3-dipropyl-2-thioxo-2,3-dihydro-1H-pyrimidin-4-one, prepared by a literature procedure (Jacobson, K. A.; Kiriasis, L.; Barone, S.; Bradbury, B. A.; Kammula, U.; Campagne, M.; Secunda, S.; Daly, J. W.; Neumeyer, J. L.; Pfleiderer, W. *J. Med. Chem.* 1989, 32, 1873–1879).

Example 13p: 4-(6-Oxo-1,3-dipropyl-2-thioxo-2,3,6,7-tetrahydro-1H-purin-8-yl)-bicyclo[2.2.2]octane-1-carboxylic acid, ($MH^+$=405.04) from 5,6-diamino-1,3-dipropyl-2-thioxo-2,3-dihydro-1H-pyrimidin-4-one, prepared by a literature procedure (Jacobson, K. A.; Kiriasis, L.; Barone, S.; Bradbury, B. A.; Kammula, U.; Campagne, M.; Secunda, S.; Daly, J. W.; Neumeyer, J. L.; Pfleiderer, W. *J. Med. Chem.* 1989, 32, 1873–1879).

Example 14

4-(2,6-Dioxo-1,3-dipropyl-2,3,6,7-tetrahydro-1H-purin-8-yl)-bicyclo[2.2.2]octane-1-carboxylic acid methyl ester 4-(2,6-Dioxo-1,3-dipropyl-2,3,6,7-tetrahydro-1H-purin-8-yl)-bicyclo[2.2.2]octane-1-carboxylic acid (Example 13) (1.50 g, 3.86 mmol) was combined with 60 ml of MeOH, and 10 drops of conc'd $H_2SO_4$. The reaction solution was brought to reflux until consumption of starting material ceased. Sat'd $NaHCO_3$ was then added until neutral pH and the reaction mixture was conc'd in vacuo. The residue was taken up in EtOAc and washed with sat'd $NaHCO_3$, brine, and dried over $Na_2SO_4$. The EtOAc solution was conc'd in vacuo to give 1.51 g (97% yield) of a white solid. ($MH^+$=403.13)

Example 15

8-(4-Hydroxymethyl-bicyclo[2.2.2]oct-1-yl)-1,3-dipropyl-3,7-dihydro-purine-2,6-dione 4-(2,6-Dioxo-1,3-dipropyl-2,3,6,7-tetrahydro-1H-purin-8-yl)-bicyclo[2.2.2]octane-1-carboxylic acid methyl ester (Example 14) (1.40 g, 3.48 mmol) was combined with $LiBH_4$ (0.379 g, 17.4 mmol), MeOH (0.141 ml, 3.48 mmol), and 100 ml of THF and the resultant mixture was brought to reflux for 18 h. After cooling to rt, 50 ml of 1M HCl were added and the mixture conc'd in vacuo. The residue was dissolved in EtOAc and washed with 1M HCl, sat'd $NaHCO_3$, brine, and dried over $Na_2SO_4$. The EtOAc solution was conc'd in vacuo to give 1.15 g (88% yield), of a white solid. ($MH^+$=375.50)

Example 16

4-(2,6-Dioxo-1,3-dipropyl-2,3,6,7-tetrahydro-1H-purin-8-yl)-bicyclo[2.2.2]octane-1-carbaldehyde To a solution of 0.092 g (0.246 mmol) of 8-(4-Hydroxymethyl-bicyclo[2.2.2]oct-1-yl)-1,3-dipropyl-3,7-dihydro-purine-2,6-dione (Example 15) in 5 ml of $CH_2Cl_2$ was added 0.125 g (0.295 mmol) Dess-Martin periodinane. The reaction mixture was stirred at rt until the oxidation was complete. The reaction solution was filtered through a plug of basic alumina, washed with sat'd $NaHCO_3$, brine, and dried over $Na_2SO_4$. The $CH_2Cl_2$ solution was conc'd in vacuo to give 0.057 g (62% yield) of an off-white solid. ($MH^+$=373.30)

Example 17

3-[4-(2,6-Dioxo-1,3-dipropyl-2,3,6,7-tetrahydro-1H-purin-8-yl)-bicyclo[2.2.2]oct-1-yl]-acrylic acid Trimethylphosphono acetate (0.0.161 g, 0.886 mmol) was dissolved in 12 ml of toluene and cooled to between 0–5° C. KHMDS (0.5 M in toluene) (3.54 ml) was added dropwise while stirring over 5 min. After an additional 30 min at 0–5° C., 0.300 g (0.805 mmol) of Example 16: 4-(2,6-Dioxo-1,3-dipropyl-2,3,6,7-tetrahydro-1H-purin-8-yl)-bicyclo[2.2.2]octane-1-carbaldehyde was added and the reaction was allowed to warm to rt and was stirred for 16 h. The reaction mixture was conc'd in vacuo. Dissolved crude material in 25 ml of MeOH and 10 ml of water added 0.150 g LiOH and stirred at rt overnight. Conc'd in vacuo and redissolved reaction mixture in 15 ml of water. Extracted water layer thrice with 20-ml portions of EtOAc, acidified with conc'd HCl, and collected precipitate by suction filtration to give 0.190 g (57% yield) of the (trans)-acrylic acid product. ($MH^+$=415.08)

Example 18

3-[4-(2,6-Dioxo-1,3-dipropyl-2,3,6,7-tetrahydro-1H-purin-8-yl)-bicyclo[2.2.2]oct-1-yl]-propionic acid 3-[4-(2,6-Dioxo-1,3-dipropyl-2,3,6,7-tetrahydro-1H-purin-8-yl)-bicyclo[2.2.2]oct-1-yl]-acrylic acid (Example 17) (0.050 g) was dissolved in 5 ml of MeOH and combined with 0.005 g of 10% Pd/C. The reaction vessel was purged three times with $N_2$ and then placed under a balloon of $H_2$ gas. After 2 h, the reaction mixture was filtered and conc'd to give 0.037 g (74% yield) of a white solid. ($MH^+$=417.30)

Example 18a: 3-[4-(2,6-Dioxo-1,3-dipropyl-2,3,6,7-tetrahydro-1H-purin-8-yl)-bicyclo[2.2.2]oct-1-yl]-2-methyl-propionic acid, was made in an analogous manner. ($MH^+$=431.36)

Example 19

{[4-(2,6-Dioxo-1,3-dipropyl-2,3,6,7-tetrahydro-1H-purin-8-yl)-bicyclo[2.2.2]octane-1-carbonyl]-methyl-amino}-acetic acid To a stirred mixture of 0.100 g (0.257 mmol) of 4-(2,6-Dioxo-1,3-dipropyl-2,3,6,7-tetrahydro-1H-purin-8-yl)-bicyclo[2.2.2]octane-1-carboxylic acid (Example 13), 0.039 g (0.257 mmol) of sarcosine hydrochloride, 0.143 ml (1.03 mmol) of $NEt_3$, and 2 ml anhydrous acetonitrile was added 0.103 g (0.270 mmol) of HATU. The reaction solution was stirred at rt for 16 h. The reaction mixture was concentrated in vacuo and combined with 10 ml EtOAc and 10 ml of 10% citric acid. The aqueous layer was separated and washed twice with 10-ml portions of EtOAc. The combined organic fractions were washed with 10-ml portions of sat'd $NaHCO_3$ and brine and conc'd in vacuo. The resultant solid was dissolved in a mixture of 5 ml of MeOH and 5 ml of 1 N NaOH and stirred for 16 h. The reaction solution was conc'd in vacuo, taken up in 10 ml of water, and washed twice with 10-ml portions of $CH_2Cl_2$. The aqueous layer was acidified with conc'd HCl and the resultant precipitate collected by suction filtration to give 0.094 g (77% yield) of an off-white solid. ($MH^+$=460.18)

The following compounds were made in an analogous manner:

Example 19a: 4-(2,6-Dioxo-1,3-dipropyl-2,3,6,7-tetrahydro-1H-purin-8-yl)-bicyclo[2.2.2]octane-1-carboxylic acid (2-dimethylamino-ethyl)-amide, (MH$^+$=459.17)

Example 19b: {[4-(2,6-Dioxo-1,3-dipropyl-2,3,6,7-tetrahydro-1H-purin-8-yl)-bicyclo[2.2.2]octane-1-carbonyl]-amino}-acetic acid methyl ester, (MH$^+$=460.3)

Example 19c: 3-{[4-(2,6-Dioxo-1,3-dipropyl-2,3,6,7-tetrahydro-1H-purin-8-yl)-bicyclo[2.2.2]octane-1-carbonyl]-amino}-propionic acid methyl ester, (MH$^+$=389.3)

Example 19d: {[4-(2,6-Dioxo-1,3-dipropyl-2,3,6,7-tetrahydro-1H-purin-8-yl)-bicyclo[2.2.2]octane-1-carbonyl]-amino}-acetic acid, (MH$^+$=446.06)

Example 19e: 1-[4-(2,6-Dioxo-1,3-dipropyl-2,3,6,7-tetrahydro-1H-purin-8-yl)-bicyclo[2.2.2]octane-1-carbonyl]-piperidine-4-carboxylic acid, 1H NMR (400 MHz, CDCl$_3$):δ=0.84 (t, 3H), 0.085 (t, 3H), 1.50–1.68 (m, 6H), 1.84–1.92 (m, 14H), 2.44 (m, 1H), 2.86 (m, 2H), 3.78 (t, 2H), 3.91 (t, 2H), 4.15 (m, 2H).

Example 19f: 8-(4-Dimethylaminomethyl-bicyclo[2.2.2]oct-1-yl)-1,3-dipropyl-3,7-dihydro-purine-2,6-dione, (MH$^+$=402.08)

Example 19g: 8-{4-[(2-Dimethylamino-ethylamino)-methyl]-bicyclo[2.2.2]oct-1-yl}-1,3-dipropyl-3,7-dihydro-purine-2,6-dione, (MH$^+$=445.24)

Example 19h: 4-(2,6-Dioxo-1,3-dipropyl-2,3,6,7-tetrahydro-1H-purin-8-yl)-bicyclo[2.2.2]octane-1-carboxylic acid (2-amino-ethyl)-amide, (MH$^+$=431.06)

Example 20

8-(4-Amino-bicyclo[2.2.2]oct-1-yl)-1,3-dipropyl-3,7-dihydro-purine-2,6-dione

[4-(2,6-Dioxo-1,3-dipropyl-2,3,6,7-tetrahydro-1H-purin-8-yl)-bicyclo[2.2.2]oct-1-yl]-carbamic acid methyl ester (Example 13d) (8.3 gm, 20 mmol) was refluxed in 40 ml of conc. HCl for 3 h. The reaction mixture was concentrated in vacuo to a solid residue which was triturated in acetonitrile to afford 5.8 gm (77%) as a white solid (MH$^+$=360.02)

Example 21

2-(R)-[4-(2,6-Dioxo-1,3-dipropyl-2,3,6,7-tetrahydro-1H-purin-8-yl)-bicyclo-[2.2.2]oct-1-yloxy]-propionic acid 8-(4-Amino-bicyclo[2.2.2]oct-1-yl)-1,3-dipropyl-3,7-dihydro-purine-2,6-dione (Example 20) (0.100 g, 0.279 mmol) was combined with 1.5 ml of (R)-methyl lactate and 0.075 ml of isoamyl nitrite. The mixture was heated to 60° C. for 2 h and cooled to rt. The reaction mixture was conc'd in vacuo and the residue was stirred with 8 ml of a 50% MeOH solution and 0.050 g LiOH overnight. The reaction mixture was conc'd in vacuo, taken up in 8 ml of water, the pH of the solution was adjusted to 10 and the mixture extracted twice with 6-ml portions of CH$_2$Cl$_2$. The water layer was acidified with conc'd HCl and the resultant precipitate collected by suction filtration to give 0.024 g (20% yield). (MH$^+$=433.08)

The following compounds were made in an analogous manner.

Example 21a: 2-(S)-[4-(2,6-Dioxo-1,3-dipropyl-2,3,6,7-tetrahydro-1H-purin-8-yl)-bicyclo[2.2.2]oct-1-yloxy]-propionic acid, (MH$^+$=433.10)

Example 21b: 8-(4-Isopropoxy-bicyclo[2.2.2]oct-1-yl)-1,3-dipropyl-3,7-dihydro-purine-2.6-dione, (MH$^+$=403.13)

Example 21c: 8-(4-Allyloxy-bicyclo[2.2.2]oct-1-yl)-1,3-dipropyl-3,7-dihydro-purine-2.6-dione, (MH$^+$=401.11)

Example 21d: [4-(2,6-Dioxo-1,3-dipropyl-2,3,6,7-tetrahydro-1H-purin-8-yl)-bicyclo[2.2.2]oct-1-yloxy]-acetic acid, (MH$^+$=419.08)

Example 21e: 1,3-Dipropyl-8-[4-(2,2,2-trifluoro-1-trifluoromethyl-ethoxy)-bicyclo[2.2.2]oct-1-yl]-3,7-dihydro-purine-2,6-dione, (MH$^+$=511.00)

Example 21f: 2-[4-(2,6-Dioxo-1,3-dipropyl-2,3,6,7-tetrahydro-1H-purin-8-yl)-bicyclo[2.2.2]oct-1-yloxy]-2-methyl-propionic acid, (MH$^+$=447.17)

Example 21g: 3-[4-(2,6-Dioxo-1,3-dipropyl-2,3,6,7-tetrahydro-1H-purin-8-yl)-bicyclo[2.2.2]oct-1-yloxy]-propionic acid, (MH$^+$=433.6)

Example 21h: 3-(R)-[4-(2,6-Dioxo-1,3-dipropyl-2,3,6,7-tetrahydro-1H-purin-8-yl)-bicyclo[2.2.2]oct-1-yloxy]-butyric acid, (MH$^+$=447.34)

Example 21i: 3-(S)-[4-(2,6-Dioxo-1,3-dipropyl-2,3,6,7-tetrahydro-1H-purin-8-yl)-bicyclo[2.2.2]oct-1-yloxy]-butyric acid, (MH$^+$=447.33)

Example 21j: 3-[4-(2,6-Dioxo-1,3-dipropyl-2,3,6,7-tetrahydro-1H-purin-8-yl)-bicyclo[2.2.2]oct-1-yloxyl-2 (S)-methyl-propionic acid, MH$^+$=447.32)

Example 21k: 3-[4-(2,6-Dioxo-1,3-dipropyl-2,3,6,7-tetrahydro-1H-purin-8-yl)-bicyclo[2.2.2]oct-1-yloxy]-2 (R)-methyl-propionic acid, MH$^+$=447.33)

Example 21l: 3-[4-(2,6-Dioxo-1,3-dipropyl-2,3,6,7-tetrahydro-1H-purin-8-yl)-bicyclo[2.2.2]oct--yloxy]-2,2-dimethyl-propionic acid, (MH$^+$=461.32)

Example 21m: [5-(2,6-Dioxo-1,3-dipropyl-2,3,6,7-tetrahydro-1H-purin-8-yl)-bicyclo[3.2.2]non-1-yloxy]-acetic acid, (MH$^+$=433.3)

Example 21n: 3-[4-(2,6-Dioxo-1,3-dipropyl-2,3,6,7-tetrahydro-1H-purin-8-yl)-bicyclo[2.2.2]oct-1-ylmethoxy]-2,2-dimethyl-propionic acid, $^1$H NMR (400 MHz, CDCl$_3$):δ=0.86 (t, 6H), 1.15 (m, 6H), 1.45 (m, 6H), 1.58 (td, 2H), 1.67 (td, 2H), 1.84 (m, 6H), 3.32 (s, 2H), 3.38 (s, 2H), 3.90 (t, 2H), 3.98 (t, 2H).

Example 21o: 3-[5-(2,6-Dioxo-1,3-dipropyl-2,3,6,7-tetrahydro-1H-purin-8-yl)-bicyclo[3.2.2]non-1-yloxy]-propionic acid, (MH$^+$=447.32)

Example 21p: 2-(R)-[5-(2,6-Dioxo-1,3-dipropyl-2,3,6,7-tetrahydro-1H-purin-8-yl)-bicyclo[3.2.2]non-1-yloxy]-propionic acid, (MH$^+$=447.26)

Example 22

8-(4-Phenoxy-bicyclo[2.2.2]oct-1-yl)-1,3-dipropyl-3,7-dihydro-purine-2,6-dione

To a solution of 60 mg of 8-(4-Hydroxy-bicyclo[2.2.2]oct-1-yl)-1,3-dipropyl-3,7-dihydro-purine-2,6-dione (Example 13a) (0.167 mmol) in CH$_2$Cl$_2$ (2 ml) was added 27 μL of pyridine and the reaction mixture cooled to 0° C. To this was added 40 μL of triflic anhydride (0.24 mmol) in CH$_2$Cl$_2$ (1 ml). Maintained at 10° C. overnight. The reaction mixture was diluted with CH$_2$Cl$_2$ (5 ml) and washed with cold 1N HCl, sat'd NaHCO$_3$ and brine. Dried over sodium sulfate and concentrated in vacuo to afford a yellow oil. The crude triflate was dissolved in 1,4-dioxane (3 ml) and 100 mg of phenol (1.08 mmol was added followed by heating at 80° C. overnight. The reaction mixture was concentrated down and the residue taken up in ethyl acetate (10 ml) washed with 1N KOH (5 ml), sat'd NaHCO$_3$ (5 ml), 1N HCl (5 ml) and brine. The organic layer was dried over NaSO$_4$ and concentrated in vacuo to a colorless oil which was purified by column chromatography (SiO$_2$, 1:1 hexanes/EtOAc) to afford 11 mg of title compound as a white solid (MH$^+$=437.29). The following compounds were prepared in an analogous manner after saponification of the methyl ester.

Example 22a: [4-(2,6-Dioxo-1,3-dipropyl-2,3,6,7-tetrahydro-1H-purin-8-yl)-bicyclo[2.2.2]oct-1-ylsulfanyl]-acetic acid, (MH$^+$=435.35)

Example 22b: {[4-(2,6-Dioxo-1,3-dipropyl-2,3,6,7-tetrahydro-1H-purin-8-yl)-bicyclo[2.2.2]oct-1-yl]-methyl-amino}-acetic acid, (MH$^+$=432.31)

Example 22c: [4-(2,6-Dioxo-1,3-dipropyl-2,3,6,7-tetrahydro-1H-purin-8-yl)-bicyclo[2.2.2]octane-1-sulfonyl]-acetic acid, (MH$^+$=467.31)

Example 23

Methanesulfonic acid 4-(2,6-dioxo-1,3-dipropyl-2,3,6,7-tetrahydro-1H-purin-8-yl)-bicyclo[2.2.2]oct-1-yl ester To a solution of 50 mg of 8-(4-Hydroxy-bicyclo[2.2.2]oct-1-yl)-1,3-dipropyl-3,7-dihydro-purine-2,6-dione (Example 13a) (0.14 mmol) in CH$_2$Cl$_2$ (5 ml) was added 20 μL of Et$_3$N and the reaction mixture cooled in an ice bath. To this was added 20 μL of methanesulfonyl chloride (0.26 mmol) and the reaction mixture kept at 10° C. overnight. The reaction mixture was concentrated in vacuo and the residue taken up in EtOAc and washed 2× with dilute HCl (5 ml). The organic layer was dried over NaSO$_4$ and conc'd. The residue was triturated in acetonitrile to afford 36 mg (59%) of pure white solid (MH$^+$=439.4).

Example 24

Toluene-4-sulfonic acid 4-(2,6-dioxo-1,3-dipropyl-2,3,6,7-tetrahydro-1H-purin-8-yl)-bicyclo(2.2.2)oct-1-yl ester To a solution of 100 mg of 8-(4-Hydroxy-bicyclo[2.2.2]oct-1-yl)-1,3-dipropyl-3,7-dihydro-purin-2,6-dione (Example 13a) (0.28 mmol) in CH$_2$Cl$_2$ (10 ml) was added 40 μL of Et$_3$N and the reaction mixture cooled in an ice bath. To this was added 100 mg of p-toluenesulfonyl chloride (0.52 mmol) and the reaction kept at 10° C. overnight. The reaction mixture was conc'd in vacuo and the residue taken up in EtOAc and washed 2× with dilute HCl (10 ml). The organic layer was dried over NaSO$_4$ and conc'd. The residue was triturated in acetonitrile to afford 78 mg (54%) of pure white solid (MH$^+$=515.10).

Example 25

N-[4-(2,6-Dioxo-1,3-dipropyl-2,3,6,7-tetrahydro-1H-purin-8-yl)-bicyclo[2.2.2]oct-1-yl]-methanesulfonamide To a solution 100 mg of 8-(4-Amino-bicyclo[2.2.2]oct-1-yl)-1,3-dipropyl-3,7-dihydro-purine-2,6-dione (Example 20), (0.28 mmol) in 2 ml of pyridine chilled in an ice/water bath was added 22 μL of methanesulfonyl chloride (0.28 mmol), 30% completion after 24 h at 10° C. Two more aliquots (22 μL and 50 μL) of methanesulfonyl chloride were added to drive the reaction to completion. The reaction mixture was concentrated in vacuo to afford a yellow oil which was taken up in EtOAc (10 ml) and washed twice with sat'd NaHCO$_3$ (5 ml), once with 0.5N HCl and once with brine. The organic layer was dried over NaSO$_4$ and conc'd to an oil. Crystallized from acetonitrile to afford 27 mg (22%) as a white solid (MH$^+$=438.08). The following compounds were prepared in an analogous manner:

Example 25a: 3-[4-(2,6-Dioxo-1,3-dipropyl-2,3,6,7-tetrahydro-1H-purin-8-yl)-bicyclo[2.2.2]oct-1-ylsulfamoyl]-benzenesulfonic acid, (MH$^+$=579.95)

Example 25b: [4-(2,6-Dioxo-1,3-dipropyl-2,3,6,7-tetrahydro-1H-purin-8-yl)-bicyclo[2.2.2]oct-1-ylsulfamoyl]-acetic acid, (MH$^+$=482.27)

Example 25c: 3-[4-(2,6-Dioxo-1,3-dipropyl-2,3,6,7-tetrahydro-1H-purin-8-yl)-bicyclo[2.2.2]oct-1-ylsulfamoyl]-thiophene-2-carboxylic acid methyl ester, (MH$^+$=564.19)

Example 25d: 3-[4-(2,6-Dioxo-1,3-dipropyl-2,3,6,7-tetrahydro-1H-purin-8-yl)-bicyclo[2.2.2]oct-1-ylsulfamoyl]-thiophene-2-carboxylic acid, (MH$^+$=550.20)

Example 25e: N-[4-(2,6-Dioxo-1,3-dipropyl-2,3,6,7-tetrahydro-1H-purin-8-yl)-bicyclo[2.2.2]oct-1-ylmethyl]-methanesulfonamide, (MH$^+$=388.32)

Example 25f: 3-{[4-(2,6-Dioxo-1,3-dipropyl-2,3,6,7-tetrahydro-1H-purin-8-yl)-bicyclo[2.2.2]oct-1-ylmethyl]-sulfamoyl}-thiophene-2-carboxylic acid methyl ester, (MH$^+$=578.3)

Example 25g: 3-{[4-(2,6-Dioxo-1,3-dipropyl-2,3,6,7-tetrahydro-1H-purin-8-yl)-bicyclo[2.2.2]oct-1-ylmethyl]-sulfamoyl}-thiophene-2-carboxylic acid, (MH$^+$=564.24)

Example 25h: [4-(2,6-Dioxo-1,3-dipropyl-2,3,6,7-tetrahydro-1H-purin-8-yl)-bicyclo[2.2.2]oct-1-ylcarbamoyl]-methanesulfonic acid, (MH$^+$=480.13)

Example 26

1,3-Dipropyl-8-{4-[(thiophen-2-ylmethyl)-aminol-bicyclo[2.2.2]oct-1-yl}-3,7-dihydro-purine-2,6-dione To a solution of 100 mg of 8-(4-Amino-bicyclo[2.2.2]oct-1-yl)-1,3-dipropyl-3,7-dihydro-purine-2,6-dione (Example 20) (0.28 mmol) and 37 mg of thiophene-2-carboxaldehyde (0.33 mmol) in CH$_2$Cl$_2$ (5 ml) was added 5 drops of glacial acetic acid and 100 mg of sodium triacetoxyborohydride (0.47 mmol). Complete conversion occurs over 24 h at rt. The reaction mixture was quenched with 2 ml of ethanol and 2 ml of 2N HCl and then concentrated in vacuo to afford a colorless oil which was purified from anhydrous acetonitrile to afford 50.8 mg (40%) as a white solid (MH$^+$=456.29). The following compounds were prepared in an analogous manner:

Example 26a: {[4-(2,6-Dioxo-1,3-dipropyl-2,3,6,7-tetrahydro-1H-purin-8-yl)-bicyclo[2.2.2]oct-1-ylmethyl]-amino}-acetic acid, (MH$^+$=432.32)

Example 26b: 8-{4-[(1H-Imidazol-2-ylmethyl)-amino]-bicyclo[2.2.2]oct-1-yl}-1,3-dipropyl-3,7-dihydro-purine-2,6-dione, (MH$^+$=440.09)

Example 26c: [4-(2,6-Dioxo-1,3-dipropyl-2,3,6,7-tetrahydro-1H-purin-8-yl)-bicyclo[2.2.2]oct-1-ylamino]-acetic acid, (MH$^+$=418.15)

Example 26d: 8-{4-[(Furan-2-ylmethyl)-amino]-bicyclo[2.2.2]oct-1-yl}-1,3-dipropyl-3,7-dihydro-purine-2,6-dione, (MH$^+$=440.30)

Example 26e: 1,3-Dipropyl-8-(4-{[(thiophen-2-ylmethyl)-amino]-methyl}-bicyclo[2.2.2]oct-1-yl)-3,7-dihydro-purine-2,6-dione, (MH$^+$=470.31)

Example 26f: 8-(4-{[(3H-Imidazol-4-ylmethyl)-amino]-methyl}-bicyclo[2.2.2]oct-1-yl)-1,3-dipropyl-3,7-dihydro-purine-2,6-dione, (MH$^+$=454.35)

Example 26g: 4-{[4-(2,6-Dioxo-1,3-dipropyl-2,3,6,7-tetrahydro-1H-purin-8-yl)-bicyclo[2.2.2]oct-1-ylamino]-methyl}-benzoic acid, (MH$^+$=494.34)

Example 26h: 4-({[4-(2,6-Dioxo-1,3-dipropyl-2,3,6,7-tetrahydro-1H-purin-8-yl)-bicyclo[2.2.2]oct-1-ylmethyl]-aminol-methyl)-benzoic acid, (MH$^+$=508.31)

Example 26i: 1,3-Dipropyl-8-(4-{[(pyridin-4-ylmethyl)-amino]-methyl}-bicyclo[2.2.2]oct-1-yl)-3,7-dihydro-purine-2,6-dione, (MH$^+$=465.33)

Example 26j: 8-(4-{[(Furan-2-ylmethyl)-amino]-methyl}-bicyclo[2.2.2]oct-1-yl)-1,3-dipropyl-3,7-dihydro-purine-2,6-dione, (MH$^+$=454.3 3)

Example 26k: 5-{[4-(2,6-Dioxo-1,3-dipropyl-2,3,6,7-tetrahydro-1H-purin-8-yl)-bicyclo[2.2.2]oct-1-ylamino]-methyl}-furan-2-sulfonic acid, (MH$^+$=520.26)

Example 26l: 8-(4-Cyclopentylamino-bicyclo[2.2.2]oct-1-yl)-1,3-dipropyl-3,7-dihydro-purine-2,6-dione, (MH$^+$=428.38)

Example 26m: 8-(4-Cyclopentylaminomethyl-bicyclo[2.2.2]oct-1-yl)-1,3-dipropyl-3,7-dihydro-purine-2,6-dione, (MH$^+$=442.56)

Example 26n: 8-{4-[(1-Methyl-butylamino)-methyl]-bicyclo[2.2.2]oct-1-yl}-1,3-dipropyl-3,7-dihydro-purine-2,6-dione, (MH$^+$=444.60)

Example 27

4-[3-(4-Hydroxy-phenyl)-2,6-dioxo-1-propyl-2,3,6,7-tetrahydro-1H-purin-8-yl]-bicyclo[2.2.2]octane-1-carboxylic acid To a solution of 10 mg of 4-[3-(4-Methoxy-phenyl)-2,6-dioxo-1-propyl-2,3,6,7-tetrahydro-1H-purin-8-yl]-bicyclo[2.2.2]octane-1-carboxylic (Example 131) (0.022 mmol) in CH$_2$Cl$_2$ (2 ml) cooled in a dry ice/acetone bath was added 1 ml of 1M boron tribromide (1 mmol) in CH$_2$Cl$_2$. The reaction mixture was allowed to come to rt. and maintained for 2 h. After this time the reaction mixture was cooled in dry ice and quenched with MeOH. The crude product was isolated after concentration in vacuo and recrystallized from acetonitrile to afford 10 mg of a white solid (MH$^+$=439.09). The following compounds were prepared in a similar manner.

Example 27a: 4-{3-[2-(4-Hydroxy-phenyl)-ethyl]-2,6-dioxo-1-propyl-2,3,6,7-tetrahydro-1H-purin-8-yl}-bicyclo[2.2.2]octane-1-carboxylic acid, (MH$^+$=467.4)

Example 27b: 4-[3-(2-Hydroxy-ethyl)-2,6-dioxo-1-propyl-2,3,6,7-tetrahydro-1H-purin-8-yl]-bicyclo[2.2.2]octane-1-carboxylic acid, (MH$^+$=391.12)

Example 27c: 4-[3-(4-Hydroxy-phenyl)-2,6-dioxo-1-propyl-2,3,6,7-tetrahydro-1H-purin-8-yl]-bicyclo[2.2.2]octane-1-carboxylic acid. (MH$^+$=439.09)

Example 27d: 27d: 3-(4-{3-[2-(4-Hydroxy-phenyl)-ethyl]-2,6-dioxo-1-propyl-2,3,6,7-tetrahydro-1H-purin-8-yl}-bicyclo(2.2.2]oct-1-yl)-propionic acid, (MH$^+$=495.12)

Example 27e: 8-(4-Hydroxy-bicyclo[2.2.2]oct-1-yl)-3-[2-(4-hydroxy-phenyl)-ethyl]-1-propyl-3,7-dihydro-purine-2,6-dione, (MH$^+$=439.14)

Example 28

4-{3-[2-(4-Hydroxy-3-iodo-phenyl)-ethyl]-2,6-dioxo-1-propyl-2,3,6,7-tetrahydro-1H-purin-8-yl}-bicyclo[2.2.2]octane-1-carboxylic acid To a solution of 50 mg 4-{3-[2-(4-Hydroxy-phenyl)-ethyl]-2,6-dioxo-1-propyl-2,3,6,7-tetrahydro-1H-purin-8-yl}-bicyclo[2.2.2]octane-1-carboxylic acid (Example 27a) (0.107 mmol) in water (10 ml) containing 1 eq. of 1N NaOH (110 μL) was added at rt a solution of 30 mg of iodine (0.107 mmol) in ethanol (1 ml). The reaction mixture was concentrated in vacuo and the crude product purified by preparative chromatography to afford 12 mg (20%) of desired product (MH$^+$=592.89).

The following compounds were prepared in a similar manner.

Example 28a: 4-{3-[2-(4-Hydroxy-3,5-diiodo-phenyl)-ethyl]-2,6-dioxo-1-propyl-2,3,6,7-tetrahydro-1H-purin-8-yl}-bicyclo[2.2.2]octane-1-carboxylic acid, (MH$^+$=718.50)

Example 28b: 3-(4-{3-[2-(4-Hydroxy-3-iodo-phenyl)-ethyl]-2,6-dioxo-1-propyl-2,3,6,7-tetrahydro-1H-purin-8-yl}-bicyclo[2.2.2]oct-1-yl)-propionic acid, (MH$^+$=621.08)

Example 29

4-(2,6-Dioxo-1,3-dipropyl-2,3,6,7-tetrahydro-1H-purin-8-yl)-bicyclo[2.2.2]octane-1-carboxylic acid amide To a solution of 200 mg of 4-(2,6-Dioxo-1,3-dipropyl-2,3,6,7-tetrahydro-1H-purin-8-yl)-bicyclo[2.2.2]octane-1-carboxylic acid (Example 13) (0.515 mmol) in 5 ml of DMF was added 235 mg of HATU (0.618 mmol) and 0.4 ml of N,N-diisopropylethyl amine. Let stir at rt for 30 min. Added 2.1 ml of 0.5 M NH$_3$ in dioxane (1.03 mmol) dropwise over 5 min. Let stir overnight added 0.5 eq. of 0.5M NH$_3$ in dioxane (0.5 ml). Added EtOAc and 1N NaOH until pH=9 and washed with 10% citric acid, sat'd NaHCO$_3$ and brine. Dried over NaSO$_4$ and conc'd in vacuo to afford 80.9 mg (40%) of pure product (MH$^+$=388.34).

Example 30

8-(4-Aminomethyl-bicyclo[2.2.2]oct-1-yl)-1,3-dipropyl-3,7-dihydro-purine-2,6-dione To a solution of 50 mg of: 4-(2,6-Dioxo-1,3-dipropyl-2,3,6,7-tetrahydro-1H-purin-8-yl)-bicyclo[2.2.2]octane-1-carboxylic acid amide (Example 29) (0.129 mmol) in THF (10 ml) was added dropwise at rt 0.28 ml of 1M borane-THF complex (0.284 mmol) and slowly brought to reflux after the addition was complete. Refluxed for 3.5 h then cooled and quenched with 10 ml of methanol and brought to reflux. Concentrated in vacuo and the residue taken up in 1N HCl and washed twice with CH$_2$Cl$_2$ Adjusted pH 8 and washed twice with EtOAc, dried over NaSO$_4$ and conc'd in vacuo to afford 30.2 mg (63%) of amine (MH$^+$=374.31).

Example 31

5-(2,6-Dioxo-1,3-dipropyl-2,3,6,7-tetrahydro-1H-purin-8-yl)-bicyclo-[3.2.1]octane-2-carboxylic acid Using the procedure described in the references, Kraus, W., et al. *Liebigs Ann. Chem.* 1981, 10, 1826, and Kraus,. W., et al. *Tetrahedron Lett.* 1978, 445; Filippini, M.-H. et al. *J. Org. Chem.* 1995, 60, 6872, 4-oxo-bicyclo[3.2.1]octane-1-carboxylic acid ethyl ester (6.17 mmol, 1.21 g) was converted to 4-methoxymethylene-bicyclo[3.2.1]octane-1-carboxylic acid ethyl ester. Flash chromatography, eluting with 10% diethyl ether/hexanes provided pure product (0.96 g, 69%) as a liquid (mixture of E/Z isomers). $^{13}$C NMR (100 MHz, CDCl$_3$): 14.31 (q), 19.15 (t), 22.97 (t), 23.61 (t), 23.91 (t), 29.97 (t), 31.13 (t), 32.04 (t), 32.36 (t), 34.61 (t), 34.85

(d), 35.81 (t), 43.18 (t), 43.63 (t), 50.47 (s), 50.77 (s), 59.63 (q), 59.69 (t), 121.04 (s), 121.44(s), 137.18 (d), 138.16 (d), 177.60 (s), 177.63 (s).

Using the procedure described in Example 50, 4-methoxymethylene-bicyclo[3.2.1]octane-1-carboxylic acid ethyl ester (3.84 mmol, 0.86 g) was converted to 4-formyl-bicyclo[3.2.1]octane-1-carboxylic acid ethyl ester (0.81 g, 100%). TLC(silica, 20% $Et_2O$/hexanes, 20% PMA/EtOH visualization) $R_f$ (title compound)=0.29.

To an ice-cold solution of 4-formyl-bicyclo[3.2.1]octane-1-carboxylic acid ethyl ester (3.85 mmol, 0.81 g) was added slowly Jones reagent (2.7 M, 1.43 mL). The reaction was stirred at ice temperature 20 min, then quenched by addition of iPrOH. diluted with $H_2O$ and extracted with $Et_2O$ (3×). The combined organic extracts were washed with $H_2O$ (2×), brine (1×), and dried ($MgSO_4$). Filtration and evaporation provided the viscous oily bicyclo[3.2.1]octane-1,4-dicarboxylic acid 1-ethyl ester (0.76 g, 87%) as a mixture of axial and equatorial acids. $^{13}C$ NMR (100 MHz, $CDCl_3$): 14.16 (q), 19.86 (t), 21.07 (t), 25.98 (t), 29.20 (t), 31.52 (t), 31.87 (t), 32.27 (t), 33.39 (t), 37.80 (d), 38.07 (t), 38.10 (d), 42.06 (t), 44.80 (d), 45.78 (d), 49.38 (s), 49.60 (s), 60.31 (t), 60.36 (t), 177.08 (s), 180.01 (s).

At 0° C., a solution of DCC (0.5 M in $CH_2Cl_2$, 5.5 ml) was added to a solution of bicyclo[3.2.1]octane-1,4-dicarboxylic acid 1-ethyl ester (2.52 mmol, 0.57 g), t-BuOH (7.56 mmol, 0.56 g) and DMAP (2.02 mmol, 0.247 g) in $CH_2Cl_2$ (15 ml). After stirring overnight at RT, the reaction was filtered to remove solids and the filtrate was washed with 5% citric acid, saturated $NaHCO_3$, and dried ($MgSO_4$). Filtration and evaporation yielded product (0.71 g, 100%) as an oil. MS ($ES^+$) 225.24 (M+H−tBu).

A solution of bicyclo[3.2.1]octane-1,4-dicarboxylic acid 4-tert-butyl ester 1-ethyl ester (2.52 mmol, 0.71 g) in THF (12 ml) was treated with 1N LiOH (12.6 ml) and stirred at room temperature 3 d. The reaction was concentrated to remove THF and the aqueous residue extracted with $Et_2O$ to remove neutral impurities. The aqueous phase was acidified (pH 2–3) at 0° C. with 1N HCl and then promptly extracted with EtOAc. The combined organics were washed with $H_2O$, brine, and dried ($MgSO_4$). Filtration and evaporation yielded product (0.48 g, 75%).

Using the procedure described in Example 8, bicyclo[3.2.1]octane-1,4-dicarboxylic acid 4-tert-butyl ester (1.89 mmol, 0.48 g) was reacted with 5,6-diamino-1,3-dipropyl-1H-pyrimidine-2,4-dione hydrochloride (1.89 mmol, 0.597 g) to give product (0.81 g, 93%). MS ($ES^+$): 463.14 (M+H)

Using the procedure described in Example 8, 5-(6-amino-2,4-dioxo-1,3-dipropyl-1,2,3,4-tetrahydro-pyrimidin-5-ylcarbamoyl)-bicyclo[3.2.1]octane-2-carboxylic acid tert-butyl ester (1.75 mmol, 0.81 g) was converted to product (0.501 g, 70%).

A solution of 5-(2,6-dioxo-1,3-dipropyl-2,3,6,7-tetrahydro-1H-purin-8-yl)-bicyclo-[3.2.1]octane-2-carboxylic acid tert-butyl ester (1.13 mmol, 0.501 g) in $CH_2Cl_2$ (5 ml) was treated with TFA (5 ml). After stirring overnight at RT, the reaction was concentrated to dryness. Reverse phase HPLC to provide separation of the equatorial (first band, 0.010 g) and axial (second band, 0.010 g) acid isomers. HPLC (10% to 90% MeCN (0.1% TFA)/H2O (0.1% TFA), YMC 120 A/S-5 ODS-AM column, 100 mm×4.6 mm, 1.5 ml/min: $R_T$ (equatorial)=6.49 min; $R_T$ (axial)=6.75.

Example 32

3-[5-(2,6-Dioxo-1,3-dipropyl-2,3,6,7-tetrahydro-1H-purin-8-yl)-bicyclo[3.2.1]oct-1-yl]-propionic acid A suspension of 3-[5-(2,6-Dioxo-1,3-dipropyl-2,3,6,7-tetrahydro-1H-purin-8-yl)-bicyclo-[3.2.1]oct-1-yl]-acrylic acid methyl ester (Example 12) (0.58 mmol, 0.25 g) and 10% Pd/C (50% $H_2O$, 0.029 mmol, 0.062 g) in MeOH (20 ml) was hydrogenated at 40 psi overnight. The completed reaction was filtered through Celite, rinsing with MeOH. Evaporation provided the desired product (0.196 g, 79%) as an oil. MS ($ES^+$) 431.18 (M+H)

A solution of 3-[5-(2,6-dioxo-1,3-dipropyl-2,3,6,7-tetrahydro-1H-purin-8-yl)-bicyclo-[3.2.1]oct-1-yl]-propionic acid methyl ester (0.456 mmol, 0.196 g) in THF (10 ml) was treated with 20% NaOH (2 ml) and stirred overnight at RT. The reaction was concentrated to remove the THF. The aqueous residue was acidified (pH 2–3) with conc. HCl and iPrOH was added to homogeneity. The solution was concentrated on the rotovap until solids just began to separate. After chilling in ice 1 h, the precipitated solids were collected by vacuum filtration, rinsed with a little $H_2O$ and chased with $Et_2O$. The solids were dried on the filter to provide the desired product (0.061 g, 32%). $^{13}C$ NMR (100 MHz, $CDCl_3$): 11.11 (q), 11.26 (q), 20.04 (t), 21.25 (t), 21.31 (t), 29.51 (s), 33.97 (t), 35.15 (s), 36.16 (t), 36.39 (t), 43.32 (t), 43.41 (t), 45.38 (t), 49.18 (t), 106.01 (s), 149.40 (s), 150.90 (s), 156.30 (s), 161.56 (s), 178.54 (s).

Example 33

(1RS,2R,5SR)-{[5-(2,6-Dioxo-1,3-dipropyl-2,3,6,7-tetrahydro-1H-purin-8-yl)-bicyclo[3.2.1]octane-1-carbonyl]-amino}-phenylacetic acid Using the procedure described in Example 8, 5-(2,6-Dioxo-1,3-dipropyl-2,3,6,7-tetrahydro-1H-purin-8-yl)-bicyclo[3.2.1]octane-1-carboxylic acid (Example 8) (0.052 mmol, 0.020 g) and (R)-phenylglycine methyl ester hydrochloride (0.064 mmol, 0.013 g) were reacted to produce the title compound (0.0134 g, 48%) as a mixture of diastereomers. MS ($ES^+$) 536.36 (M+H)

A solution of (1RS,2R,5SR)-{[5-(2,6-Dioxo-1,3-dipropyl-2,3,6,7-tetrahydro-1H-purin-8-yl)-bicyclo-[3.2.1] octane-1-carbonyl]-amino}-phenyl-acetic acid methyl ester (0.022 mmol, 0.012 g) in THF (2 ml) was treated with 1N LiOH (0.22 ml) for 3d. The THF was removed on the rotovap, the aqueous residue acidified (pH 2) with 1N HCl and extracted with EtOAc. The combined organics were washed with $H_2O$, brine and dried ($MgSO_4$). Filtration and evaporation followed by reverse phase HPLC purification provide the desired product (0.0055 g, 48%) as a mixture of diastereomers. HPLC (10% to 90% MeCN (0.1% TFA)/$H_2O$ (0.1% TFA), YMC 120 A/S-5 ODS-AM column, 100 mm×4.6 mm, 1.5 ml/min: $R_T$=6.88 min.

The following compound was prepared in an analogous manner:

Example 33a: (1RS,2S,5SR)-{[5-(2,6-Dioxo-1,3-dipropyl-2,3,6,7-tetrahydro-1H-purin-8-yl)-bicyclo[3.2.1]octane-1-carbonyl]-amino}-phenylacetic acid Example 34

8-(4-Hydroxy-bicyclo[3.2.1]oct-1-yl)-1,3-dipropyl-3,7-dihydro-purine-2,6-dione

Using the method described in Example 8, 4-hydroxy-bicyclo[3.2.1]octane-1-carboxylic acid (Kraus, W., et al. *Liebigs Ann. Chem.*, 1981, 10, 1826) (0.50 mmol, 0.085 g) was reacted with 5,6-diamino-1,3-dipropyl-1H-pyrimidine-2,4-dione hydrochloride (0.50 mmol, 0.132 g) to provide the desired product (0.081 g, 44%).

Using the method described in Example 8, 4-hydroxy-bicyclo[3.2.1]octane-1-carboxylic acid (6-amino-2,4-dioxo- 1,3-dipropyl-1,2,3,4-tetrahydro-pyrimidin-5-yl)-amide (0.21 mmol, 0.081 g) wvas converted to the desired product. MS (ES$^+$) 361.36 (M+H).

Example 35

3-[4-(2,6-Dioxo-1,3-dipropyl-2,3,6,7-tetrahydro-1H-purin-8-yl)-2-oxa-bicyclo[2.2.2]oct-1-yl]-propionic acid Vinylmagnesium bromide (1.0 M in THF, 100 ml) was cooled to 0° C. and the ditosylate derivative of 4,4-bis-hydroxy concentrated under reduced pressure. Purification by chromatography (1:1 hex/EtOAc) afforded 5.0 g of the intermediate alcohol.

This material (5.0 g) was dissolved in 200 ml of anhydrous DME and 730 mg of NaH (3 eq) was added. The reaction mixture was stirred under reflux for 18 h. It was then cooled to rt and quenched with sat aq $NH_4Cl$ and extracted with EtOAc. The organic layer was dried ($Na_4SO_4$) and concentrated to afford 3.30 g of the monotosylate intermediate.

This monotosylate (4.40 g, 13.7 mmol) was dissolved in 20 ml of DMSO and NaOAc.3 $H_2O$ (18.0 g, 10 eq) was added. The reaction mixture was stirred at 60° C. for 2 days. It was then diluted with $H_2O$ and extracted with EtOAc. The organic layer was washed with $H_2O$, dried ($Na_2SO_4$) and concentrated to afford 2.60 g of the acetate derivative, acetic acid 1-vinyl-2-oxa-bicyclo[2.2.2]oct-4-ylmethyl ester.

This acetate (2.60 g, 12.4 mmol) was dissolved in 40 ml of MeOH and $K_2CO_3$ (8.5 g, 5 eq) was added as a solution in 50 ml of $H_2O$. The reaction mixture was stirred at rt for 3 h. It was then concentrated and extracted with EtOAc. The organic layer was dried ($Na_2SO_4$) and concentrated. Purification by chromatography (2:1 EtOAc/hex) afforded 1.20 g of the alcohol derivative, (1-vinyl-2-oxa-bicyclo[2.2.2]oct-4-yl)-methanol.

This material (1.20 g, 7.14 mmol) was dissolved in 20 ml of acetone and cooled to 10° C. $CrO_3$ (2.1 g. 3 eq) was added as a solution in 10 ml of 1.5 N $H_2SO_4$ (aq). The reaction mixture was stirred at 10° C. for 15 min and warmed to rt and stirred for 45 min. It was then diluted with $H_2O$ and extracted with EtOAc. The combined organic layers were washed with $H_2O$ and then extracted with dilute aq KOH. The aqueous layer was acidified to pH 1 with conc HCl and extracted with EtOAc. The organic layer was dried ($Na_2SO_4$) and concentrated to afford 920 mg of the carboxylic acid derivative, 1-vinyl-2-oxa-bicyclo[2.2.2]octane-4-carboxylic acid.

This material was treated with 5,6-diamino-1,3-dipropyl-1H-pyrimidine-2,4-dione in the same manner as before to obtain the corresponding xanthine derivative, 1,3-dipropyl-8-(1-vinyl-2-oxa-bicyclo[2.2.9]oct-4-yl)-3,7-dihydro-purine-2,6-dione.

1,3-Dipropyl-8-(1-vinyl-2-oxa-bicyclo[2.2.2]oct-4-yl)-3,7-dihydro-purine-2,6-dione (400 mg, 1.08 mmol) was suspended in 8 ml of dioxane and 1 ml of a 2.5% solution of $OsO_4$ in t-BuOH was added, followed by 3 ml of $H_2O$. After 10 min, $NaIO_4$ was added and the reaction mixture was stirred at rt for 3 h. It was then diluted with $H_2O$ and extracted with EtOAc. The organic layer was dried ($Na_2SO_4$) and concentrated to afford the aldehyde intermediate, 4-(2,6-dioxo-1,3-dipropyl-2,3,6,7-tetrahydro-1H-purin-8-yl)-2-oxa-bicyclo[2.2.2]octane-1-carbaldehyde.

This material was dissolved in 8 ml of THF and methyl (triphenylphosphor-anyline)acetate (720 mg, 2 eq) was added. The reaction mixture was stirred at rt for 18 h. LiOH (155 mg, 6 eq) was added as a solution in 8 ml of $H_2O$ and the resulting reaction mixture was stirred at rt for 4 h. The reaction was then extracted with EtOAc. The organic layer was dried ($Na_2SO_4$) and concentrated to afford 250 mg of the acrylate derivative, 3-[4-(2,6-dioxo-1,3-dipropyl-2,3,6,7-tetrahydro-1H-purin-8-yl)-2-oxa-bicyclo[2.2.2]oct-1-yl]-acrylic acid.

This material was dissolved in 25 ml of 95% THF and 5% $H_2O$. 10% Pd/C (80 mg) was added and the reaction mixture was hydrogenated under 50 psi of $H_2$ for 3 h. The reaction mixture was filtered through a pad of Celite and the filtrate was concentrated. Purification by preparative HPLC using aq $CH_3CN$ afforded the titled compound. MS (ES$^+$) 419.

Example 36

3-(2,6-Dioxo-1,3-dipropyl-2,3,6,7-tetrahydro-1H-purin-8-yl)-adamantane-1-carboxylic acid 4-aminomethyl-benzylamide Step 1
Wang resin (10 g, from Advanced ChemTech, substitution 0.7 mmols/g) in 100 ml of dry THF was added CDI (10 g) and the resin was shaken overnight. Next day the resin was filtered and washed with THF (3×100 ml) and dried.
Step 2
Resin (2.5 g each, 1.75 mmol) from step 1 was treated with eight different diamines (8.75 mmol, 5 eq) in THF (25 ml). For this example, 4-Aminomethyl-benzylamine was used. After shaking overnight the resin was washed with THF (3×25 ml), MeOH (3×25 ml). $CH_2Cl_2$ (3×25 ml) MeOH (3×25 ml) and dried.
Step 3
Adamantane-1,3-dicarboxylic acid (3.5 g) was taken in DMF (20 ml) DIC (1.36 ml) was added and stirred for 1 hr. The resulting anhydride was added to the resin from step 2. The resin was shaken overnight. Next day the resin was filtered, washed with DMF (3×25 ml), $CH_2Cl_2$ (3×25 ml) MeOH (3×25 ml) and dried.
Step 4
1,3 dipropyl-5,6-diaminouracil.HCl was coupled to the resin from step 3 using PyBOP, N-methyl morpholine in DMF overnight. The resin was washed with DMF (3×25 ml), $CH_2Cl_2$ (3×25 ml) MeOH (3×25 ml) and dried.
Step 5
To the resin from step 4 was added 2 ml of KOH solution (7.5 g of KOH in 200 ml of water:MeOH:THF 10:90:100, 10 eq) and heated at 60° C. overnight. Next day, after cooling to rt, he resin was washed with MeOH (3×2 ml), THF (3×2 ml), $CH_2Cl_2$ (3×2 ml) and dried. The resin was cleaved using 1:1 TFA: $CH_2Cl_2$ (2 ml) for 1 hr. The resin was filtered and washed with $CH_2Cl_2$. Combined solvent was removed by Speed Vac. The residue was dissolved in $CH_3CN$:water 1:1 (2 ml) and lyophilized. Products were characterized by LCMS. Mass (ES$^+$ 533).

Example 37

3-(2,6-Dioxo-1,3-dipropyl-2,3,6,7-tetrahydro-1H-purin-8-yl)-adamantane-1-carboxylic acid 3-aminomethyl-benzylamide Followed the procedure from Example 36. 3-Aminomethyl-benzylamine was used in step 2. Mass ((ES$^+$ 533).

Example 38

3-(2,6-Dioxo-1,3-dipropyl-2,3,6,7-tetrahydro-1H-purin-8-yl)-adamantane-1-carboxylic acid (3-aminopropyl)-amide Followed the procedure from Example 36. 1,3-Diaminopropane was used in step 2. Mass ((ES$^+$ 471).

Example 39

3-(2,6-Dioxo-1,3-dipropyl-2,3,6,7-tetrahydro-1H-purin-8-yl)-adamantane-1-carboxylic acid {3-[4-(3-amino-propyl)-piperazin-1-yl]-propyl}-amide Followed the procedure from Example 36. 3-[4-(3-Amino-propyl)-piperazin-1-yl]-propylamine was used in step 2. Mass (($ES^+$ 599).

Example 40

3-(2,6-Dioxo-1,3-dipropyl-2,3,6,7-tetrahydro-1H-purin-8-yl)-adamantane-1-carboxylic acid [4-(4-amino-cyclohexylmethyl)-cyclohexyl]-amide Followed the procedure from Example 36. 4,4'-Methylenebis(cyclohexylamine) was used in step 2. Mass (($ES^+$ 607).

Example 41

3-(2,6-Dioxo-1,3-dipropyl-2,3,6,7-tetrahydro-1H-purin-8-yl)-adamantane-1-carboxylic acid (4-amino-cyclohexyl)-amide Followed the procedure from Example 36. Cyclohexane-1,4-diamine was used in step 2. Mass (($ES^+$ 511).

Example 42

8-[3-(Piperazine-1-carbonyl)-adamantan-1-yl]-1,3-dipropyl-3,7-dihydro-purine-2,6-dione Followed the procedure from Example 36. Piperazine was used in step 2. Mass (($ES^+$ 483).

Example 43

3-(2,6-Dioxo-1,3-dipropyl-2,3,6,7-tetrahydro-1H-purin-8-yl)-adamantane-1-carboxylic acid amide Followed the procedure from Example 36 Step 3. Rink resin was used instead of wang resin. Mass ($ES^+$ 414).

Example 44

3-(2,6-Dioxo-1,3-dipropyl-2,3,6,7-tetrahydro-1H-purin-8-yl)-adamantane-1-carboxylic acid Symmetrical anhydride prepared from adamantane 1,3-dicarboxylic acid using DIC in DMF was coupled to 1,3-dipropyl-5,6-diaminouracil.HCl. The product was cyclized using KOH in isopropanol/water. Mass ($ES^+$ 415)

Example 45

8-(3-Hydroxymethyl-adamantan-1-yl)-1,3-dipropyl-3,7-dihydro-purine-2,6-dione

Followed the procedure from Example 46. Mass ($ES^+$ 401)

Example 46

5-(2,6-Dioxo-1,3-dipropyl-2,3,6,7-tetrahydro-1H-purin-8-yl)-bicyclo[3.3.1]nonane-1-carboxylic acid Bicyclo[3.3.1]nonane-1,5-dicarboxylic acid monomethyl ester (900 mg) was taken in $CH_2Cl_2$ (25 ml), oxalyl chloride (417 µl) and 2 drops of DMF were added and stirred at rt for 2 hrs. After two hrs, solvent was removed by rotavap. The residue was taken up in 20 ml of $CH_2Cl_2$. Diamino uracil-.HCl (1.25 g), and diisopropylethyl amine(1.7 ml) were added and stirred at rt overnight. Next day, the reaction mixture was diluted with water, extracted with $CH_2Cl_2$, washed with brine, dried over $Na_2SO_4$, and concentrated. The crude product was taken in isopropanol:water (2:1, 100 ml) and KOH (890 mg) was added and refluxed overnight. Next day after cooling to rt, solvent was removed by rotavap, diluted with water, acidified with 1N HCl. Precipitate formed was filtered and dried. Yield 900 mg. Mass ($ES^+$ 403)

Example 47

8-(5-Hydroxymethyl-bicyclo[3.3.1]non-1-yl)-1,3-dipropyl-3,7-dihydro-purine-2,6-dione 5-(2,6-Dioxo-1,3-dipropyl-2,3,6,7-tetrahydro-1H-purin-8-yl)-bicyclo[3.3.1]nonane 1-carboxylic acid (700 mg) was taken in THF (25 ml). $BH_3$.THF (1M, 3.5 ml) was added and stirred at rt overnight. Next day the reaction was quenched with MeOH. Solvent was removed by rotavap. Diluted with water and extracted with ethyl acetate, washed with water, brine, dried over $Na_2SO_4$ and concentrated. Yield 690 mg. Mass ($ES^+$ 389)

Example 48

8-{5-[(2-Dimethylamino-ethylamino)-methyl]-bicyclo[3.3.1]non-1-yl}-1,3-dipropyl-3,7-dihydro-purine-2,6-dione Step 1

8-(5-Hydroxymethyl-bicyclo[3.3.1]non-1-yl)-1,3-dipropyl-3,7-dihydro-purine-2,6-dione (690 mg) was taken in 50 ml of DMSO. Pyridine.$SO_3$ (844 mg) and triethylamine (1.6 ml) were added and stirred overnight. Additional amount of Pyridine.$SO_3$ (844) was addded and stirred overnight. The reaction mixture was diluted with ethyl acetate (100 ml) and washed with 1N HCl, water, brine, and dried over $Na_2SO_4$. After concentration, the crude product was taken to next step without purification.

Step 2

5-(2,6-Dioxo-1,3-dipropyl-2,3,6,7-tetrahydro-1H-purin-8-yl)-bicyclo[3.3.1]nonane-1-carbaldehyde (40 mg) taken in 5 ml of $CH_2Cl_2$.N1,N1-Dimethyl-ethane-1,2-diamine (40 mg), Na(OAc)$_3$BH (100 mg), 2 drops of Acetic acid were added and stirred at rt overnight. Next day the reaction mixture was diluted with ethyl acetate, washed with sat. $NAHCO_3$, brine and dried over $MgSO_4$. The solvent was removed under reduced pressure. The crude product was purified by Preparative HPLC. Mass ($ES^+$ 459)

Example 49

3-[5-(2,6-Dioxo-1,3-dipropyl-2,3,6,7-tetrahydro-1H-purin-8-yl)-bicyclo[3.3.1]non-1-yl]-acrylic acid 5-(2,6-Dioxo-1,3-dipropyl-2,3,6,7-tetrahydro-1H-purin-8-yl)-bicyclo[3.3.1]nonane-1-carbaldehyde (355 mg) was taken in THF (25 ml). Triphenyl-☐☐-phosphanylidene)-acetic acid methyl ester (614 mg) was added and refluxed overnight. Next day another 460 mg of Triphenyl-☐☐-phosphanylidene)-acetic acid methyl ester was added and refluxed for 24 hrs. Cooled to RT LiOH (210 mg), water (2 ml), MeOH (5 ml) were added and stirred at rt overnight. Solvent was removed under reduced pressure. Diluted with water (25 ml), extracted with ethyl acetate (3×25 ml). Aqueous layer was acidified with 1 N HCl and extracted with ethyl acetate (3×50 ml), dried over $Na_2SO_4$ and concentrated. Yield 254 mg. Mass ($ES^+$ 429).

Example 50

3-[5-(2,6-Dioxo-1,3-dipropyl-2,3,6,7-tetrahydro-1H-purin-8-yl)-bicyclo[3.3.1]non-1-yl]-propionic acid 3-[5-(2,6-Dioxo-1,3-dipropyl-2,3,6,7-tetrahydro-1H-purin-8-yl)-bicyclo[3.3.1]non-1-yl]-acrylic acid (150 mg) was hydrogenated in the presence of 10% Pd/C in THF:MeOH (2:1, 5 ml) @ 60 psi overnight. Catalyst was filtered through celite and the solvent was concentrated. Solid was purified by crystallizing from ether Yield 105 mg. Mass (ES$^+$ 431)

Example 51

5-(2,6-Dioxo-1,3-dipropyl-2,3,6,7-tetrahydro-1H-purin-8-yl)-9-oxa-bicyclo[3.3.1]nonane-2-carboxylic acid Step 1

1,3-Dipropyl-7-pyrrolidin-1-ylmethyl-3,7-dihydro-purine-2,6-dione (638 mg) was taken in dry THF (10 ml) at −78° C. nBuLi (0.88 ml, 2.5M in hexane) was added slowly. The reaction mixture turned orange and stirred for 30 min at −78° C. Cyclooct-4-enone (298 mg) was dissolved in 3 ml of dry THF, added to the reaction mixture. Stirred at −78° C. for 30 min, slowly warmed to rt and stirred for 2 hrs. The reaction mixture was quenched with sat NH$_4$Cl and extracted with ethyl acetate (3×50 ml). Combined organic layer was washed with 1N HCl, water, and brine. Dried over anhydrous Na$_2$SO$_4$ and concentrated. The crude product was purified in silica column, eluted with ethyl acetate:hexane (1:1). Mass (ES$^+$ 361)

Step 2

8-(1-Hydroxy-cyclooct-4-enyl)-1,3-dipropyl-3,7-dihydro-purine-2,6-dione (180 mg, from step 1) was taken in dry MeOH (15 ml) at rt. Carbon monoxide was bubbled through the solution. PdCl$_2$ (9mg) followed by CuCl$_2$ (201 mg) were added. CO was bubbled for 4 hrs at rt. The reaction mixture turned clear after 3 hrs. After 4 hr MeOH was removed under reduced pressure. Diluted with water, extracted with ethyl acetate. Ethyl acetate layer was washed with water, brine and dried over Na$_2$SO$_4$. After concentration, the crude product was purified by silica gel chromatography eluting with ethyl acetate:hexane (1:1). Yield 120 mg. Mass (ES$^+$ 419).

Step 3

5-(2,6-Dioxo-1,3-dipropyl-2,3,6,7-tetrahydro-1H-purin-8-yl)-9-oxa-bicyclo[3.3.1]nonane-2-carboxylic acid methyl ester (50 mg, from step 2) was taken in MeOH (5 ml). LiOH (15 mg) was added and stirred at rt overnight. Next day MeOH was removed under reduced pressure, diluted with water and extracted with ethyl acetate. Aqueous layer was acidified with 1N HCl, extracted with ethyl acetate (3×25 ml). Combined organic layer was washed with brine, and dried over Na$_2$SO$_4$. Concentration of the solvent gave a white solid, which was purified by crystallizing from ether. Mass (ES$^+$ 405)

Example 52

8-(5-Hydroxy-9-oxa-bicyclo[3.3.1]non-1-yl)-1,3-dipropyl-3,7-dihydro-purine-2,6-dione 1,3-Dipropyl-7-pyrrolidin-1-ylmethyl-3,7-dihydro-purine-2,6-dione (638 mg) was taken in dry THF (10 ml) at −78° C. nBuLi (0.88 ml, 2.5M in hexane) was added slowly. The reaction mixture turned orange and stirred for 30 min at −78° C. Cyclooctane-1,5-dione (280 mg,) was dissolved in 3 ml of dry THF, added to the reaction mixture. Stirred at −78° C. for 30 min, slowly warmed to rt and stirred overnight. The reaction mixture was quenched with sat NH$_4$Cl and extracted with ethyl acetate (3×50 ml). Combined organic layer was washed with 1N HCl, water, and brine. Dried over anhydrous Na$_2$SO$_4$ and concentrated. The crude product was purified on silica column, eluted with ethyl acetate:hexane (1:1). Mass (ES$^+$ 377)

Example 53

5-(2,6-Dioxo-1,3-dipropyl-2,3,6,7-tetrahydro-1H-purin-8-yl)-8-oxa-bicyclo[3.2.1 ]octane-2-carboxylic acid Step 1

Followed the same procedure from the example Example 51 step 1. Cyclohept-4-enone was used instead of Cyclooct-4-enone. Mass (ES$^+$ 347)

Step 2

8-(1-Hydroxy-cyclohept-4-enyl)-1,3-dipropyl-3,7-dihydro-purine-2,6-dione (50 mg) was taken in 10 ml of MeOH at rt. Carbon monoxide was bubbled through the MeOH for 10 min. PdCl$_2$ (25 mg), CuCl$_2$ (58 mg) were added and CO was bubbled for 3 hrs. Stirred at rt overnight. Diluted with MeOH, water and precipitate formed was filtered through celite. MeOH was removed by rotavap, the residue was extracted with ethyl acetate. Ethyl acetate layer was washed with water, brine, and dried over Na$_2$SO$_4$. After concentration, the crude product was taken in MeOH (5 ml), water (1 ml). LiOH (25 mg) was added and stirred at rt overnight. Next day the MeOH was removed by rotavap, the residue was taken up in water (20 ml) and extracted with ethyl acetate (2×25 ml). Aqueous layer was acidified with 1N HCl, extracted with ethyl acetate (2×50). Ethyl acetate layer was washed with brine and dried. After concentration the product was dissolved in ether and filtered through a pad of silica gel. Concentration gave 30 mg of the product. Mass (ES$^+$ 391)

Example 54

Phosphoric acid mono-[4-(2,6-dioxo-1,3-dipropyl-2,3,6,7-tetrahydro-1H-purin-8-yl)-bicyclo[2.2.2]oct-1-yl]ester 8-(4-Hydroxy-bicyclo[2.2.2]oct-1-yl)-1,3-dipropyl-3,7-dihydro-purine-2,6-dione (Example 13a) (180 mg, 0.5 mmol) was dissolved in a mixture of 1H-tetrazole (350 mg, 5 mmol) in 10 ml of dry acetonitrile and 10 ml of dry methylene chloride. At room temperature dibenzyl diethylphosphoramidite (476 mg, 1.5 mmol) was added under nitrogen and the mixture was stirred for 2 h. Then 70% tert-butyl hydroperoxide solution (1 ml) was added and the mixture was stirred for 1 h. At 0° C. 15 ml of 10% NaHSO$_3$ was added and the mixture was stirred for another 15 minutes. The mixture was then extracted three times with CH$_2$Cl$_2$, and the organic layer was washed water. Evaporation of solvent yielded Phosphoric acid dibenzyl ester 4-(2,6-dioxo-1,3-dipropyl-2,3,6,7-tetrahydro-1H-purin-8-yl)-bicyclo[2.2.2]oct-1-yl ester as a yellow oil, which was purified by column chromatography. Fractions contained Phosphoric acid dibenzyl ester 4-(2,6-dioxo-1,3-dipropyl-2,3,6,7-tetrahydro-1H-purin-8-yl)-bicyclo[2.2.2]oct-1-yl ester was combined and concentrated in vacuum to get 280 mg product. MS (M+1) 621.

Phosphoric acid dibenzyl ester 4-(2,6-dioxo-1,3-dipropyl-2,3,6,7-tetrahydro-1H-purin-8-yl)-bicyclo[2.2.2]oct-1-yl ester was dissolved in a mixture of 15 ml methanol and 10 ml of THF, Pd/C (10%, 50 mg) was added to the mixture.

Hydrogenation was taken place at 50 psi for 8 h. Pd/C was filtered off and solvent was evaporated off. The residue was recrystallized in a mixture of methanol and ethyl acetate to get 190 mg title product (yield 86%). MS (M+1, 441)

Example 55

4-Chloro-2-[(furan-2H-ylmethyl)-amino]-5-sulfamoyl-benzoic acid 3-[4-(2,6-dioxo-1,3-dipropyl-2,3,6,7-tetrahydro-1H-purin-8-yl)-bicyclo[2.2.2]oct-1-yl]-propionyloxymethyl ester A mixture of 3-[4-(2,6-Dioxo-1,3-dipropyl-2,3,6,7-tetrahydro-1H-purin-8-yl)-bicyclo[2.2.2]oct-1-yl]-propionic acid (208 mg, 0.5 mmol), sodium bicarbonate (168 mg, 2 mmol), and tetra-n-butylammonium hydrogensulfate (17 mg, 0.05 mmol) in water (5 ml) and dichloromethane (5 ml) was stirred vigorously at 0° C. After 10 min, to the reaction mixture was added a solution of chloromethyl chlorosulfate in dichloromethane (1 ml) and allowed to ambient temperature and continued to stir vigorously. After a couple of hours, the organic layer was separated and washed with brine. The organic extracts were dried over sodium sulfate. After the solvent was removed in vacuo, the residue was purified by column chromatography on $SiO_2$ using ethyl/hexane (1:5) as an eluent to give (200 mg, yield 86%) 3-[4-(2,6-Dioxo-1,3-dipropyl-2,3,6,7-tetrahydro-1H-purin-8-yl)-bicyclo[2.2.2]oct-1-yl]-propionic acid chloromethyl ester. MS (M+1 465)

To a solution of 4-Chloro-2-[(furan-2-ylmethyl)-amino]-5-sulfamoyl-benzoic acid (142.5 mg, 0.43 mmol) in DMF (3 ml) was added triethyl amine (10 mg, 0.95 mmol), and the mixture was stirred for 1 h. The above obtained chloromethyl ester (200 mg, 0.43 mmol) and NaI (130 mg, 0.86 mmol) were added to the reaction mixture. The reaction was let go at room temperature overnight. The reaction mixture was concentrated down under vacuo. The residue was participated between Ethyl acetate/water. The organic layer was concentrated and was purified under column chromatography to obtain the title compound (190 mg, yield 58%) as white solid. MS(M+1 759)

Example 56

1-Carboxy-3-{3-[4-(2,6-dioxo-1,3-dipropyl-2,3,6,7-tetrahydro-1H-purin-8-yl)-bicyclo[2.2.2]oct-1-yl]-propionyloxymethoxycarbonyl}-propyl-ammonium; trifluoro-acetate Followed the procedure for making Example 54, 2-tert-Butoxycarbonylamino-pentanedoic acid 1-tert-butyl ester 5-{3-[4-(2,6-dioxo-1,3-dipropyl-2,3,6,7-tetrahydro-1H-purin-8-yl)-bicyclo[2.2.2]oct-1-yl]-propionyloxymethyl} ester was made by using 2-tert-Bitoxycarbonylamino-pentanedioic acid 1-tert-butyl ester, 3-[4-(2,6-Dioxo-1,3-dipropyl-2,3,6,7-tetrahydro-1H-purin-8-yl)-bicyclo[2.2.2]oct-1-yl]-propionic acid chloromethyl ester, triethylamine, and NaI in DMF.

Deprotecting in $CH_2Cl_2$/TFA (50/50) at room temperature for 8 h, purified in prep. HPLC to get the title compound as TFA salt. (yield 20%). MS (M+1 576)

Example 57

1-Carboxy-3-(N'-{3-[4-(2,6-dioxo-1,3-dipropyl-2,3,6,7-tetrahydro-1H-purin-8-yl)-bicyclo[2.2.2]oct-1-yl]-propionyl}-hydrezinocarbonyl)-propyl-ammonium; trifluoro-acetate A mixture of 3-[4-(2,6-Dioxo-1,3-dipropyl-2,3,6,7-tetrahydro-1H-purin-8-yl)-bicyclo[2.2.2]oct-1-yl]-propionic acid (208 mg, 0.5 mmol) (Example 18) (208 mg, 0.5 mmol) in THF (15 ml), was added N-methylmorpholine (56 mg, 0.55 mmol) and isobultylchloroformate (75 mg, 0.55 mmol), and the mixture was stirred for 1 h. Hydrazinecarboxylic acid tert-butyl ester (100 mg, 0.75 mmol) was added to the reaction mixture. The reaction was let go for 2 h. The reaction mixture was washed with NaHCO3, $NaHSO_4$, and brine respectively. THF was got rid of under vacuo, and the residue was purified by column chromatography, followed by deprotection on ($CH_2Cl_2$/TFA) to get 3-[4-(2,6-Dioxo-1,3-dipropyl-2,3,6,7-tetrahydro-1H-purin-8-yl)-bicyclo[2.2.2]oct-1-yl]-propionic acid hydrazide as TFA salt. MS(M+1, 431).

The above obtained TFA salt was basified by triethylamine using the same mixed anhydride procedural as above reacting with 2-tert-Butoxycarbonylamino-pentanedioic acid 1-tert-butyl ester, followed by column chromatography, deprotection in $CH_2Cl_2$/TFA, prep. HPLC to get the title compound as TFA salt. MS(M+1 559)

Example 58

[3-(2,6-Dioxo-1,3-dipropyl-2,3,6,7-tetrahydro-1H-purin-8-ylmethyl)-adamantan-1-yl]-acetic acid Followed the same procedure from Example 45 using (3-Methoxycarbonylmethyl-adamantan-1-yl)-acetic acid instead of Bicyclo[3.3.1]nonane-1,5-dicarboxylic acid monomethyl ester. Mass ($ES^+$ 443)

Example 59

4-(2,6-Dioxo-1,3-dipropyl-2,3,6,7-tetrahydro-1H-purin-8-yl)-cubane-1-carboxylic acid.

To a solution of 4-(6-amino-2,4-dioxo-1,3-dipropyl-1,2,3,4-tetrahydro-pyrimidin-5-ylcarbamoyl)-cubane-1-carboxylic acid methyl ester (400 mg, 0.966 mmol) in MeOH (20 ml) was added 4 ml of a 20% aq. NaOH solution and the resulting turbid mixture was heated at reflux overnight (12 h). The cool reaction mixture was concentrated in vacuo, diluted with several small ice chips and acidified by the dropwise addition of concentrated HCl. The resulting white precipitate was collected, dried, and washed with ether to give a white solid (280 mg, 76%). $^1$H NMR (400 MHz, DMSO-$d_6$) δ 1.05 (coincident t, 6H), 1.70 (m, 2H), 1.83 (m, 2H), 3.99 (m, 2H), 4.08 (m, 2H), 4.27 (m, 3H), 4.38 (m, 3H). MS: 383 ($MH^+$).

Example 60

8-(1-Hydroxymethyl-cuban-4-yl)-1,3-dipropyl-3,7-dihydro-purine-2,6-dione.

To a stirred suspension of 4-(2,6-dioxo-1,3-dipropyl-2,3,6,7-tetrahydro-1H-purin-8-yl)-cubane-1-carboxylic acid (100 mg, 0.261 mmol) and HATU (1.1 eq, 0.288 mmol, 110 mg) in 6 ml of MeCN was added Hunig's base (1.1 eq, 0.288 mmol, 37 mg), neat via syringe. The resulting heterogeneous mixture was stirred for 3 h and $NaBH_4$ (2.0 eq, 0.522 mmol, 20 mg) was added in one portion. The mixture was stirred for an additional 2 h, cooled with the aid of an ice bath and acidified by the dropwise addition of concentrated HCl. The resulting pale yellow precipitate was collected, dried, and resuspended in MeCN. After stirring overnight the material was collected and dried to afford an off-white powder (50 mg, 52%). MS: 369 ($MH^+$).

Example 61

4-(7-Benzyl-2,6-dioxo-1,3-dipropyl-2,3,6,7-tetrahydro-1H-purin-8-yl)-bicyclo[2.2.2]octane-1-carboxylic acid.

To a stirred solution of 4-[(6-amino-2,4-dioxo-1,3-dipropyl-1,2,3,4-tetrahydro-pyrimidin-5-yl)-benzylcarbamoyl]-bicyclo[2.2.2]octane-1-carboxylic acid methyl ester (430 mg, 0.843 mmol) in i-PrOH (20 ml) was added 2 N KOH (4.0 eq, 3.37 mmol, 1.7 ml) and the resulting mixture was heated at reflux for 26 h. The cool reaction mixture was concentrated in vacuo to give a semi-solid residue that was diluted with water and extracted with $CHCl_3$. The aqueous phase was acidified with concentrated HCl to afford a white precipitate that was collected and dried (381 mg, 91%). MS: 479 (MH$^+$).

Example 62

4-(2,6-Dioxo-1,3-dipropyl-2,3,6,7-tetrahydro-1H-purin-8-yl)-bicyclo[2.2.2]octane-1-carbaldehyde oxime To a stirred solution of 4-(2,6-dioxo-1,3-dipropyl-2,3,6,7-tetrahydro-1H-purin-8-yl)-bicyclo[2.2.2]octane-1-carbaldehyde (1.6 g, 4.3 mmol) in MeOH (30 ml) was added hydroxylamine hydrochloride (1.2 eq, 5.16 mmol, 356 mg) and a solution of NaOAc (trihydrate, 1.5 eq, 6.45 mmol, 890 mg) in water (10 ml). The resulting mixture was stirred at rt overnight. The mixture was concentrated in vacuo and the solid residue was suspended in water (15 ml), collected, washed with water and dried to afford a white powder (1.4 g, 84%).

This method was also used in the preparation of:

Example 62a: [4-(2,6-Dioxo-1,3-dipropyl-2,3,6,9-tetrahydro-1H-purin-8-yl)-bicyclo[2.2.2]oct-1-yl]-acetaldehyde oxime. MS: 404 (MH$^+$).

Example 63

3-[4-(2,6-Dioxo-1,3-dipropyl-2,3,6,7-tetrahydro-1H-purin-8-yl)-bicyclo[2.2.2]oct-1-yl]-acrylonitrile.

To a stirred suspension of 4-(2,6-dioxo-1,3-dipropyl-2,3,6,7-tetrahydro-1H-purin-8-yl)-bicyclo[2.2.2]octane-1-carbaldehyde (535 mg, 1.44 mmol) and (cyanomethyl)triphenylphosphonium chloride (1.2 eq, 1.73 mmol, 582 mg) in THF (30 ml) at 0° C. was added KHMDS (0.5 $\underline{M}$ in toluene, 2.2 eq, 3.16 mmol, 6.3 ml). The resulting mixture was stirred for 1.5 h at this temperature then heated at 55° C. for 5 h. The cool reaction mixture was partitioned between EtOAc (10 ml) and a saturated aqueous NH$_4$Cl solution (20 ml) and the aqueous phase was extracted with EtOAc (20 ml). The combined organic phases were washed with a saturated aqueous NaCl solution (2×20 ml), dried (MgSO$_4$), filtered and evaporated to give a solid residue that was purified by radial chromatography (2 mm plate) using 5% MeOH in CH$_2$Cl$_2$ as eluent to afford 425 mg (75%) of a brittle foam (mixture of cis/trans isomers). MS: 396 (MH$^+$).

This method was employed in the synthesis of:

Example 63a: {2-[4-(2,6-Dioxo-1,3-dipropyl-2,3,6,7-tetrahydro-1H-purin-8-yl)-bicyclo[2.2.2]oct-1-yl]-vinyl}-phosphonic acid diethyl ester. MS: 507 (MH$^+$).

Example 64

3-[4-(2,6-Dioxo-1,3-dipropyl-2,3,6,7-tetrahydro-1H-purin-8-yl)-bicyclo[2.2.2]oct-1-yl]-propionitrile.

A solution of 3-[4-(2,6-dioxo-1,3-dipropyl-2,3,6,7-tetrahydro-1H-purin-8-yl)-bicyclo[2.2.2]oct-1-yl]-acrylonitrile (110 mg, 0.278 mmol) in MeOH (20 ml) and CH$_2$Cl$_2$ (5 ml) was hydrogenated using Pd on carbon (10 mol %) and a ballon of hydrogen affixed to a 3-way stopcock/ground glass adapter. After stirring overnight, the mixture was degassed, filtered through Celite and concentrated in vacuo to give a brittle foam (100 mg, 90%). $^1$H NMR (400 MHz, CDCl$_3$); δ 0.93 (coincident triplets, 6H), 1.53 (m, 6H),1.57 (t, 2H), 1.67 (m, 2H), 1.77 (m, 2H), 2.00 (m, 6H), 2.24 (t, 2H), 3.99 (t, 2H), 4.05 (t, 2H), 12.17 (s, 1H).

The following compounds were prepared in an analogous manner:

Example 64a: 4-[4-(2,6-dioxo-1,3-dipropyl-2,3,6,7-tetrahydro-1H-purin-8-yl)-bicyclo-[2.2.2]oct-1-yl]-butyric acid methyl ester, MS: 445 (MH$^+$);

Example 64b: {2-[4-(2,6-Dioxo-1,3-dipropyl-2,3,6,7-tetrahydro-1H-purin-8-yl)-bicyclo-[2.2.2]oct-1-yl]-ethyl}-phosphonic acid diethyl ester, MS: 509 (MH$^+$).

Example 65

4-(2,6-Dioxo-1,3-dipropyl-2,3,6,9-tetrahydro-1H-purin-8-yl)-bicyclo[2.2.2]octane-1-carbonitrile To a stirred suspension of 4-(2,6-dioxo-1,3-dipropyl-2,3,6,9-tetrahydro-1H-purin-8-yl)-bicyclo[2.2.2]octane-1-carbaldehyde oxime (400 mg, 1.03 mmol) in CHCl$_3$ (20 ml), cooled with the aid of an ice bath, was added POCl$_3$ (neat, 1.5 eq, 237 mg) and the resulting mixture was allowed to reach ambient temperature overnight (17 h). The reaction mixture was poured into water, the phases were separated and the organic phase was washed with saturated aqueous solution of NaHCO$_3$, dried over Na$_2$SO$_4$, filtered and concentrated in vacuo to give a white, brittle foam (360 mg, 95%). MS: 370 (MH$^+$).

Example 66

[4-(2,6-Dioxo-1,3-dipropyl-2,3,6,9-tetrahydro-1H-purin-8-yl)-bicyclo[2.2.2]oct-1-yl]-acetaldehyde To a stirred suspension of methoxymethyl triphenylphosphonium chloride (1.1 g, 3.2 mmol) in THF (60 ml) at −78° C. was added a solution of KHMDS (0.5 M in toluene, 10 ml, 5 mmol). The resulting yellow mixture was stirred at this temperature for 1.5 h and a solution of 4-(2,6-dioxo-1,3-dipropyl-2,3,6,9-tetrahydro-1H-purin-8-yl)-bicyclo[2.2.2]octane-1-carbaldehyde (372 mg, 1.0 mmol) in THF (12 ml) was added over a period of 20 minutes. The mixture was held at −78° C. for 6 h and allowed to reach ambient temperature overnight (12 h). The reaction mixture was partitioned between saturated aqeuous NH$_4$Cl (100 ml) and EtOAc (100 ml) and the aqueous phase was extracted with EtOAc (50 ml). The combined organic extracts were washed with saturated aqeuous NaCl (100 ml), concentrated in vacuo, redissolved in THF and concentrated to a volume of approx. 20 ml. To the solution was added an equal volume of 1 N HCl and the mixture was stirred overnight. The mixture was diluted with EtOAc (20 ml), the aqueous phase was separated and extracted with EtOAc (10 ml). The combined organic phases were then washed with saturated aqeuous NaCl (2×, 25 ml), dried (MgSO$_4$), filtered and concentrated in vacuo. The resulting orange oil was purified in batches by radial chromatography (2 mm plate) using 3% MeOH and 3% THF in CH$_2$Cl$_2$ as eluent. Product-containing fractions were combined and concentrated to afford 290 mg (75%) of a white solid. MS: 387 (MH$^+$).

Example 67

[4-(2,6-Dioxo-1,3-dipropyl-2,3,6,9-tetrahydro-1H-purin-8-yl)-bicyclo[2.2.2]oct-1-yl]-acetic acid To a solution of [4-(2,6-dioxo-1,3-dipropyl-2,3,6,9-tetrahydro-1H-purin-8-yl)-bicyclo[2.2.2]oct-1-yl]- acetaldehyde (170 mg, 0.440 mmol) in t-BuOH (10 ml) and 2-methyl-2-butene (10 eq, 4.4 mmol, 470 μL), cooled with the aid of an ice bath, was added NaClO$_2$ (1.5 eq, 0.66 mmol). The resulting yellow solution was allowed to reach ambient temperature over a period of 14 h then concentrated in vacuo. The resulting oily residue was partitioned between water (10 ml) and CH$_2$Cl$_2$ (10 ml). The aqueous phase was acidified by the dropwise addition of concentrated HCl and the resulting precipitate was collected, washed with water and dried to afford 105 mg (59%) as a white powder. $^1$H NMR (400 MHz, CDCl$_3$); d 0.91 (t, 3H), 0.93 (t, 3H), 1.63 (m, 2H), 1.77 (m, 2H, partially-obscured), 1.82 (m, 6H), 2.01 (m, 6H), 2.32 (s, 2H), 3.95 (m, 2H), 4.07 (m, 2H), 12.74 (s, 1H).

Example 68

{2-[4-(2,6-Dioxo-1,3-dipropyl-2,3,6,7-tetrahydro-1H-purin-8-yl)-bicyclo[2.2.2]oct-1-yl]-ethyl}-phosphonic acid monoethyl ester Dissolved {2-[4-(2,6-dioxo-1,3-dipropyl-2,3,6,7-tetrahydro-1H-purin-8-yl)-bicyclo-[2.2.2]oct-1-yl]-ethyl}-phosphonic acid diethyl ester (30 mg, 59 μmol) in 1 N NaOH (4 ml) and heated the solution at 80° C. for 3 h. The mixture was allowed to cool to rt and slowly acidified with concentrated HCl. The resulting precipitate was collected and dried (22 mg, 79%). $^1$H NMR (400 MHz, CDCl$_3$); δ 0.93 (coincident triplets, 6H), 1.31 (t, 3H), 1.48 (m, 8H), 1.70 (br m, 6H), 1.95 (m, 6H), 3.95 (t, 2H), 4.07 (t, 2H), 12.2 (br s, 1H).

Example 69

8-[4-(3-Hydroxy-propyl)-bicyclo[2.2.2]oct-1-yl]-1,3-dipropyl-3,7-dihydro-purine-2,6-dione To a solution of 3-[4-(2,6-dioxo-1,3-dipropyl-2,3,6,7-tetrahydro-1H-purin-8-yl)-bicyclo-[2.2.2]oct-1-yl]-propionic acid (417 mg, 1.0 mmol) in THF (25 ml), cooled to 0° C. with the aid of an ice bath, was added BH$_3$ (1.0 M in THF, 3.0 mmol). The resulting mixture was allowed to reach ambient temperature and stirred for a period of 60 h. Following the addition of MeOH (10 ml), the mixture was concentrated in vacuo to afford a white solid that was dissolved in MeOH (20 ml), stirred at rt for 2 h and evaporated to dryness in vacuo. The resulting white solid was recrystallized from EtOAc to afford 345 mg (86%) of a white powder. MS: 403 (MH$^+$).

This method was also used to prepare:

Example 69a: 8-[4-(2-Hydroxy-ethyl)-bicyclo[2.2.2]oct-1-yl]-1,3-dipropyl-3,9-dihydro-purine-2,6-dione. MS: 389 (MH$^+$).

Example 70

3-[4-(2,6-Dioxo-1,3-dipropyl-2,3,6,7-tetrahydro-1H-purin-8-yl)-bicyclo[2.2.2]oct-1-yl]-propionamide To a solution of 3-[4-(2,6-dioxo-1,3-dipropyl-2,3,6,7-tetrahydro-1H-purin-8-yl)-bicyclo-[2.2.2]oct-1-yl]-propionic acid (510 mg, 1.22 mmol) and HATU (1.1 eq, 1.34 mmol, 511 mg) in DMF (10 ml) was added Hunig's base (1.3 eq, 1.60 mmol, 205 mg). After the resulting suspension had been stirred for 1 h, excess ammonia (0.5 M in dioxane, 4.0 ml) was added and the mixture was stirred overnight (14 h). The solvent was removed in vacuo and the resulting residue was partitioned between CH$_2$Cl$_2$ (10 ml) and 1 N HCl (10 ml) with the aid of 2 ml MeOH to assist in the transfer and improve solubility. The aqueous phase was extracted with CH$_2$Cl$_2$ (2×10 ml), the combined organic phases were washed with 1 N HCl (2×10 ml), dried (MgSO$_4$), filtered and evaporated in vacuo to give an off-white solid (455 mg, 90%). MS: 416 (MH$^+$).

This method was employed in the synthesis of the following compounds:

Example 70a: 3-[4-(2,6-Dioxo-1,3-dipropyl-2,3,6,7-tetrahydro-1H-purin-8-yl)-bicyclo-[2.2.2]oct-1-yl]-N-(1H-tetrazol-5-yl)-propionamide, MS: 484 (MH$^+$);

Example 70b: N-(2-Cyano-ethyl)-3-[4-(2,6-dioxo-1,3-dipropyl-2,3,6,7-tetrahydro-1H-purin-8-yl)-bicyclo[2.2.2]oct-1-yl]-propionamide, MS: 469 (MH$^+$);

Example 70c: 2-[4-(2,6-Dioxo-1,3-dipropyl-2,3,6,7-tetrahydro-1H-purin-8-yl)-bicyclo-[2.2.2]octane-1-carbonyl]-amino}-3-hydroxy-butyric acid methyl ester, MS: 504 (MH$^+$);

Example 70d: 2-{[4-(2,6-Dioxo-1,3-dipropyl-2,3,6,7-tetrahydro-1H-purin-8-yl)-bicyclo-[2.2.2]octane-1-carbonyl]-amino}-3-hydroxy-propionic acid methyl ester, MS: 480 (MH$^+$).

Example 71

{2-[4-(2,6-Dioxo-1,3-dipropyl-2,3,6,7-tetrahydro-1H-purin-8-yl)-bicyclo[2.2.2]oct-1-yl]-ethyl}-phosphonic acid To a solution of {2-[4-(2,6-dioxo-1,3-dipropyl-2,3,6,7-tetrahydro-1H-purin-8-yl)-bicyclo[2.2.2]oct-1-yl]-ethyl}-phosphonic acid diethyl ester (30 mg, 59 μmol) in CH$_2$Cl$_2$ (8 ml) was added TMSBr (excess) and the resulting mixture was stirred at rt overnight. Additional TMSBr was added and the reaction was heated at 55° C. for 6 h. The solvent was removed in vacuo to give an orange solid whose color was discharged upon trituration with water. The material was collected, washed with water and dried (20 mg, 77%). MS: 453 (MH$^+$).

Example 72

3-(5-{2-[4-(2,6-Dioxo-1,3-dipropyl-2,3,6,7-tetrahydro-1H-purin-8-yl)-bicyclo[2.2.2]oct-1-yl]-ethyl}-tetrazol-1-yl)-propionitrile A solution of N-(2-cyano-ethyl)-3-[4-(2,6-dioxo-1,3-dipropyl-2,3,6,7-tetrahydro-1H-purin-8-yl)-bicyclo[2.2.2] oct-1-yl]-propionamide (500 mg, 1.06 mmol, 1.0 eq), Ph$_3$P (2.0 eq, 2.13 mmol, 560 mg), TMSN$_3$ (2.0 eq, 2.13 mmol, 245 mg), and DEAD (2.0 eq, 2.13 mmol, 371 mg) in THF (10 ml) was stirred at rt for 24 h. The reaction vessel was re-charged with the reagent cocktail (2.0 eq, 2.13 mmol) and stirring was continued for an additional 24 h. The reaction was quenched by the addition of a 5% aqueous solution of (NH$_4$)$_2$Ce(NO$_3$)$_6$ and extracted with EtOAc. The combined organic extracts were washed with brine, dried over MgSO$_4$, filtered and evaporated in vacuo to afford a viscous orange oil. A portion of the material was purified by preparative LC to afford 20 mg of pure material. MS: 494 (MH$^+$).

Example 73

1,3-Dipropyl-8-{4-[2-(1H-tetrazol-5-yl)-ethyl]-bicyclo[2.2.2]oct-1-yl}-3,7-dihydro-purine-2,6-dione To a solution of 3-(5-{2-[4-(2,6-Dioxo-1,3-dipropyl-2,3,6,7-tetrahydro-1H-purin-8-yl)-bicyclo[2.2.2]oct-1-yl]- ethyl}-tetrazol-1-yl)-propionitrile (150 mg, 0.30 mmol) in THF (20 ml) was added 3 ml of 1N NaOH. The resulting mixture was stirred at rt for 8 h, concentrated in vacuo and extracted with $CH_2Cl_2$ (2×10 ml). The aqueous phase was acidified by the careful addition of concentrated HCl and the resulting precipitate was collected, washed with water and dried to afford 55 mg (41%) of a white powder. MS: 441 ($MH^+$).

This method was also employed in the synthesis of:

Example 73a: 1,3-Dipropyl-8-[4-(1H-tetrazol-5-yl)-bicyclo [2.2.2]oct-1-yl]-3,7-dihydro-purine-2,6-dione. MS: 413 ($MH^+$).

Example 74

4-[4-(2,6-Dioxo-1,3-dipropyl-2,3,6,7-tetrahydro-1H-purin-8-yl)-bicyclo[2.2.2]oct-1-yl]-butyric acid A solution of 4-[4-(2,6-dioxo-1,3-dipropyl-2,3,6,7-tetrahydro-1H-purin-8-yl)-bicyclo[2.2.2]oct-1-yl]-butyric acid methyl ester (45 mg, 100 μmol) in THF (4 ml) was treated with 1 M LiOH (2 ml) and the resulting turbid solution was stirred at rt overnight. The solution was concentrated in vacuo diluted with water (2 ml) and acidified by the dropwise addition of concentrated HCl. The resulting precipitate was collected, washed with water and dried to afford a white powder (35 mg, 81%). MS: 431 ($MH^+$).

This method was employed in the synthesis of the following compounds:

Example 74a: 3-[4-(2,6-Dioxo-1,3-dipropyl-2,3,6,7-tetrahydro-1H-purin-8-yl)-cuban-1-yl]-acrylic acid, MS: 409 ($MH^+$);

Example 74b: 3-[4-(2,6-Dioxo-1,3-dipropyl-2,3,6,9-tetrahydro-1H-purin-8-yl)-bicyclo-[2.2.2]oct-1-yl]-4,5-dihydro-isoxazole-5-carboxylic acid, MS: 458 ($MH^+$);

Example 74c: 3-[4-(2,6-Dioxo-1,3-dipropyl-2,3,6,9-tetrahydro-1H-purin-8-yl)-bicyclo-[2.2.2]oct-1-yl]-isoxazole-5-carboxylic acid, MS: 456 ($MH^+$);

Example 74d: 2-[4-(2,6-Dioxo-1,3-dipropyl-2,3,6,9-tetrahydro-1H-purin-8-yl)-bicyclo-[2.2.2]oct-1-yl]-thiazole-4-carboxylic acid, ms: 472 ($MH^+$);

Example 74e: 2-{2-[4-(2,6-Dioxo-1,3-dipropyl-2,3,6,9-tetrahydro-1H-purin-8-yl)-bi-cyclo[2.2.2]oct-1-yl]-ethyl}-thiazole-4-carboxylic acid, MS: 500 ($MH^+$);

Example 74f: 4-[4-(2,6-Dioxo-1,3-dipropyl-2,3,6,9-tetrahydro-1H-purin-8-yl)-bicyclo-[2.2.2]oct-1-yl]-but-2-enoic acid, MS: 429 ($MH^+$);

Example 74g: 3-[4-(2,6-Dioxo-1,3-dipropyl-2,3,6,9-tetrahydro-1H-purin-8-yl)-bicyclo-[2.2.2]oct-1-ylmethyl]-isoxazole-5-carboxylic acid, MS: 470 ($MH^+$);

Example 75

8-[4-(5-Hydroxymethyl-isoxazol-3-yl)-bicyclo [2.2.2]oct-1-yl]-1,3-dipropyl-3,9-dihydro-purine-2,6-dione A solution of 4-(2,6-dioxo-1,3-dipropyl-2,3,6,9-tetrahydro-1H-purin-8-yl)-bicyclo-[2.2.2]octane-1-carbaldehyde oxime (87 mg, 0.22 mmol) and N-chloro succinimide (1.2 eq, 0.27 mmol, 36 mg) in DMF (6 ml) was heated in an oil bath at 60° C. for 1.5 h. The reaction flask was removed from the bath and allowed to cool to rt and propargyl alcohol (2.0 eq, 0.44 mmol, 25 mg) was added. The flask was returned to the oil bath, $Et_3N$ (2.0 eq, 0.44 mmol, 44 mg) was added over a period of 15 minutes and the resulting mixture was heated at 60° C. for 3.5 h. The cool reaction mixture was evaporated in vacuo to afford a solid residue that was purified by radial chromatography (2 mm plate) using a gradient of 2–10% MeOH in $CH_2Cl_2$ as eluent. Product-containing fractions were combined and concentrated to afford 31 mg (26%) of a white solid. MS: 442 ($MH^+$).

The following compounds were prepared in an analogous manner:

Example 75a: 3-[4-(2,6-Dioxo-1,3-dipropyl-2,3,6,9-tetrahydro-1H-purin-8-yl)-bicyclo-[2.2.2]oct-1-yl]-4,5-dihydro-isoxazole-5-carboxylic acid methyl ester, MS: 472 ($MH^+$);

Example 75b: 3-[4-(2,6-Dioxo-1,3-dipropyl-2,3,6,9-tetrahydro-1H-purin-8-yl)-bicyclo-[2.2.2]oct-1-yl]-isoxazole-5-carboxylic acid methyl ester, MS: 470 ($MH^+$);

Example 75c: 8-{4-[5-(4-Methoxy-phenyl)-isoxazol-3-yl]-bicyclo[2.2.2]oct-1-yl}-1,3-dipropyl-3,9-dihydro-purine-2,6-dione, MS: 518 ($MH^+$);

Example 75d: 3-[4-(2,6-Dioxo-1,3-dipropyl-2,3,6,9-tetrahydro-1H-purin-8-yl)-bicyclo-[2.2.2]oct-1-ylmethyl]-isoxazole-5-carboxylic acid methyl ester, MS: 484 ($MH^+$).

Example 76

3-[4-(2,6-Dioxo-1,3-dipropyl-2,3,6,7-tetrahydro-1H-purin-8-yl)-bicyclo[2.2.2]oct-1-yl]-thiopropionamide.

A suspension of $P_4S_{10}$ (23 mg, 53 μmol) and $Na_2CO_3$ (4 mg, 53 μmol) in THF (4 ml) was stirred vigorously for 20 min and 3-[4-(2,6-dioxo-1,3-dipropyl-2,3,6,7-tetrahydro-1H-purin-8-yl)-bicyclo-[2.2.2]oct-1-yl]-propionamide (20 mg, 45 μmol) was added. The resulting pale yellow solution was stirred at rt for 1 h, evaporated to dryness and dried in vacuo overnight. The crude material was purified by radial chromatography (1 mm plate) using 2–5% MeOH in $CH_2Cl_2$ as eluent to afford a white solid (11 mg, 55%). MS: 432 ($MH^+$).

This method was employed in the synthesis of the following compound:

Example 76a; 4-(2,6-Dioxo-1,3-dipropyl-2,3,6,7-tetrahydro-1H-purin-8-yl)-bicyclo-[2.2.2]octane-1-carbothioic acid amide, MS: 404 ($MH^+$).

Example 77

1,3-Dipropyl-8-(4-vinyl-bicyclo[2.2.2]oct-1-yl)-3,9-dihydro-purine-2,6-dione

To a stirred suspension of methyl triphenylphosphonium chloride (1.07 g, 3.0 mmol) in THF (20 ml) at 0° C. was added n-BuLi (1.4 M in hexane, 2.14 ml, 3.0 mmol). The resulting reddish-brown mixture was stirred at this temperature for 0.5 h and then at rt for 0.5 h. A solution of 4-(2,6-dioxo-1,3-dipropyl-2,3,6,9-tetrahydro-1H-purin-8-yl)-bicyclo[2.2.2]octane-1-carbaldehyde (372 mg, 1.0 mmol) in THF (10 ml) was added over a period of 20 minutes and the resulting mixture was stirred overnight (12 h). The reaction mixture was partitioned between saturated aqeuous $NH_4Cl$ (20 ml) and EtOAc (20 ml) and the aqueous phase was extracted with EtOAc (20 ml). The combined organic extracts were washed with saturated aqeuous NaCl (50 ml), dried ($MgSO_4$), filtered and evaporated in vacuo to afford an oil that was purified by radial chromatography (2 mm plate) using a gradient of 0–5% MeOH in CH$_2$Cl$_2$ as eluent. Product-containing fractions were combined and concentrated to afford 140 mg (38%) of a white solid. MS: 371 (MH$^+$).

Example 78

2-[4-(2,6-Dioxo-1,3-dipropyl-2,3,6,7-tetrahydro-1H-purin-8-yl)-bicyclo[2.2.2]oct-1-yl]-thiazole-4-carboxylic acid ethyl ester A suspension of 4-(2,6-dioxo-1,3-dipropyl-2,3,6,7-tetrahydro-1H-purin-8-yl)-bicyclo[2.2.2]octane-1-carbothioic acid amide (20 mg, 50 μmol) and KLCO$_3$ (8.0 eq, 400 μmol) in THF (5 ml) was stirred vigorously for 5 min and ethyl bromopyruvate (29 mg, 150 μmol) was added neat via syringe. The resulting, pale yellow solution was stirred at rt for 1 h, cooled to 0° C. with the aid of an ice bath and treated sequentially with pyridine (8.0 eq, 400 μmol) and (F$_3$CCO)$_2$O (4.0 eq, 42 mg, 200 μmol). The resulting deep red solution was allowed to reach ambient temperature overnight. Following the addition of water (4 ml), the mixture was concentrated in vacuo and extracted with CH$_2$Cl$_2$ (2×10 ml). The combined organic phases were washed with 2 N HCl, dried (Na$_2$SO$_4$), filtered and concentrated in vacuo. The solution was purified by radial chromatography (1 mm plate) using 2–5% MeOH in CH$_2$Cl$_2$ as eluent to afford a white solid (22 mg, 88%). MS: 500 (MH$^+$).

Example 79 cis/trans-1-(2-Chloroethyl)-cyclohexane-1,4-dicarboxylic acid dimethyl ester (II)

A mixture of n-butyllithium (1.6 M in hexane, 0.275 mol) is added over 25 minutes to a stirred mixture of diisopropylamine (0.3 mul, 42 ml) in dry THF (200 ml) cooled to −78° C. under nitrogen. The resulting mixture is stirred at −78° C. for 30 min. To the mixture is added TMU (1.675 mol, 200 ml) over 20 min. To this mixture of LDA and TMU is added 1,4-dimethyl-cyclohexanedicarboxylate (I, 0.25 mol, 45 ml) over 10 min. After stirring an additional 40 min, bromochloroethane (0.30 mol, 25 ml) is added over 10 min. The resulting mixture is stirred at −78° C. for 30 min, the cold bath is then withdrawn and the reaction is stirred overnight with warming to 20–25° C. Hydrochloric acid (3N, 200 ml) is then added and briskly stirred for 10 min. The THF is removed under reduced pressure and the resulting aqueous residue is extracted with hexanes (3×200 ml). The combined organic extracts are washed with hydrochloric acid (3N, 2×200 ml), water (1×100 ml), saturated sodium bicarbonate (2×100 ml) and saline (1×100 ml) and dried over magnesium sulfate. Suction filtration and concentration under reduced pressure gives the title compound.

Example 80

Bicyclo[2.2.2]octane-1,4-dicarboxylic acid dimethyl ester (III)

n-Butyllithium (2.5 M in hexane, 313 mmol) is slowly added to a stirred mixture of diisopropylamine (50 ml, 357 mmol) in dry THF (450 ml) cooled to −30° C., under nitrogen. The mixture is stirred for 30 min at −30° C. and cooled to −78° C. In a separate flask, a mixture of cis/trans-1-(2-chloroethyl)-cyclohexane-1,4-dicarboxylic acid dimethyl ester (II, Example 79, 80 g, 303 mmol) in THF (1100 ml) and HMPA (225 ml, 1280 mmol) is prepared under a nitrogen atmosphere and cooled to −78° C. with stirring. The LDA solution is then added through a transfer line over 1 hour. The result mixture is stirred at −78° C. for further 1 hour and warmed to 20–25° C. during two hours and stirred for another 30 min. Then saturated aqueous ammonium chloride is added. The mixture is concentrated to about 1 l followed by dilution with 500 ml water and extraction with hexane (3×350 ml). The combined hexane extracts are washed with saline, dried over sodium sulfate, filtered and concentrated. The crude product is crystallized from hexane to give the title compound.

Example 81

Bicyclo-[2.2.2]octane-1,4-dicarboxylic acid monomethyl ester (IV)

A mixture of Bicyclo[2.2.2]octane-1,4-dicarboxylic acid dimethyl ester (III, Example 80, 20.4 g, 89.5 mmol), barium hydroxide octahydrate (14 g, 44.7 mmol) in methanol (160 ml) and water (40 ml) is stirred at 20–25° C. for 18 hour. The mixture is diluted with water (600 ml) and extracted with hexane (150 ml×2). The aqueous mixture is acidified (6 N hydrochloric acid) to pH=1–2 and extracted with chloroform (150 ml×2). The combined chloroform extracts are concentrated. The residue is dissolved in toluene, filtered and concentrated to give the title compound, mp=169–173° C.

Example 82

4-Chlorocarbonylbicyclo[2.2.2]octane-1-carboxylic acid methyl ester (V)

Bicyclo-[2.2.2]octane-1,4-dicarboxylic acid monomethyl ester (IV, Example 81, 1 wt) is dissolved in dichloromethane (6.25 vol) and dimethylformamide (0.025 vol) is added. Concomitantly oxalyl chloride (0.5125 vol) is dissolved in dichloromethane (0.625 vol) and the resulting mixture is added to the mixture containing the bicyclo-[2.2.2]octane-1,4-dicarboxylic acid monomethyl ester (IV) at between 12 to 17° C., taking care for gas evolution. The mixture is stirred at 15 to 25° for 2 to 4 hours which is monitored by (TLC; dichloromethane/methanol: 9/1, visualization Bromocresol green). The solvent is removed under reduced pressure at 40 to 45°, dichloromethane (5 vol) is added, stirred for 5 to 15 min and removed under reduced pressure at 40 to 45°. The process is repeated by adding dichloromethane (5 vol), stirring for 5 to 15 min and removing under reduced pressure at 40 to 45°. Acetonitrile (6.25 vol) is then added to give the title compound in solution.

Example 83a 4-(6-Amino-2,4-dioxo-1,3-dipropyl-1,2,3,4-tetrahydropyrimidin-5-ylcarbamoyl)bicyclo[2.2.2]octane-1-carboxylic acid methyl ester (VII)

Diaminodipropyluracil hydrochloride (VI, 1.36 wt) is suspended in acetonitrile (12.5 vol), cooled to 0 to 5° C. and triethylamine (2.46 vol) is added between 0 to 10° C. The mixture is then cooled to 0 to 5° C. A mixture of 4-chlorocarbonylbicyclo[2.2.2]-octane-1-carboxylic acid methyl ester (V, Example 82) in acetonitile is added to the diaminodipropyluracil mixture between 0 to 20° C. The reaction mixture is then warmed to 15 to 25° C. and stirred for 15 to 20 hours by which time all of the 4-chlorocarbonylbicyclo[2.2.2]octane-1-carboxylic acid methyl ester (V) is consumed (TLC; dichloromethane/methanol, 9/1; visualization Bromocresol green). The reaction mixture is diluted with water (3.12 vol) and concentrated under reduced pressure at 40 to 45° C. (18 to 20 vol of solvent is removed). The concentrate is extracted with ethyl acetate (3×6 vol) and the combined organics are washed sequentially with citric acid (10%, 3×3.12 vol), hydrochloric acid (1M, 2.5 vol), water (3.12 vol), saturated sodium bicarbonate (3.12 vol) and saline (3.12 vol). The mixture is dried over magnesium sulphate (0.75 wt) for 5 to 15 min, filtered, washed with ethyl acetate (1 vol) and the solvent removed under reduced pressure at 40 to 45° C. to give the title compound.

Example 83b 4-(6-Amino-2,4-dioxo-1,3-dipropyl-1,2,3,4-tetrahydro-pyrimidin-5-ylcarbamoyl)-bicyclo[2.2.2]octane-1-carboxylic acid methyl ester (VII, Step E)

4-Chlorocarbonylbicyclo[2.2.2]octane-1-carboxylic acid methyl ester (V, Example 82, 0.562 kg) is dissolved in dichloromethane (3.55 l) and dimethylformamide (0.014 l) is added. Concomitantly oxalyl chloride (0.291 l) is dissolved in dichloromethane (0.355 l) and the resulting mixture is added to the 4-chlorocarbonylbicyclo[2.2.2]octane-1-carboxylic acid methyl ester (V, Example 82) mixture at between 12 to 17° C. The mixture is stirred at 15 to 25° C. for 2 hours, by which time all of the 4-chlorocarbonylbicyclo[2.2.2]octane-1-carboxylic acid methyl ester (V, Example 82) is consumed (TLC; dichloromethane/methanol, 9/1; visualization with Bromocresol green). The solvent is removed under reduced pressure at 40 to 45°, dichloromethane (0.355 l) is added, stirred for 5 to 15 min and removed under reduced pressure at 40 to 45° C. The process is repeated by adding dichloromethane (2.83 l), stirring for 5 to 15 min and concentrating in vacuo at 40 to 45° C. Acetonitrile (3.54 l) is then added (mixture A). In a separate flask, diaminodipropyluracil hydrochloride (VI, 0.772 kg) is suspended in acetonitrile (7.09 l), cooled to 0 to 5° C. and triethylamine (1.40 l) is added between 0 to 10° C. (mixture B). The mixture is then cooled to 0 to 5° C. Mixture A is added to mixture B between 0 to 20° C. The reaction mixture is warmed to 15 to 25° C. and stirred for 16 hours by which time all of the acid chloride is consumed (TLC; dichloromethane/methanol, 9/1; visualization with Bromocresol green). The reaction mixture is diluted with water (1.77 l) and concentrated under reduced pressure at 40 to 45° C. The concentrate is extracted with ethyl acetate (3×3.41 l) and the combined organics are washed sequentially with citric acid (10%, 3×1.77 l), hydrochloric acid (1 M, 1.42 l), water (1.77 l), saturated sodium bicarbonate (1.77 l) and saturated saline (1.77 l). The mixture is dried over magnesium sulfate (0.426 kg) for 5 to 15 min, filtered, washed with ethyl acetate (0.568 l) and the solvent evaporated under reduced pressure at 40 to 45° C. to give the title compound.

Example 84a 4-(2,6-Dioxo-1,3-dipropyl-2,3,6,7-tetraydro-1H-purin-8-yl)-bicyclo[2.2.2]octane-1-carboxylic acid methyl ester (VIII)

4-(6-Amino-2,4-dioxo-1,3-dipropyl-1,2,3,4-tetrahydropyrimidin-5-ylcarbamoyl)bicyclo[2.2.2]octane-1-carboxylic acid methyl ester (VII, Example 83a, 1 wt) and isopropanol (4.76 vol) are mixed and stirred under nitrogen. Potassium hydroxide (2M, 4.76 vol) is added. The title compound is formed but not isolated.

Example 85a 4-(2,6-Dioxo-1,3-dipropyl-2,3,6,7-tetrahydro-1H-purin-8-yl)-bicyclo[2.2.2]octane-1-carboxylic acid (IX)

4-(2,6-Dioxo-1,3-dipropyl-2,3,6,7-tetraydro-1H-purin-8-yl)-bicyclo[2.2.2]octane-1-carboxylic acid methyl ester (VIII, Example 84a) in the potassium hydroxide environment is heated at reflux for 2 to 3 hr until complete as measured by NMR. The mixture is then cooled to 10 to 25° C. Water (11.16 vol) is added followed by toluene (1.25 vol) and the contents are stirred vigorously for 5 to 15 minutes. The layers are separated. Toluene (1.25 vol) is added to the aqueous layer and the mixture is stirred vigorously for a 5 to 15 minutes. The layers are separated. Toluene (1.25 vol) is added to the aqueous layer, stirred vigorously for 5 to 15 minutes and the layers are separated. The aqueous phase is then cooled to between 0 and 10° C. and acidified with concentrated hydrochloric acid (0.74 vol), maintaining the temperature below 10° C. The mixture is stirred at between 0 and 10° C. for 60 to 90 minutes. The solid is collected by filtration and dried under reduced pressure to give the title compound.

Examples 84b and 85b 4-(2,6-Dioxo-1,3-dipropyl-2,3,6,7-tetrahydro-1H-purin-8-yl)-bicyclo[2.2.2]octane-1-carboxylic acid (VIII, IX, Steps F and G)

4-(6-Amino-2,4-dioxo-1,3-dipropyl-1,2,3,4-tetrahydro-pyrimidin-5-ylcarbamoyl)-bicyclo[2.2.2]octane-1-carboxylic acid methyl ester (VII, Example 83b, 0.760 kg) and isopropanol (3.62 l) are combined. The mixture is stirred under nitrogen and potassium hydroxide (2 M, 3.62 l) is added. The contents are heated at reflux for 3 hr (test for reaction completion by NMR). The mixture is then allowed to cool to 10 to 25° C. Water (8.48 l) is added followed by toluene (0.95 l) and the contents are stirred vigorously for 5 to 15 minutes. The layers are separated. Extraction with toluene (0.95 l) is performed two additional times. The aqueous phase is then cooled to between 0 and 10° C. and acidified with concentrated hydrochloric acid (0.562 l). The mixture is stirred at between 0 and 10° C. for 60 minutes. Solid product is collected by filtration and dried under reduced pressure at 50 to 60° C. to give the title compound.

Example 86a 8-(4-Hydroxymethylbicyclo[2.2.2]oct-1-yl)-1,3-dipropyl-3,7-dihydropurine-2,6dione (X, Step H)

4-(2,6-Dioxo-1,3-dipropyl-2,3,6,7-tetrahydro-1H-purin-8-yl)-bicyclo[2.2.2]octane-1-carboxylic acid (IX, Example 85a, 1 wt) and tetrahydrofuran (11 vol) are mixed under nitrogen. Borane.tetrahydrofuran complex (1 M) in THF (5.1 vol) is added at such a rate as to maintain the internal temperature between 10 to 20°. The mixture is stirred at 10 to 20° for 17 to 20 hours until all of the acid (X) is consumed (TLC; dichloromethane/methanol, 9/1, visualization UV then potassium permanganate). Methanol (4.2 vol) is added to the reaction, prior to heating at reflux for 45 to 75 min. The reaction is cooled to between 15 and 40° and the solvent removed by reduced pressure at 40 to 45°. The residue is partitioned between ethyl acetate (16.6 vol) and hydrochloric acid (1 M, 2.5 vol) and the aqueous layer is removed with any undissolved solid material. This mixture is clarified and the residual organic phase from the filtration of the aqueous layer/solid mixture is combined with the bulk organic phase. Saturated sodium hydrogen carbonate (2.5 vol) is added and the layers separated, retaining any solids with the aqueous phase. This aqueous phase/solid mixture is filtered and the residual organic phase from these mother liquors is combined with the bulk organic phase. The combined organic phases are washed with saline (2.5 vol), the layers are separated and any residual solid is retained with the aqueous phase. The aqueous phase/solid mixture is filtered and any organic in the mother liquors from the filtration is combined with the bulk organic phase, dried with magnesium sulphate (0.5 wt) for 5 to 15 mins, filtered, washed with ethyl acetate (1 vol) and the solvent removed under reduced pressure at 40 to 45° to give the title compound.

Example 86b 8-(4-Hydroxymethyl-bicyclo[2.2.2]oct-1-yl)-1,3-dipropyl-3,7-dihydropurine-2,6-dione (X, Step H)

4-(2,6-Dioxo-1,3-dipropyl-2,3,6,7-tetrahydro-1H-purin-8-yl)-bicyclo[2.2.2]octane-1-carboxylic acid, IX, Example 85b, 0.82 kg) and tetrahydrofuran (9.02 l) are mixed under nitrogen and borane.tetrahydrofuran complex (1 M) in THF (4.18 l) is added at such a rate as to maintain the internal temperature between 10 to 20°. The reaction mixture is stirred at 10 to 20° for 17 hours until all of the starting material is consumed (TLC; dichloromethane/methanol, 9/1; visualization UV then potassium permanganate). Methanol (3.44 l) is added to the reaction mixture, and the mixture is heated to reflux for 1 hr. The reaction is cooled to between 15 and 40° and the solvent removed by reduced pressure at 40 to 45°. The residue is partitioned between ethyl acetate (13.61 l) and hydrochloric acid (1 M, 2.23 l) and the aqueous layer is removed with any undissolved solid material. The mixture is clarified and the residual organic phase from the filtration of the aqueous layer/solid mixture is combined with the bulk organic layer. Saturated sodium hydrogen carbonate (2.23 l) is added and the layers separated, retaining any solids with the aqueous phase. The aqueous phase/solid mixture is filtered and the residual organic phase from these mother liquors are combined with the bulk organic layer. The combined organic layers are washed with saturated saline (2.23 l), the layers are separated and residual solids are retained with the aqueous phase. The aqueous layer/solid mixture is filtered and organics in the mother liquors from the filtration are combined with the bulk organic layer, dried with magnesium sulfate (0.41 kg), filtered, washed with ethyl acetate (0.82 l) and the solvent removed under reduced pressure at 40 to 45° to give the title compound.

Example 87a 4-(2,6-Dioxo-1,3-dipropyl-2,3,6,7-tetrahydro-1H-purin-8-yl)-bicyclo[2.2.2]octane-1-carbaldehyde (XI)

8-(4-Hydroxymethylbicyclo[2.2.2]oct-1-yl)-1,3-dipropyl-3,7-dihydropurine-2,6-dione (X, Example 86a, 1 wt) and dimethyl sulphoxide (4 vol) are mixed and stirred under nitrogen; the mixture is stirred for 5 to 15 mins and triethylamine (2.42 vol) is added. A mixture of sulphur trioxide pyridine complex (1.275 wt) in dimethyl sulphoxide (6 vol) is added, maintaining the internal temperature below 30°. The temperature is adjusted to 14 to 20° and the reaction mixture is then stirred at 14 to 20° for 16 to 20 hours until complete by NMR. If there is any starting alcohol remaining sulphur trioxide pyridine complex (0.15 wt) is added and the reaction stirred for a further 2 to 3 hours at 14 to 20°. Ethyl acetate (20 vol) and hydrochloric acid (1 M, 10 vol) are added to the reaction mixture and stirred vigorously for 5 to 15 mins. The phases are separated and the organic phase is washed with hydrochloric acid (1 M, 10 vol). The phases are separated and the organic phase is again washed with hydrochloric acid (1 M, 10 vol). The phases are separated and the organic phase is washed with saline (5 vol), dried over magnesium sulphate (0.5 wt) for 5 to 10 mins and filtered. The filter cake is washed with ethyl acetate (1 vol). The solvent is removed under reduced pressure at 40 to 45° to give the title compound.

Example 87b 4-(2,6-Dioxo-1,3-dipropyl-2,3,6,7-tetrahydro-1H-purin-8-yl)-bicyclo[2.2.2]octane-1-carbaldehyde (XI, Step I)

8-(4-Hydroxymethyl-bicyclo[2.2.2]oct-1-yl)-1,3-dipropyl-3,7-dihydropurine-2,6-dione (X, Example 8, 0.440 kg) and dimethyl sulphoxide (1.76 l) are mixed under nitrogen, stirred for 5 to 15 mins and triethylamine (1.065 l) is added. A mixture of sulphur trioxide pyridine complex (0.561 kg) in dimethyl sulphoxide (2.64 l) is added, maintaining the internal temperature below 30° C. The internal temperature is adjusted to 14 to 20° C. and the reaction mixture is stirred at 14 to 20° C. for 20 hours. Ethyl acetate (8.80 l) and hydrochloric acid (1 M, 4.40 l) are added to the reaction and the mixture is stirred vigorously for 15 mins. The layers are separated and the organic layer is washed twice more with hydrochloric acid (1 M, 4.40 l). The organic layer is then washed with saline (2.20 l), dried over magnesium sulfate (0.223 kg) for 10 mins, filtered and the filter cake is washed with ethyl acetate (0.440 l). The solvent is evaporated under reduced pressure at 40 to 45° to give the title compound.

Example 88 cis/trans-3-[4-(2,6-Dioxo-1,3-dipropyl-2,3,6,7-tetrahydro-1H-purin-8-yl)-bicyclo[2.2.2]oct-1-yl] acrylic acid methyl ester (XII)

4-(2,6-Dioxo-1,3-dipropyl-2,3,6,7-tetrahydro-1H-purin-8-yl)-bicyclo[2.2.2]octane-1-carbaldehyde (XI, Example 87a, 1 wt) and tetrahydrofuran (16.5 vol) are mixed under nitrogen and methyl(triphenylphosphoranylidene) acetate (1.85 wt) is added. The reaction mixture is heated to 65 to 75° C. and the reaction mixture stirred at this temperature until the starting aldehyde has been consumed as determined by NMR. The mixture is cooled to 35 to 40° C. and a solution of lithium hydroxide (0.45 wt) in water (16.5 vol) is added. The mixture is heated to reflux and the mixture stirred at reflux until the hydrolysis of the ester is complete (as determined by NMR, typical reaction time 3 to 6 hours). The reaction mixture is cooled to 35 to 40° and the organic solvent removed in vacuo at 40 to 45°. Ethyl acetate (10 vol) and water (6 vol) are added to the aqueous residue and the mixture is vigorously stirred for 5 to 15 mins. The phases are separated and the aqueous phase is washed with ethyl acetate (2×10 vol). The aqueous phase is filtered. The filtrate is cooled to 0 to 5° and acidified to pH=1 with concentrated hydrochloric acid (0.90 vol). The mixture is stirred at 0 to 5° for 45 to 75 mins. The resultant slurry is filtered and the filter pad washed with water (1 vol). The solid is dried in vacuo at 45 to 55° for 16 to 24 hours to give the title compound.

Examples 89

3-[4-(2,6-Dioxo-1,3-dipropyl-2,3,6,7-tetrahydro-1H-purin-8-yl)-bicyclo[2.2.2]oct-1-yl]-acrylic acid (XIII, Steps J and K)

4-(2,6-Dioxo-1,3-dipropyl-2,3,6,7-tetrahydro-1H-purin-8-yl)-bicyclo[2.2.2]octane-1-carbaldehyde (XI, Example 97b, 0.300 kg) and tetrahydrofuran (4.95 l) are mixed under an atmosphere of nitrogen and methyl (triphenylphosphoranylidene) acetate (0.555 kg) is added. The reaction mixture is heated to 65 to 75° and the reaction mixture stirred at this temperature until the starting aldehyde is consumed (17 hours). The mixture is cooled to 35 to 40° and a mixture of sodium hydroxide (0.132 kg) in water (4.95 l) is added. The mixture is heated to reflux and stirred until the hydrolysis of the ester is complete (3 hours). The reaction mixture is cooled to 35 to 40° and the organic solvent removed in vacuo at 40 to 45°. Ethyl acetate (3.00 l) and water (1.80 l) are added to the aqueous residue and the mixture is vigorously stirred for 15 mins. The layers are separated and the aqueous layer is washed with ethyl acetate (2×3.00 l). The aqueous layer is filtered, the filtrate is cooled to 0 to 5° and acidified to pH=1 with concentrated hydrochloric acid (0.270 l). The mixture is stirred at 0 to 5° for 1 hour. The resultant slurry is filtered and the filter pad washed with water (0.300 l). The solid is dried in vacuo at 45 to 55° for 24 hours to the title compound.

Example 90

3-[4-(2,6-Dioxo-1,3-dipropyl-2,3,6,7-tetrahydro-1H-purin-8-yl)-bicyclo[2.2.2]oct-1-yl]propionic acid (XIV)

3-[4-(2,6-Dioxo-1,3-dipropyl-2,3,6,7-tetrahydro-1H-purin-8-yl)-bicyclo[2.2.2]oct-1-yl]-acrylic acid, (XIII, Example 89, 1.934 kg), tetrahydrofuran (11.875 l), water (0.625 l) and activated charcoal (0.100 kg) are mixed and stirred at 16 to 25° for 30 minutes and then filtered. The filter cake is washed with THF (0.500 l). A separate flask is charged with palladium on carbon (10%, 0.130 kg) and the filtered tetrahydrofuran/water mixture of the starting material. The flask is placed under reduced pressure and purged with nitrogen. The reduced pressure/nitrogen purge is repeated twice. The flask and contents are placed under reduced pressure and purged twice with hydrogen. The mixture is vigorously stirred under an atmosphere of hydrogen at 20° C. for 3 hours. The reaction vessel is evacuated and purged with nitrogen three times. The contents are filtered through celite (0.500 kg) and the filter cake washed with tetrahydrofuran (2×0.500 l). The solvent is removed under reduced pressure at 40 to 45°. Aqueous acetonitrile (50%, 7.540 l) is added to the residue and the slurry is aged at 15 to 25°, with stirring, for 3 hours. The slurry is cooled to between 0 and 5° and filtered. The filter cake is washed with aqueous acetonitrile (50%, 1.93 l), transferred to drying trays and dried at 50 to 60° under reduced pressure for 24 hours to give the title compound.

Example 91

4-Hydroxymethylbicyclo[2.2.2]octano-1-carboxylic acid methyl ester (XVI, Step M)

4-methyl morpholine (15 ml, 136 mmol) and iso-butyl chloroformate (15.0 ml, 123 mmol) are successively added to bicyclo[2.2.2]octane-1,4-dicarboxylic acid monomethyl ester (IV) in DME (165 ml), cooled to −7° C.

After about 2 minutes, the reaction mixture is filtered and the solid is rinsed with DME. The combined filtrates are transferred to a two liter round-bottomed flask and cooled to −5° C. An aqueous solution of sodium borohydride (7.02 g, 185 mmol), in 75 ml water is added over about 1 minute (CAUTION: massive evolution of gas). After 10 minutes, the reaction mixture is diluted with water (100 ml) and extracted with ethyl acetate (3×250 ml). The combined organic layers are washed with saline (150 ml×3), dried over anhydrous sodium sulfate and concentrated to give the title compound.

Example 92

4-Hydroxymethylbicyclo[2.2.2]octane-1-carboxylic acid (XVII, Step N)

Lithium hydroxide (2 N, 250 ml) is added to a mixture of 4-hydroxymethyl-bicyclo[2.2.2]octane-1-carboxylic acid methyl ester (XVI, Example 91) in a mixture of THF (50 ml) and methanol (75 ml). The resulting reaction mixture is stirred at 20–25° for 16 hr, and then concentrated. The residue is diluted with water (30 ml) and washed with methylene chloride (100 ml) and ethyl acetate (100 ml). The aqueous layer is acidified with concentrated hydrochloric acid pH about 0 and extracted with ethyl acetate (3×250 ml). The ethyl acetate layers are combined and washed with saline (3×50 ml), dried over anhydrous sodium sulfate and concentrated to give the title compound, NMR (400 MHz, CDCl$_3$) δ 3.09, 1.72 and 1.29.

Example 93

4-Hydroxymethylbicyclo[2.2.2]octane-1-carboxylic acid benzyl ester (XVIII, Step O)

4-Hydroxymethylbicyclo[2.2.2]octane-1-carboxylic acid (XVII, Example 14, 24.8 g 135 mmol) is dissolved in DMF (950 ml). Anhydrous potassium carbonate (25 g, 181 mmol) is added to the solution slowly. Benzyl bromide (22 g, 12.94 mmol) is then added. The reaction mixture is heated at 80° for 16 hr. To the reaction mixture is added water (150 ml) and concentrated to give an oil, which was dissolved in ethyl acetate/hexane (5/1, 500 ml). The mixture is washed with saline (2×200 ml), dried over anhydrous sodium sulfate and concentrated to give the title compound, NMR (400 MHz, CDCl$_3$) δ 7.39, 5.11, 3.28, 1.84 and 1.41.

Example 94

4-Formylbicyclo[2.2.2]octane-1-carboxylic acid benzyl ester (XIX, Step P)

Oxalyl chloride (COCl)$_2$ (16.5 ml, 188 mmol) in methylene chloride (150 ml) is cooled to −63°. DMSO (18 ml, 362 mmol) is then added dropwise. The resulting mixture is stirred for 30 minutes and then a mixture of 4-hydroxymethylbicyclo[2.2.2]octane-1-carboxylic acid benzyl ester (XVIII, Example 93, 34.5 g, 125 mmol) in methylene chloride (100 ml) is added over 15 minutes. After another 30 minutes, triethylethylamine (70 ml, 502 mmol) in methylene chloride (30 ml) is added over 25 minutes. (Extra Caution: extremely exothermic reaction when the first equivalent of the triethylamine is added.) The reaction mixture then stirred for another 45 minutes and the cooling bath is removed and allowed to warm up to 20–25°. Water (50 ml) is added and the organic layer is separated, dried over anhydrous sodium sulfate and concentrated to give the title compound, NMR (400 MHz, CDCl$_3$) δ 9.51, 7.32, 5.11, 1.88 and 1.64.

Example 95 cis/trans-4-(2-Methoxycarbonylvinyl)bicyclo[2.2.2] octane-1-carboxylic acid benzyl ester (XX, Step Q)

Methyl (triphenylphosphoranylidene) acetate (60.2 g, 173 mmol) is added to a stirred solution of 4-formylbicyclo

[2.2.2]octane-1-carboxylic acid benzyl ester (XIX, Example 94, 33.5 g, 123.2 mmol) in THF (550 ml). This mixture is then heated to gently reflux for 16 hr. The reaction mixture is cooled to 20–25° and to this is added saturated ammonium chloride (75 ml) and stirred for 10 minutes. Ethyl acetate (250 ml) and isomeric hexanes (300 ml) are added and stirred for 10 minutes. The resulting mixture is filtered through a plug of silica gel (850 g) with a thin layer of celite on the top. The solid is washed with ethyl acetate/hexane (1/1, 250 ml). The filtrates are combined and concentrated to give the title compound, NMR (400 MHz, CDCl$_3$) δ 7.24, 6.81, 5.59, 5.01, 3.63, 1.81 and 1.48.

Example 96

4-(2-Methoxycarbonylethyl)bicyclo[2.2.2]octane-1-carboxylic acid (XXI, Step R)

4-(2-Methoxycarbony-vinyl)-bicyclo[2.2.2]octane-1-carboxylic acid benzyl ester (XX, Example 95, 35 g, 106.6 mmol) is dissolved in ethyl alcohol/water (9/1, 300 ml) and is placed in a Porter pressure bottle. Palladium on carbon (10%, 5 g) is added and the mixture is hydrogenated (65 psi) for 48 hr. The reaction mixture is filtered through a pad of celite and the combined filtrates were concentrated to give the title compound, NMR (400 MHz, CDCl$_3$) δ 3.58, 2.18, 1.74, 1.44 and 1.38.

Example 97

3-(4-Chlorocarbonylbicyclo[2.2.2]oct-1-yl)propionic acid methyl ester (XXII, Step S)

Oxalyl chloride (794 mg, 6.25 mmol) in methylene chloride (5 ml) plus a drop of DMF is slowly added to a mixture of 4-(2-methoxycarbonyethyl)-bicyclo[2.2.2]octane-1-carboxylic acid (XXI, Example 96,1.2 g, 5 mmol) in methylene chloride (20 ml). The reaction mixture is stirred for 2 hr and concentrated to give the title compound, NMR (400 MHz, CDCl$_3$) δ 3.66, 2.29, 1.95, 1.54 and 1.46.

Example 98

3-[4-(6-Amino-2,4-dioxo-1,3-dipropyl-1,2,3,4-tetraydropyrimidin-5-ylcarbamoyl)bicyclo[2.2.2]oct-1-yl]propionic acid methyl ester (XXIII, Step T)

To a suspension of 5,6-diamino-1,3-dipropyl uracil hydrochloride (1.45 g, 5.5 mmol) in methylene chloride (15 ml) is added triethylamine (2.6 ml, 18.7 mmol) slowly at −10° in an ice bath and to this ias added a mixtue of 3-(4-chlorocarbonyl-bicyclo[2.2.2]oct-1-yl)-propionic acid methyl ester (XXII, Example 97,1.3 g, 5 mmol) also in methylene chloride (5 ml) over a period of 10 minutes. The reaction is then warmed to 20–25° and the stirring is continued for another 16 hrs. Water (2 ml) is added to the reaction mixture which is then concentrated. The concentrate is dissolved in ethyl acetate (20 ml) and is washed with citric acid (5% citric acid, 2×10 ml), saline (10 ml), dried over anhydrous sodium sulfate and concentrated to give the title compound, NMR (400 MHz, CDCl$_3$) δ 7.40, 5.46, 3.81, 3.59, 2.21, 1.88, 1.67, 1.62, 1.52, 1.46, 0.99 and 0.92.

Example 99

3-[4-(2,6-Dioxo-1,3-dipropyl-2,3,6,7-tetrahydro-1H-purin-8-yl)bicyclo[2.2.2]oct-1-yl]propionic acid methyl ester (XXIV, Step U)

See Example 100; 3-[4-(2,6-dioxo-1,3-dipropyl-2,3,6,7-tetrahydro-1H-purin-8-yl)bicyclo[2.2.2]oct-1-yl]propionic acid methyl ester (XXIV) is produced in situ and converted to the free acid in Example 100 as part of a one pot procedure.

Example 100

3-[4-(2,6-Dioxo-1,3-dipropyl-2,3,6,7-tetrahydro-1H-purin-8-yl)-bicyclo[2.2.2]oct-1-yl]propionic acid (XIV, Step V)

3-[4-(6-Amino-2,4-dioxo-1,3-dipropyl-1,2,3,4-tetraydropyrimidin-5-ylcarbamoyl)bicyclo[2.2.2]oct-1-yl] propionic acid methyl ester (XXIII, Example 98, 1.95 g, 4.35 mmol) is dissolved in 2-propanol (15 ml) and potassium hydroxide (2N, 15 ml) is added. The resulting mixture is heated to slightly refluxing for an hour and then is cooled to 20–25° C. Water (15 ml) is added and the mixture is washed with methylene chloride (3×15 ml). The aqueous layer is acidified to pH about 2 with concentrated hydrochloric acid. The precipitate is collected by filtration and dried in a vacuum oven for 16 hr to give the title compound, HPLC analysis showed the purity was >96%.

Example 101 cis/trans-1-(2-Iodoethyl)-cyclohexane-1,4-dicarboxylic acid dimethyl ester (XXV)

A mixture of cis/trans-1-(2-chloroethyl)-cyclohexane-1,4-dicarboxylic acid dimethyl ester (II Example 79, 8.1 mmol, 2.12 g), sodium iodide (8.88 mmol, 1.33 g) and THF (20 ml) are stirred and refluxed 6 hr. The mixture is cooled to 20–25°, diluted with hexanes (50 ml) and washed with water (2×25 ml). The combined aqueous washes are extracted with hexanes (1×25 ml). The combined organic extracts are washed with water (25 ml) to which has been added a few drops of saturated Na$_2$S$_2$O$_4$ solution and saline (1×25 ml) and dried over magnesium sulfate. Suction filtration and concentration under reduced pressure gives the title compound, CMR (CDCl$_3$) δ 1.99, 25.71, 25.80, 33.09, 42.00, 44.03, 46.09, 52.19, 52.7, 67.72, 175.25 and 175.64.

Example 102

Bicyclo[2.2.2]octane-1,4-dicarboxylic acid dimethyl ester (III)

To a mixture of cis/trans-1-(2-iodoethyl)-cyclohexane-1,4-dicarboxylic acid dimethyl ester (XXV, Example 101, 2.14 g, 6.04 mmol) in THF (20 ml) and TMU (2.9 ml, 24.16 mmol) is added at −78° a solution of LDA (from 1.02 ml diisoproylamine and 4.16 ml 1.6 M n-butyllithium) in THF (9 ml). The reaction is stirred with gradual warming to 20–25°. Hydrochloric acid (3N, 20 ml) is added and briskly stirred 10 min. The THF is removed under reduced pressure and the resulting aqueous residue is extracted with hexanes (2×20 ml). The combined organic extracts are washed with hydrochloric acid (3N, 2×20 ml), water (1×10 ml), saturated sodium bicarbonate (2×10 ml) and saline (1×10 ml) and dried over magnesium sulfate. Suction filtration and concentration under reduced pressure gives the title compound, NMR (CDCl$_3$) δ 1.78 and 3.6; CMR (CDCl$_3$) δ 27.99, 39.98, 53.12 and 177.62.

Example 103

4-(Hydroxymethyl-bicyclo[2.2.2]oct-1-yl)-1,3-dipropyl-2,6-purine-dione (XXVI, Steps Y and Z)

4-(6-Amino-2,4-dioxo-1,3-dipropyl-1,2,3,4-tetrahydropyrimidin-5-ylcarbamoyl)-bicyclo[2.2.2]octane-1- carboxylic acid methyl ester (VII, Example 83, 0.500 g) is dissolved in THF (10 ml) and placed under nitrogen. At 25° C., lithium borohydride (0.052 g) is added and the mixture is stirred at reflux for 2 hours. The solvent is removed under reduced pressure. To the crude product is added potassium hydroxide (1 M, 3.57 ml) and isopropanol (4 ml). The mixture is brought to reflux for 1 hour to give the title compound.

Example 104

3-[4-(2,6-Dioxo-1,3-dipropyl-2,3,6,7-tetrahydro-1H-purin-8-yl)-bicyclo[2.2.2]oct-1-yl]-acrylic acid (XII, Steps AA and BB)

4-(2,6-Dioxo-1,3-dipropyl-2,3,6,7-tetrahydro-1H-purin-8-yl)-bicyclo[2.2.2]octane-1-carbaldehyde (XI, Example 9, 0.490 g, 1.32 mmol) is added to a mixture of malonic acid (0.275 g, 2.64 mmol), pyridine (2 ml), and piperidine (1 drop). The mixture is heated to 100° for 16 hours. Four additional equivalents of malonic acid are added and heating continued for another 16 hours until consumption of aldehyde ceases, to give the title compound.

Example 105

3-[4-(2,6-Dioxo-1,3-dipropyl-2,3,6,7-tetrahydro-1H-purin-8-yl)-bicyclo[2.2.2]oct-1-yl]-acrylic acid ethyl ester (XXVIII, XII, Steps CC and DD).

cis/trans-3-[4-(2,6-Dioxo-1,3-dipropyl-2,3,6,7-tetrahydro-1H-purin-8-yl)-bicyclo[2.2.2]oct-1-yl]acrylic acid ethyl ester (XII) is obtained by an aldol reaction between aldehyde (XI) (1 equivalent) and ethyl acetate (4.7 equivalents) in the presence of a strong base such as sodium ethoxide (1.2 equivalents).

Example 106

Methanesulfonic acid 4-(2,6-dioxo-1,3-dipropyl-2,3,6,7-tetrahydro-1H-purin-8-yl)-bicyclo[2.2.2]oct-1-ylmethyl ester (XL)

To a mixture of 8-(4-hydroxymethylbicyclo[2.2.2]oct-1-yl)-1,3-dipropyl-3,7-dihydropurine-2,6-dione (X, Example 86) in pyridine at 0° is added methanesulfonyl chloride (1.2 equivalents) in pyridine. The mixture is stirred at 0° until complete conversion is achieved and then the solvent removed under reduced pressure.

Example 107

2-[4-(2,6Dioxo-1,3-dipropyl-2,3,6,7-tetrahydro-1H-purin-8-yl)-bicyclo[2.2.2]oct-1-ylmethyl]-malonic acid dimethyl ester (XLI)

Methanesulfonic acid 4-(2,6-dioxo-1,3-dipropyl-2,3,6,7-tetrahydro-1H-purin-8-yl)-bicyclo[2.2.2]oct-1-ylmethyl ester (XL, Example 106) is reacted with the anion of dimethyl malonate (formed from the reaction of 1 equivalent of dimethyl malonate with 1.25 equivalents of sodium hydride or similar base in THF) at 20–25° gives the title compound.

Example 108

3-[4-(2,6Dioxo-1,3-dipropyl-2,3,6,7-tetrahydro-1H-purin-8-yl)-bicyclo[2.2.2]oct-1-yl]-propionic acid methyl ester (XXXV)

Hydrolysis of 2-[4-(2,6-dioxo-1,3-dipropyl-2,3,6,7-tetrahydro-1H-purin-8-yl)-bicyclo[2.2.2]oct-1-ylmethyl] malonic acid dimethyl ester (XLI, Example 107) with hydroxide at elevated temperature gives the title compound.

Example 109

Bicyclo[2.2.2]octane-1,4-dicarboxylic acid dimethyl ester (III)

A mixture of cis/trans-1-(2-chloroethyl)-cyclohexane-1,4-dicarboxylic acid dimethyl ester (I, 7.63 mmol, 2.00 g), sodium iodide (8.39 mmol, 1.26 g) and THF (20 ml) are stirred and refluxed 6 hr. The mixture is cooled to 20–25°, TMU (30.52 mmol, 3.65 ml) is added and the mixture cooled to −78° C. To the cold mixture is added a solution of LDA (from 1.28 ml diisoproylamine and 5.25 ml 1.6 M n-butyllithium) in THF (11 ml). The reaction is stirred with gradual warming to 20–25° C. Hydrochloric acid (3N, 20 ml) is added and briskly stirred 10 min. The THF is removed under reduced pressure and the resulting aqueous residue is extracted with hexanes (2×20 ml). The combined organic extracts are washed with hydrochloric acid (3N, 2×20 ml), water (1×10 ml), saturated sodium bicarbonate (2×10 ml) and saline (1×10 ml) and dried over magnesium sulfate. Suction filtration and concentration under reduced pressure gives the title compound.

Example 110

Bicyclo[2.2.2]octane-1,4-dicarboxylic acid dimethyl ester (III, Step TT)

To a stirred solution of diisopropylamine (84.5 ml, 600 mmol) in THF (anhydrous, 700 ml) cooled to −30° C. under nitrogen is added n-butyl lithium (2.5 M in hexane, 220 ml, 550 mmol) by a syringe. The misture is stirred for 30 min at −30° C. and then cooled to −78° C. HMPA (360 ml, 4 equivalents, 2 mol) is added by a syringe and a dolution of dimethyl cyclohexane-1,4-dicarboxylate (100 g, 500 mmol) in THF (anhydrous, 100 ml is added by a syringe subsequently. The mixture is stirred for an additional 40 min. Then 1-bromo-2-chloroethane (41.5 ml, 500 mmol) is added and the mixture stirred at −78° C. for an additional 20 min. The cold bath is removed and stirring is continued for 1 hr. The reaction mixture is cooled back to −78° and a mixture of HMPA (360 ml, 4 eq, 2 mol) in THF 600 ml) is added. By cannula, freshly prepared LDA (200 ml of n-butyl lithium, 2.5 M in hexane, 500 mmol is added to diisopropylamine (78 ml, 556 mmol) in THF (anhydrous, 700 ml)) is transferred into the reaction mixture at −78°. The reaction mixture is stirred at −78° for 1.33 hr followed by removal of the cooling bath and additional stirring for 5–6 hr. The mixture is quenched with saturated aqueous ammonium chloride (400 ml) and concentrated under reduced pressure at 35° to remove the THF. The residue is diluted with water (800 ml) and extracted with hexance (3×600 ml). The combined extracts are washed with saline (700 ml) and dried over sodium sulfate. Using a bath temperature of 35° the solvents are are removed under reduced pressure to give a residue. The residue is stirred with hexane (50 ml) at 20–25° for 0.5 hr. The resulting suspension is cooled to 0° for 2 hr and filtered to give the title compound.

Example 111

Assay Methodology

One hundred eighty-four xanthine derivatives were prepared, having the structures indicated in FIG. 2. For some of these compounds, the $K_i$ values for rat and human adenosine $A_1$ receptors and for human adenosine $A_{2a}$ receptors were determined according to the following binding assay protocol. The ratio $A_{2a}/A_1$ was also calculated.

Materials

Adenosine deaminase and HEPES were purchased from Sigma (St. Louis, Mo.). Ham's F-12 cell culture medium and fetal bovine serum were purchased from GIBCO Life Technologies (Gaithersburg, Md.). Antibiotic G-418, Falcon 150 mM culture plates and Costar 12-well culture plates were purchased from Fisher (Pittsburgh, Pa.). [$^3$H]CPX was purchased from DuPont-New England Nuclear Research Products (Boston, Ma.). Penicillin/streptomycin antibiotic mixture was purchased from Mediatech (Washington, D.C.). The composition of HEPES-buffered Hank's solution was: 130 mM NaCl, 5.0 mM Cl, 1.5 mM $CaCl_2$, 0.41 mM $MgSO_4$, 0.49 mM $Na_2HPO_4$, 0.44 mM $KH_2PO_4$, 5.6 mM dextrose, and 5 mM HEPES (pH 7.4).

Membrane Preparation

Rat $A_1$ Receptor:

Membranes were prepared from rat cerebral cortex isolated from freshly euthanized rats. Tissues were homogenized in buffer A (10 mM EDTA, 10 mM Na-HEPES, pH 7.4) supplemented with protease inhibitors (10 µg/ml benzamidine, 100 µM PMSF, and 2 µg/ml each of aprotinin, pepstatin and leupeptin), and centrifuged at 20,000×g for 20 min. Pellets were resuspended and washed twice with buffer HE (10 mM Na-HEPES, 1 mM EDTA, pH 7.4, plus protease inhibitors). Final pellets were resuspended in buffer HE, supplemented with 10% (w/v) sucrose and protease inhibitors, and frozen in aliquots at −80° C. Protein concentrations were measured using BCA protein assay kit (Pierce).

Human $A_1$ Receptor:

Human A1 adenosine receptor cDNA was obtained by RT-PCR and subcloned into pcDNA3.1(Invitrogen). Stable transfection of CHO-K1 cells was performed using LIPOFECTAMINE-PLUS (GIBCO-BRL) and colonies were selected in 1 mg/ml G418, and screened using radioligand binding assays. For membrane preparations, CHO-K1 cells growing as monolayers in complete media (F12+ 10% FCS+1 mg/ml G418) were washed in PBS and harvested in buffer A supplemented with protease inhibitors. Cells were homogenized, centrifuged, and washed twice with buffer HE as described above. Final pellets were stored in aliquots at −80° C.

Radioligand Binding Assays

Membranes (50 µg membrane protein for rat A1ARs, and 25 µg of CHO-K1 membrane protein for human A1ARs), radioligands and varying concentrations of competing ligands were incubated in triplicates in 0.1 ml buffer HE plus 2 units/ml adenosine deaminase for 2.5 h at 21° C. Radioligand [$^3$H]DPCPX (112 Ci/mmol from NEN, final concentration:1 nM) was used for competition binding assays on $A_1$ARs. Nonspecific binding was measured in the presence of 10 µM BG9719. Binding assays were terminated by filtration over Whatman GF/C glass fiber filters using a BRANDEL cell harvester. Filters were rinsed three times with 3–4 ml ice-cold 10 mM Tris-HCl, pH 7.4 and 5 mM $MgCl_2$ at 4° C. Filter paper was transferred to a vial, and 3 ml of scintillation cocktail ScintiVerseII (Fisher)was added. Radioactivity was counted in a Wallac β-counter.

Analysis of Binding Data

For $K_I$ Determinations:

Competition binding data were fit to a single-site binding model and plotted using Prizm GraphPad. Cheng-Prusoff equation $K_I=IC_{50}/(1+[I]/K_D)$ was used to calculate $K_I$ values from $IC_{50}$ values, where $K_I$ is the affinity constant for the competing ligand, [I] is the concentration of the free radioligand, and $K_D$ is the affinity constant for the radioligand.

For % Binding:

For one-point binding assays, data were presented as % of total specific binding at 1 µM of competing compound: % of total=100* (Specific binding with 1 µM of competing compound/total specific binding).

Results

All of the compounds tested exhibited rat $A_1$ $K_i$ values between 0.6 and 433.8 nM, human $A_1$ $K_i$ values between 1.6 and 1000 nM, and human $A_{2a}$ $K_i$ values between 132 and 49930 nM. All of the compounds had $A_{2a}/A_1$ ratios greater than 10, most greater than 20, many greater than 50, and some greater than 100. At least one compound had a $A_{2a}/A_1$ ratio greater than 1000.

Example 112

Alternative Assay Methodology Materials

See Example 111.

Cell Culture

CHO cells stably expressing the recombinant human $A_1$AdoR (CHO:$A_1$AdoR cells) were prepared as described (Kollias-Barker et al., J. Pharma. Exp. Ther. 281(2), 761, 1997) and cultured as for CHO:Wild cells. CHO cells were cultured as monolayers on plastic dishes in Ham's F-12 medium supplemented with 10% fetal bovine serum, 100 U penicillin G and 100 µg streptomycin in a humidified atmosphere of 5% $CO_2$/95% air at 37° C. The density of [$^3$H]CPX binding sites in CHO cells was 26±2 (n=4) mol/mg protein. Cells were subcultured twice weekly after detachment using 1 mM EDTA in $Ca^{2+}$—$Mg^{2+}$—free HEPES-buffered Hank's solution. Three different clones of CHO:$A_1$AdoR cells were used for experiments, and all results were confirmed with cells from two or three clones. The density of $A_1$AdoRs in these cells was 4000–8000 fmol/mg protein, as determined by assay of [$^3$H]CPX specific binding.

Radioligand Binding

CHO cells grown on 150 mm culture dishes were rinsed with HEPES-buffered Hank's solution, then removed with a cell scraper and homogenized in ice-cold 50 mM Tris-HCl, pH 7.4. Cell membranes were pelleted by centrifugation of the cell homogenate at 48,000×g for 15 minutes. The membrane pellet was washed twice by resuspension in fresh buffer and centrifugation. The final pellet was resuspended in a small volume of 50 mM Tris-HCl, pH 7.4, and stored in aliquots of 1 ml at −80° C. until used for assays.

To determine the density of $A_1$AdoRs in CHO cell membranes, 100 µl aliquots of membranes (5 µg protein) were incubated for 2 hours at 25° C. with 0.15–20 nM [$^3$H]CPX and adenosine deaminase (2 U/ml) in 100 µl of 50 mM Tris-HCl, pH 7.4. Incubations were terminated by dilution with 4 ml of ice-cold 50 mM Tris-HCl buffer and immediate collection of membranes onto glass-fiber filters (Schleicher and Schuell, Keene, N.H.) by vacuum filtration (Brandel, Gaithersburg, Md.). Filters were washed quickly three times with ice-cold buffer to remove unbound radioligand. Filter discs containing trapped membranes bound radioligand were placed in 4 ml of Scintiverse BD (Fisher), and the radioactivity was quantified using a liquid scintillation counter. To determine nonspecific binding of [$^3$H] CPX, membranes were incubated as described above and 10 µM CPT was added to the incubation buffer. Nonspecific binding was defined as [$^3$H]CPX bound in the presence of 10 µM CPT. Specific binding of the radioligand to the $A_1$AdoR was determined by subtracting nonspecific binding from total binding. Nonspecific binding was found to increase linearly with an increase of [$^3$H]CPX concentration. Triplicate assays were done at each tested concentration of [$^3$H] CPX.

To determine the affinities of antagonists of $A_1AdoRs$ for the human recombinant $A_1AdoR$ expressed in CHO cells, binding of 2 nM [$^3$H]CPX in the presence of increasing concentrations of antagonist was measured. Aliquots of CHO cell membranes (100 μl: 5 μg protein), [$^3$H]CPX, antagonist (0.1 nM–100 μM), and adenosine deaminase (2 U/ml) were incubated for 3 hours at 25° C. in 200 μl of 50 mM Tris-HCl buffer (pH 7.4). Assays were terminated as described above.

Data Analysis

Binding parameters (i.e., $B_{max}$, $K_d$, $IC_{50}$, $K_i$, and Hill coefficients) were determined using the radioligand binding analysis program LIGAND 4.0 (Elsevier-Biosoft).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound comprising the formula:

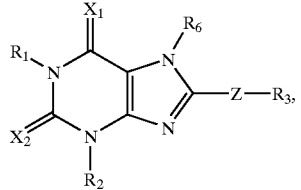

or a pharmaceutically acceptable addition salt thereof;
wherein $R_1$ and $R_2$ are independently selected from the group consisting of:
a) hydrogen;
b) alkyl, alkenyl of not less than 3 carbons, or alkynyl of not less than 3 carbons; wherein said alkyl, alkenyl, or alkynyl is either unsubstituted or substituted with one or more substituents selected from the group consisting of hydroxy, alkoxy, amino, alkylamino, dialkylamino, heterocyclyl, acylamino, alkylsulfonylamino, and heterocyclylcarbonylamino; and
c) aryl or substituted aryl;
$R_3$ is a bicyclic, tricyclic or pentacyclic group selected from the group consisting of:

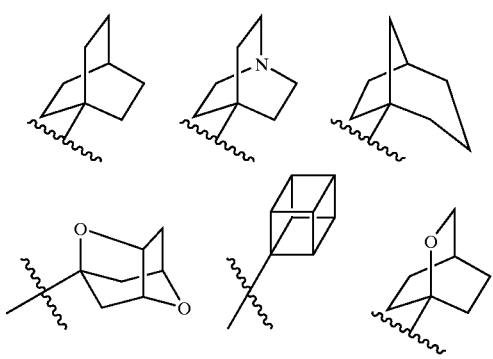

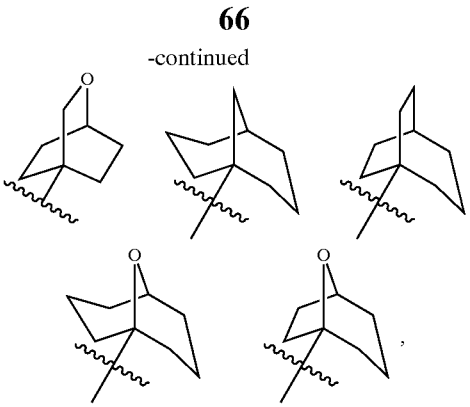

wherein the bicyclic or tricyclic group is either unsubstituted or substituted with one or more substituents selected from the group consisting of:
(a) alkyl, alkenyl, and alkynyl; wherein each alkyl, alkenyl, or alkynyl group is either unsubstituted or functionalized with one or more substituents selected from the group consisting of (amino)($R_5$) acylhydrazinylcarbonyl, (amino)($R_5$) acyloxycarboxy, (hydroxy)(carboalkoxy) alkylcarbamoyl, acyloxy, aldehyde, alkenylsulfonylamino, alkoxy, alkoxycarbonyl, alkylaminoalkylamino, alkylphosphono, alkylsulfonylamino, carbamoyl, $R_5$, $R_5$-alkoxy, cyano, cyanoalkylcarbamoyl, cycloalkylamino, dialkylamino, dialkylaminoalkylamino, dialkylphosphono, haloalkylsulfonylamino, (heterocyclylalkyl)amino, heterocyclylcarbamoyl, hydroxy, hydroxyalkylsulfonylamino, oximino, phosphono, substituted aralkylamino, substituted arylcarboxyalkoxycarbonyl, substituted heteroarylsulfonylamino, substituted heterocyclyl, thiocarbamoyl, and trifluoromethyl; and
(b) (alkoxycarbonyl)aralkylcarbamoyl, aldehydo, alkenoxy, alkenylsulfonylamino, alkoxy, alkoxycarbonyl, alkylcarbamoyl, alkoxycarbonylamino, alkylsulfonylamino, alkylsulfonyloxy, amino, aminoalkylaralkylcarbamoyl, aminoalkylcarbamoyl, aminoalkylheterocyclylalkylcarbamoyl, aminocycloalkylalkylcycloalkylcarbamoyl, aminocycloalkylcarbamoyl, aralkoxycarbonylamino, arylheterocyclyl, aryloxy, arylsulfonylamino, arylsulfonyloxy, carbamoyl, —$R_5$, $R_5$-alkoxy, $R_5$-alkyl(alkyl)amino, $R_5$-alkylalkylcarbamoyl, $R_5$-alkylcarbamoyl, $R_5$-alkylsulfonyl, $R_5$-alkylsulfonylamino, $R_5$-alkylthio, $R_5$-heterocyclylcarbonyl, cyano, cycloalkylamino, dialkylaminoalkylcarbamoyl, halogen, heterocyclyl, (heterocyclylalkyl)amino, hydroxy, oximino, substituted aralkylamino, substituted heterocyclyl, substituted heterocyclylsulfonylamino, sulfoxyacylamino, and thiocarbamoyl;
$R_4$ is selected from the group consisting of hydrogen, $C_{1-4}$-alkyl, $C_{1-4}$-alkyl-$CO_2H$, and phenyl, wherein the $C_{1-4}$-alkyl, $C_{1-4}$-alkyl-$CO_2H$, and phenyl groups are either unsubstituted or substituted with one to three substituents selected from the group consisting of halogen, —OH, —OMe, —$NH_2$, $NO_2$, benzyl, and benzyl substituted with one to three substituents selected from the group consisting of halogen, —OH, —OMe, —$NH_2$, and —$NO_2$;

$R_5$ is selected from the group consisting of —$CH_2COOH$, —$C(CF_3)_2OH$, —$CONHNHSO_2CF_3$, —$CONHOR_4$, —$CONHSO_2R_4$, —$CONHSO_2NHR_4$, —$C(OH)R_4PO_3H_2$, —$NHCOCF_3$, —$NHCONHSO_2R_4$, —$NHPO_3H_2$, —$NHSO_2R_4$, —$NHSO_2NHCOR_4$, —$OPO_3H_2$, —$OSO_3H$, —$PO(OH)R_4$, —$PO_3H_2$, —$SO_3H$, —$SO_2NHR_4$, and the following:

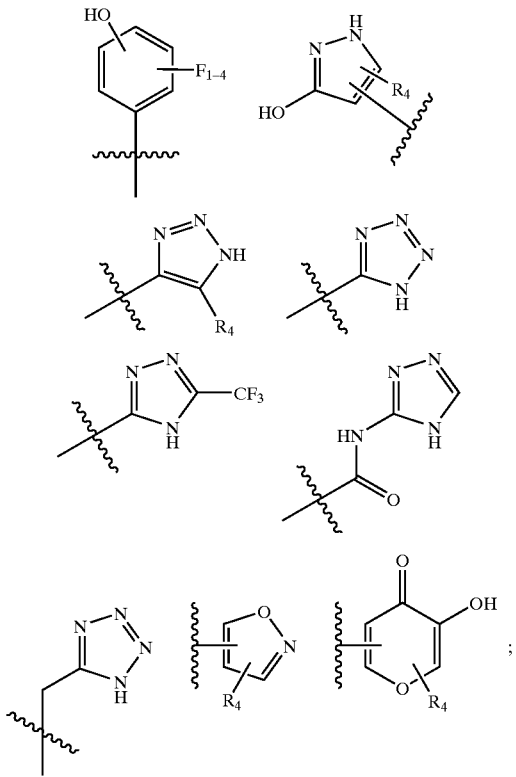

$X_1$ and $X_2$ are independently selected from the group consisting of O and S;

Z is selected from the group consisting of a single bond, —O—, —$(CH_2)_{1-3}$—, —$O(CH_2)_{1-2}$—, —$CH_2OCH_2$—, —$(CH_2)_{1-2}O$—, —$CH=CHCH_2$—, —$CH=CH$—, and —$CH_2CH=CH$—; and $R_6$ is selected from the group consisting of hydrogen, alkyl, acyl, alkylsulfonyl, aralkyl, substituted aralkyl, substituted alkyl, and heterocyclyl.

2. The compound of claim 1, wherein the compound is in a form selected from the group consisting of an achiral compound, a racemate, an optically active compound, a pure diastereomer, a mixture of diastereomers, and a pharmacologically acceptable addition salt.

3. The compound of claim 1, wherein $R_1$ and $R_2$ are each alkyl groups.

4. The compound of claim 1, wherein $R_1$ and $R_2$ are each n-propyl.

5. The compound of claim 1, wherein $R_1$ is n-propyl and $R_6$ is selected from the group consisting of an unsubstituted aralkyl; aralkyl substituted with —OH, —OMe, or -halogen; methyl; and 3-hydroxypropyl.

6. The compound of claim 4, wherein Z is a single bond.

7. The compound of claim 6, wherein $R_3$ is:

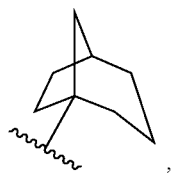

and wherein $R_3$ is either unsubstituted or substituted with one or more substituents selected from the group consisting of hydroxy, $R_5$-, and $R_5$-alkenyl.

8. The compound of claim 7, wherein the compound is 5-(2,6-Dioxo-1,3-dipropyl-2,3,6,7-tetrahydro-1H-purin-8-yl)-bicyclo[3.2.1]octane-1-carboxylic acid.

9. The compound of claim 7, wherein the compound is 8-(4-Hydroxy-bicyclo[3.2.1]oct-1-yl)-1,3-dipropyl-3,7-dihydro-purine-2,6-dione.

10. The compound of claim 7, wherein the compound is 5-(2,6-Dioxo-1,3-dipropyl-2,3,6,7-tetrahydro-1H-purin-8-yl)-bicyclo[3.2.1]octane-2-carboxylic acid.

11. The compound of claim 6, wherein $R_3$ is

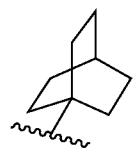

and wherein $R_3$ is either unsubstituted or substituted with one or more substituents selected from the group consisting of hydroxy, $R_5$-alkyl, —$R_5$, $R_5$-alkenyl, alkoxycarbonyl, alkoxycarbonylalkyl, alkoxycarbonylalkenyl, hydroxyalkyl, aldehydo, alkoxyalkyl, $R_5$-alkoxy, $R_5$-alkylcarbamoyl, and $R_5$-alkyl(alkyl)carbamoyl.

12. The compound of claim 11, wherein the compound is 8-(4Hydroxy-bicyclo[2.2.2]oct-1-yl)-1,3-dipropyl-3,7-dihydro-purine-2,6-dione.

13. The compound of claim 11, wherein the compound is 4-(2,6-Dioxo-1,3-dipropyl-2,3,6,7-tetrahydro-1H-purin-8-yl)-bicyclo[2.2.2]octane-1-carboxylic acid.

14. The compound of claim 11, wherein the compound is 4-(2,6-Dioxo-1,3-dipropyl-2,3,6,7-tetrahydro-1H-purin-8-yl)-bicyclo[2.2.2]octane-1-carbaldehyde.

15. The compound of claim 11, wherein the compound is 4-(2,6-Dioxo-1,3-dipropyl-2,3,6,7-tetrahydro-1H-purin-8-yl)-bicyclo[2.2.2]octane-1-carboxylic acid methyl ester.

16. The compound of claim 11, wherein the compound is 3-[4-(2,6-Dioxo-1,3-dipropyl-2,3,6,7-tetrahydro-1H-purin-8-yl)-bicyclo[2.2.2]oct-1-yl]-acrylic acid methyl ester.

17. The compound of claim 11, wherein the compound is 3-[4-(2,6-Dioxo-1,3-dipropyl-2,3,6,7-tetrahydro-1H-purin-8-yl)-bicyclo[2.2.2]oct-1-yl]-propionic acid methyl ester.

18. The compound of claim 11, wherein the compound is 3-[4-(2,6-Dioxo-1,3-dipropyl-2,3,6,7-tetrahydro-1H-purin-8-yl)-bicyclo[2.2.2]oct-1-yl]-acrylic acid.

19. The compound of claim 11, wherein the compound is 3-[4-(2,6-Dioxo-1,3-dipropyl-2,3,6,7-tetrahydro-1H-purin-8-yl)-bicyclo[2.2.2]oct-1-yl]-propionic acid.

20. The compound of claim 11, wherein the compound is 4-[4-(2,6-Dioxo-1,3-dipropyl-2,3,6,7-tetrahydro-1H-purin-8-yl)-bicyclo[2.2.2]oct-1-yl]-butyric acid.

21. The compound of claim 11, wherein the compound is Phosphoric acid mono-[4-(2,6-dioxo-1,3-dipropyl-2,3,6,7-tetrahydro-1H-purin-8-yl)-bicyclo[2.2.2]oct-1-yl]ester.

22. The compound of claim 11, wherein the compound is {[4-(2,6-Dioxo-1,3-dipropyl-2,3,6,7-tetrahydro-1H-purin-8-yl)-bicyclo[2.2.2]octane-1-carbonyl]-methyl-amino}-acetic acid.

23. The compound of claim 11, wherein the compound is {[4-(2,6-Dioxo-1,3-dipropyl-2,3,6,7-tetrahydro-1H-purin-8-yl)-bicyclo[2.2.2]octane-1-carbonyl]-amino}-acetic acid.

24. The compound of claim 11, wherein the compound is 3-[4-(2,6-Dioxo-1,3-dipropyl-2,3,6,7-tetrahydro-1H-purin-8-yl)-bicyclo[2.2.2]oct-1-yloxy]-propionic acid.

25. The compound of claim 11, wherein the compound is 3-[4-(2,6-Dioxo-1,3-dipropyl-2,3,6,7-tetrahydro-1H-purin-8-yl)-bicyclo[2.2.2]oct-1-yloxy]-propionic acid methyl ester.

26. The compound of claim 11, wherein the compound is 3-[4-(2,6-Dioxo-1,3-dipropyl-2,3,6,7-tetrahydro-1H-purin-8-yl)-bicyclo[2.2.2]oct-1-yloxy]-propionic acid t-butyl ester.

27. The compound of claim 11, wherein the compound is 3-[4-(2,6-Dioxo-1,3-dipropyl-2,3,6,7-tetrahydro-1H-purin-8-yl)-bicyclo[2.2.2]oct-1-yl]-2-methyl-propionic acid.

28. The compound of claim 6 wherein $R_3$ is

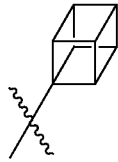

and wherein $R_3$ is either unsubstituted or substituted with one or more substituents selected from the group consisting of $R_5$-alkyl, —$R_5$, $R_5$-alkenyl, alkoxycarbonyl, alkoxycarbonylalkenyl, hydroxyalkyl, aldehydo, and hydroxy.

29. A medicament composition comprising a compound of claim 1 together with a suitable excipient.

30. A method of treating a subject suffering from a disease selected from the group consisting of respiratory disorders, diseases for which diuretic treatment is indicated, depression, traumatic brain damage, respiratory depression, cystic fibrosis, cirrhotic ascites, neonatal apnea, renal failure, diabetes, and asthma comprising administering to the subject an effective adenosine antagonizing amount of a compound of claim 1.

31. A method of treating a subject suffering from congestive heart failure or renal dysfunction comprising administering to the subject an effective adenosine antagonizing amount of a compound of claim 1.

32. The compound of claim 6 wherein $R_3$ is

and wherein $R_3$ is either unsubstituted or substituted with one or more substituents selected from the group consisting of $R_5$-alkyl, —$R_5$, $R_5$-alkenyl, $R_5$-alkoxy, alkoxycarbonyl, alkoxycarbonylalkenyl, hydroxyalkyl, aldehydo, and hydroxy.

33. The compound of claim 32, wherein the compound is [5-(2,6-Dioxo-1,3-dipropyl-2,3,6,7-tetrahydro-1H-purin-8-yl)-bicyclo[3.2.2]non-1-yloxy]-acetic acid.

34. The compound of claim 32, wherein the compound is 8-(5-Hydroxy-bicyclo[3.2.2]non-1-yl)-1,3-dipropyl-3,7-dihydro-purine-2,6-dione.

35. The compound of claim 32, wherein the compound is 5-(2,6-Dioxo-1,3-dipropyl-2,3,6,7-tetrahydro-1H-purin-8-yl)-bicyclo[3.2.2]nonane-1-carboxylic acid.

36. The compound of claim 6 wherein $R_3$ is

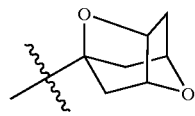

and wherein $R_3$ is either unsubstituted or substituted with one or more substituents selected from the group consisting of hydroxy, $R_5$-alkoxy, $R_5$-alkenyl, and alkoxycarbonyl.

37. The compound of claim 36, wherein the compound is 8-(4-hydroxy-7-methyl-2,6-dioxa-tricyclo[3.3.1.0]non-1,3-dipropyl-3,7-dihydro-purine-2,6-dione.

38. The compound of claim 36, wherein the compound is [1-(2,6-dioxo-1,3-dipropyl-2,3,6,7-tetrahydro-1H-purin-8-yl)-7-methyl-2,6-dioxa-tricyclo[3.3.1.0]non-4-yloxy]-acetic acid.

* * * * *

UNITED STATES PATENT AND TRADEMARK OFFICE
CERTIFICATE OF CORRECTION

PATENT NO. : 6,649,600 B1
DATED : November 18, 2003
INVENTOR(S) : Kiyoto Maruoka It is certified that error appears in the above-identified patent and that said Letters Patent is hereby corrected as shown below:

Title page,
Item [56], References Cited, OTHER PUBLICATIONS, "Suzuki et al.," reference, change "Antagognists" to -- Antagonists --.
Item [57] ABSTRACT,
Line 4, change "usefull" to -- useful --.

Column 3,
Line 41, change "substitents" to -- substituents --.
Line 55, change "dialkylaminoalkyiamino" to -- dialkylaminoalkylamino --.

Column 11,
Scheme 1, step between compounds (E) and (F), change "IN" to -- 1N --.

Column 12,
Scheme 1, compound (C),
change                               to

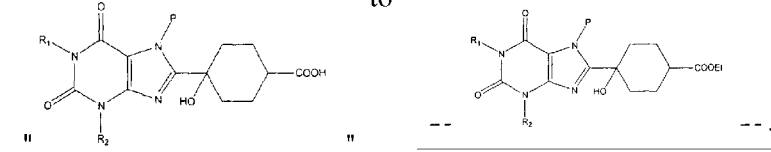

-- --.

Column 14,
Line 60, delete "or".

Column 15,
Line 20, change "alerntive" to -- alternative --.
Line 50, change "P(o-tolyl)" to -- P(o-tolyl)$_3$, --.
Line 51, delete "$_2$,".

Column 17,
Line 14, change "dimethylsudfoxide" to -- dimethylsulfoxide --.
Line 36, change "diusobutyl" to -- diisobutyl --.

Column 18,
Line 11, change "methanesulifonic" to -- methanesulfonic --.
Line 46, change "trifluoromethylsullfonyl" to -- trifluoromethylsulfonyl --.

UNITED STATES PATENT AND TRADEMARK OFFICE
CERTIFICATE OF CORRECTION

PATENT NO. : 6,649,600 B1
DATED : November 18, 2003
INVENTOR(S) : Kiyoto Maruoka It is certified that error appears in the above-identified patent and that said Letters Patent is hereby corrected as shown below:

Column 20,
Lines 7 and 53, delete "of".

Column 22,
Line 42, change "a t dehyde" to -- aldehyde --.
Line 54, change "H120" to -- $H_2O$ --.
Line 55, change "dilute," to -- diluted --.
Line 65, change "3-[-(2,6-Dioxo-" to -- 3- [1- (2,6-Dioxo- --.

Column 25,
Line 2, change "satuiaied" to -- saturated --.

Column 26,
Line 11, change "40-m1" to -- 40 ml --.

Column 29,
Line 20, change "1H" to -- $^1H$ --.

Column 30,
Lines 2 and 4, change "2.6-dione" to -- 2,6-dione --.
Line 24, change "yloxyl" to -- yloxy] --.

UNITED STATES PATENT AND TRADEMARK OFFICE
CERTIFICATE OF CORRECTION

PATENT NO. : 6,649,600 B1
DATED : November 18, 2003
INVENTOR(S) : Kiyoto Maruoka It is certified that error appears in the above-identified patent and that said Letters Patent is hereby corrected as shown below:

Column 30,
Line 30, change "oct- -yloxy" to -- oct-1-yloxy --.

Column 32,
Line 33, change "aminol" to -- amino] --.

Column 33,
Line 6, change "aminol" to -- amino} --.
Line 53, change "Example 27d: 27d:" to -- Example 27d: --.

Column 34,
Line 48, change "pH 8" to -- pH~8 --.

Column 37,
Line 2, change "wvas" to -- was --.
Line 52, change "bicyclo[2.2.9]" to -- bicyclo [2 . 2 . 2 ] -- .

Column 38,
Line 46, change "he" to -- the --.

Column 41,
Line 30, change "in" to -- on --.

Column 43,
Line 6, "furan-2H-" to -- furan-2- --.

Column 44,
Line 3, change "isobultylchloroformate" to -- isobutylchloroformate --.

Column 50,
Line 66, change "aqeuous" to -- aqueous --.

Column 54,
Line 7, delete "a".
Line 42, change "-2,6dione" to -- -2,6-dione --.

UNITED STATES PATENT AND TRADEMARK OFFICE
CERTIFICATE OF CORRECTION

PATENT NO. : 6,649,600 B1
DATED : November 18, 2003
INVENTOR(S) : Kiyoto Maruoka It is certified that error appears in the above-identified patent and that said Letters Patent is hereby corrected as shown below:

Column 59,
Line 48, change "ias" to -- is --.

Column 61,
Lines 49 and 62, change "2,6Dioxo-" to -- 2,6-Dioxo- --.

Column 62,
Line 32, change "misture" to -- mixture --.
Line 34, change "dolution" to -- solution --.
Line 55, change "are are removed" to -- are removed --.

Column 64,
Line 26, change "mol/mg" to -- fmol/mg --.

Column 66,
Line 17, change "substituenits" to -- substituents --.
Line 25, change "aldehyde" to -- aldehydo --.

Column 68,
Line 39, change "4Hydroxy-" to -- 4-Hydroxy- --.

Column 70,
Line 39, change "non-1,3" to -- non-1-yl-1,3 --.

Signed and Sealed this

Twenty-seventh Day of July, 2004

JON W. DUDAS
*Acting Director of the United States Patent and Trademark Office*

UNITED STATES PATENT AND TRADEMARK OFFICE
CERTIFICATE OF CORRECTION

PATENT NO.   : 6,649,600 B1
DATED        : November 18, 2003
INVENTOR(S)  : William F. Kiesman It is certified that error appears in the above-identified patent and that said Letters Patent is hereby corrected as shown below:

Title page,
Item [56], References Cited, OTHER PUBLICATIONS, "Suzuki et al.," reference, change "Antagognists" to -- Antagonists --.
Item [57] ABSTRACT,
Line 4, change "usefull" to -- useful --.

Column 3,
Line 41, change "substitents" to -- substituents --.
Line 55, change "dialkylaminoalkyiamino" to -- dialkylaminoalkylamino --.

Column 11,
Scheme 1, step between compounds (E) and (F), change "IN" to -- 1N --.

Column 12,
Scheme 1, compound (C),
change                              to

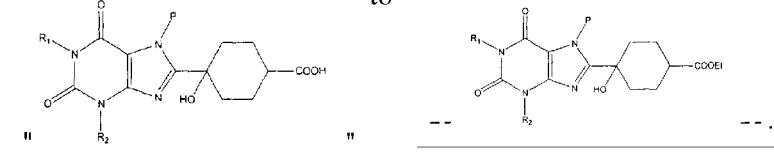

--.

Column 14,
Line 60, delete "or".

Column 15,
Line 20, change "alterntive" to -- alternative --.
Line 50, change "P(o-tolyl)" to -- P(o-tolyl)$_3$, --.
Line 51, delete "$_2$,".

Column 17,
Line 14, change "dimethylsudfoxide" to -- dimethylsulfoxide --.
Line 36, change "diusobutyl" to -- diisobutyl --.

Column 18,
Line 11, change "methanesulifonic" to -- methanesulfonic --.
Line 46, change "trifluoromethylsullfonyl" to -- trifluoromethylsulfonyl --.

UNITED STATES PATENT AND TRADEMARK OFFICE
CERTIFICATE OF CORRECTION

PATENT NO.      : 6,649,600 B1
DATED           : November 18, 2003
INVENTOR(S)     : William F. Kiesman It is certified that error appears in the above-identified patent and that said Letters Patent is hereby corrected as shown below:

Column 20,
Lines 7 and 53, delete "of".

Column 22,
Line 42, change "a t dehyde" to -- aldehyde --.
Line 54, change "H120" to -- $H_2O$ --.
Line 55, change "dilute," to -- diluted --.
Line 65, change "3-[-(2,6-Dioxo-" to -- 3- [1- (2,6-Dioxo- --.

Column 25,
Line 2, change "satuiaied" to -- saturated --.

Column 26,
Line 11, change "40-m1" to -- 40 ml --.

Column 29,
Line 20, change "1H" to -- $^1H$ --.

Column 30,
Lines 2 and 4, change "2.6-dione" to -- 2,6-dione --.
Line 24, change "yloxyl" to -- yloxy] --.

UNITED STATES PATENT AND TRADEMARK OFFICE
CERTIFICATE OF CORRECTION

PATENT NO.   : 6,649,600 B1
DATED        : November 18, 2003
INVENTOR(S)  : William F. Kiesman It is certified that error appears in the above-identified patent and that said Letters Patent is hereby corrected as shown below:

Column 30,
Line 30, change "oct- -yloxy" to -- oct-1-yloxy --.

Column 32,
Line 33, change "aminol" to -- amino] --.

Column 33,
Line 6, change "aminol" to -- amino} --.
Line 53, change "Example 27d: 27d:" to -- Example 27d: --.

Column 34,
Line 48, change "pH 8" to -- pH~8 --.

Column 37,
Line 2, change "wvas" to -- was --.
Line 52, change "bicyclo[2.2.9]" to -- bicyclo [2 . 2 . 2 ] -- .

Column 38,
Line 46, change "he" to -- the --.

Column 41,
Line 30, change "in" to -- on --.

Column 43,
Line 6, "furan-2H-" to -- furan-2- --.

Column 44,
Line 3, change "isobultylchloroformate" to -- isobutylchloroformate --.

Column 50,
Line 66, change "aqeuous" to -- aqueous --.

Column 54,
Line 7, delete "a".
Line 42, change "-2,6dione" to -- -2,6-dione --.

UNITED STATES PATENT AND TRADEMARK OFFICE
CERTIFICATE OF CORRECTION

PATENT NO. : 6,649,600 B1
DATED : November 18, 2003
INVENTOR(S) : William F. Kiesman It is certified that error appears in the above-identified patent and that said Letters Patent is hereby corrected as shown below:

Column 59,
Line 48, change "ias" to -- is --.

Column 61,
Lines 49 and 62, change "2,6Dioxo-" to -- 2,6-Dioxo- --.

Column 62,
Line 32, change "misture" to -- mixture --.
Line 34, change "dolution" to -- solution --.
Line 55, change "are are removed" to -- are removed --.

Column 64,
Line 26, change "mol/mg" to -- fmol/mg --.

Column 66,
Line 17, change "substituenits" to -- substituents --.
Line 25, change "aldehyde" to -- aldehydo --.

Column 68,
Line 39, change "4Hydroxy-" to -- 4-Hydroxy- --.

Column 70,
Line 39, change "non-1,3" to -- non-1-yl-1,3 --.

This certificate supersedes Certificate of Correction issued July 27, 2004.

Signed and Sealed this

Twenty-ninth Day of March, 2005

JON W. DUDAS
*Director of the United States Patent and Trademark Office*